(12) United States Patent
Jimenez et al.

(10) Patent No.: US 11,305,016 B2
(45) Date of Patent: *Apr. 19, 2022

(54) VITAMIN D3 AND ANALOGS THEREOF FOR TREATING ALOPECIA

(71) Applicant: Berg LLC, Framingham, MA (US)

(72) Inventors: Joaquin J. Jimenez, Miami, FL (US); Niven Rajin Narain, Cambridge, MA (US); John Patrick McCook, Frisco, TX (US)

(73) Assignee: Berg LLC, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,669

(22) Filed: Jan. 16, 2018

(65) Prior Publication Data

US 2018/0369381 A1 Dec. 27, 2018

Related U.S. Application Data

(63) Continuation of application No. 12/853,431, filed on Aug. 10, 2010, now Pat. No. 9,901,637.

(60) Provisional application No. 61/234,178, filed on Aug. 14, 2009.

(51) Int. Cl.

| A61K 45/06 | (2006.01) |
|---|---|
| A61K 8/67 | (2006.01) |
| A61K 31/59 | (2006.01) |
| A61K 31/592 | (2006.01) |
| A61K 31/593 | (2006.01) |
| A61Q 7/00 | (2006.01) |

(52) U.S. Cl.
CPC ............. *A61K 45/06* (2013.01); *A61K 8/67* (2013.01); *A61K 31/59* (2013.01); *A61K 31/592* (2013.01); *A61K 31/593* (2013.01); *A61Q 7/00* (2013.01)

(58) Field of Classification Search
CPC ........ A61K 8/67; A61K 31/59; A61K 31/592; A61K 31/593; A61Q 7/00
See application file for complete search history.

(56) References Cited

U.S. PATENT DOCUMENTS

| 4,425,916 A | 1/1984 | Bowen |
|---|---|---|
| 4,566,455 A | 1/1986 | Kramer |
| 5,017,371 A | 5/1991 | Cummins |
| 5,342,411 A | 8/1994 | Maxted et al. |
| 5,449,668 A | 9/1995 | Sestelo et al. |
| 5,486,509 A | 1/1996 | Jimenez et al. |
| 6,238,683 B1 | 5/2001 | Burnett et al. |
| 6,291,443 B1 | 9/2001 | Jimenez et al. |
| 6,531,459 B1 | 3/2003 | Steinmeyer et al. |
| 6,689,922 B1 | 2/2004 | Bernardon |
| 6,844,326 B2 | 1/2005 | Li |
| 8,143,238 B2 * | 3/2012 | DeLuca ................. A61K 31/59 514/167 |
| 9,901,637 B2 | 2/2018 | Jimenez et al. |
| 2002/0035097 A1 | 3/2002 | Jimenez et al. |
| 2002/0103173 A1 | 8/2002 | Takenouchi et al. |
| 2002/0132799 A1 | 9/2002 | Takenouchi et al. |
| 2003/0059464 A1 | 3/2003 | Zhao et al. |
| 2004/0053895 A1 | 3/2004 | Mazess et al. |
| 2004/0224929 A1 | 11/2004 | Bernardon |
| 2006/0166949 A1 | 7/2006 | Binderup et al. |
| 2007/0041910 A1 | 2/2007 | Pitre et al. |
| 2009/0130216 A1 | 5/2009 | Cartt et al. |
| 2016/0228458 A1 | 8/2016 | Narain et al. |
| 2019/0343847 A1 | 11/2019 | Sarangarajan et al. |

FOREIGN PATENT DOCUMENTS

| CN | 1732902 A | 2/2006 |
|---|---|---|
| EP | 1013269 A1 | 6/2000 |
| EP | 1477483 A1 | 11/2004 |
| EP | 1952808 A2 | 8/2008 |
| GB | 2260903 A | 5/1993 |
| JP | H08-295628 A | 11/1996 |
| JP | 09-299484 | 11/1997 |
| WO | 1993/000079 A1 | 1/1993 |
| WO | 1994/13280 A1 | 6/1994 |
| WO | 1996/037193 A1 | 11/1996 |
| WO | 1998/55104 A1 | 12/1998 |
| WO | 1998/56387 A1 | 12/1998 |
| WO | 2000/003700 A1 | 1/2000 |
| WO | 2002/030430 A1 | 4/2002 |
| WO | 2003/047594 A1 | 6/2003 |

(Continued)

OTHER PUBLICATIONS

Jimenez et al., "Protection from chemotherapy-induced alopecia by 1,25-dihydroxyvitamin D3," Cancer Research, vol. 52, No. 18 (1992), pp. 5123-5125.
International Search Report and Written Opinion issued in PCT/US2010/044765.
Sredni, et al., "The protective role of the immunomodulator AS101 against chemotherapy-induced alopecia studies on human and animal models," Int J Cancer. 1996;65(1):97-103.
Chen et al., "Protection Against Cyclophosphamide-Induced Alopecia and Inhibition of Mammary Tumor Growth by Topical 1,25-Dihydroxyvitamin D3 in Mice" Int. J. Cancer, 75:303-309, 1998.
"Growth Rate of Mlac: SD," National Laboratory Animal Center, Obtained from <http://nlac.mahidol.ac.th/nlacmuEN/o_animal_Rat.htm> Accessed on Jul. 28, 2015.
U.S. Department of Health and Hyman Services Public Health Service, "What is Alopecia Areata", Jul. 2009, Accessed Mar. 9, 2014, Obtained from <http://www.niams.nih.gov/health_info/A;opecia_Areata/alopecia_areata_ff.asp>.

(Continued)

*Primary Examiner* — Alicia L Otton
(74) *Attorney, Agent, or Firm* — McCarter & English, LLP; Jill Mello

(57) ABSTRACT

The invention provides methods and pharmaceutical compositions for preventing or treating alopecia, such as chemotherapy-induced alopecia (CIA). The pharmaceutical compositions of the invention comprises an effective amount of a vitamin D compound in a formulation that topically delivers the vitamin D compound to the epidermis layer but substantially avoids the dermis layer. In chemotherapy patients, the pharmaceutical compositions of the invention can be administered either before or concurrent with the chemotherapy medication.

20 Claims, 42 Drawing Sheets

(56) References Cited

FOREIGN PATENT DOCUMENTS

| WO | 2006/120681 A2 | 11/2006 |
| WO | 2014/194133 A1 | 12/2014 |

OTHER PUBLICATIONS

Paus et al., Cancer Research, (1996); 56; 4438-4443.

Li et al., "Hair shaft elongation, follicle growth, and spontaneous regression in long-term, gelatin sponge-supported histoculture of human scalp skin" Proc. Nat'l. Acad. Sci., vol. 89: 8764-8768, 1992.

Calverley et al., "Synthesis of MC 903, A biologically active vitamin D metabolite analogue" Tetrahedron, vol. 43 (20):4609-4619, 1987.

Bleiker et al., 'Atrophic telogen effluvium' from cytotoxic drugs and a randomized controlled trial to investigate the possible protective effect of pretreatment with a topical vitamin D analogue in humans. Br J Dermatol. Jul. 2005;153(1):103-12.

Cai et al., Abnormal expression of VDR in the hair follicle of alopecia areata. Guangdong Medical J. May 31, 2011,32(10):1259-1262.

California State Board of Pharmacy. Measuring Liquid Medicine. Retrieved online at: http://www.pharmacy.ca.gov/publications/measuring_liquid_medicine.pdf. Nov. 2008. 1 page.

ClinicalTrials.gov. NCT01588522, retrieved online at: https://clinicaltrials.gov/ct2/show/NCT01588522. Apr. 21, 2017.

Dr. Mercola Premium Supplements. Sunshine Mist Vitamin D. Retrieved online at: http://products.mercola.com/vitamin-d-spray/. Internet Archive Wayback Machine. Mar. 3, 2011. 1 page.

Mercola.com, The 5 Second 'Super Spray' 85% of People Need. Retrieved online at: http://products.mercola.com/vitamin-d-spray/. 7 pages (1997-2013).

Mercola.com Vitamin D Spray—Benefits of Sunlight Product label retrieved online at: https://web.archive.org/web/20110303080308/http://mercola.fileburst.com/PDF/product-labels/vitaminD-spray-label-v100.pdf. 2017. 7 pages.

Narain et al., Protection from chemotherapy-induced alopecia by cytotech lbs API 31543 in a multichemotherapy course model of chloroleukemia. Proceedings: AACR 101st Annual Meeting Apr. 17-21, 2010. Abstract 2865. 3 pages.

USDA Dietary Supplement Ingredient Database. Retrieved online at: https://dietarysupplementdatabase.usda.nih.gov/. Nov. 2008.

USDA National Nutrient Database for Standard ReferenceRelease 28. Nutrients: Vitamen D (IU). Retrieved online at: https://ods.od.nih.gov/pubs/usdandb/VitaminD-Content.pdf. Jun. 21, 2017. 155 pages.

Zhuo et al., Relationship between vitamin D, vitamin D receptor and hair. Chinese J of Tissue Engineering Res. Apr. 1, 2012;16(14):2641-2644.

* cited by examiner

VITAMIN D3 AND ANALOGS THEREOF FOR TREATING ALOPECIA

RELATED APPLICATIONS

This application is a continuation application of U.S. patent application Ser. No. 12/853,431, filed Aug. 10, 2010 which, in turn, claims priority to U.S. Provisional Patent Application No. 61/234,178, filed Aug. 14, 2009. The contents of the foregoing application are hereby incorporated in their entirety.

BACKGROUND OF THE INVENTION

Alopecia is a common and distressing side effect of many chemotherapeutic agents and for which there is currently few effective preventive measures. In a recent study, thirty-five of forty-six patients receiving chemotherapy ranked alopecia as a more disturbing side effect than vomiting (Tierney et al, B. J. Cancer, 62:527-528, 1990).

Currently, those suffering from alopecia can only attempt to regrow lost hair by repeated applications of topical steroids or can attempt to maintain hair growth by topical application of minoxidil. Moreover, there are currently no approved therapeutic agents with the ability to prevent alopecia from occurring as a side effect during chemotherapy treatment, although there have been some promising studies. For example, using a young rat model, it has been demonstrated that ImuVert, a biologic response modifier prepared from the bacterium *Serratia marcescens*, protected the animals from alopecia induced by cytosine arabinoside or adriamycin (Hussein et al., *Science* 249: 1564-1566, 1990). In subsequent studies, similar protection from ARA-C-induced alopecia was observed from recombinant interleukin-1 (IL-1) beta (Jimenez et al., *FASEB J.* 1991). Despite these promising results, there remains a need for a safe and effective therapeutic agent that treats alopecia in those suffering from this disorder, and further, prevents chemotherapy-induced alopecia in those receiving cancer treatment.

SUMMARY OF THE INVENTION

The present invention relates to the use of vitamin D compounds, such as Vitamin D3 or calcitriol and its analogs or a metabolite thereof, dosages and formulations thereof, to prevent or treat alopecia (e.g., chemotherapy-induced alopecia (CIA)).

Accordingly, in one aspect, the invention provides methods of preventing or treating alopecia in an individual by topically administering to the individual a pharmaceutical composition comprising a therapeutically effective amount of a vitamin D compound formulated to be delivered to epidermis while substantially avoiding dermis delivery.

In some embodiments, the pharmaceutical composition comprises about 40% (w/w) propylene glycol and about 60% (w/w) anhydrous absolute ethanol (200 proof, U.S.); or about 30% (w/w) propylene glycol, about 10% (w/w) ethoxydiglycol or transcutol, and about 60% (w/w) anhydrous absolute ethanol (200 proof, U.S.).

In other embodiments, the vitamin D compound is represented by Formula (I):

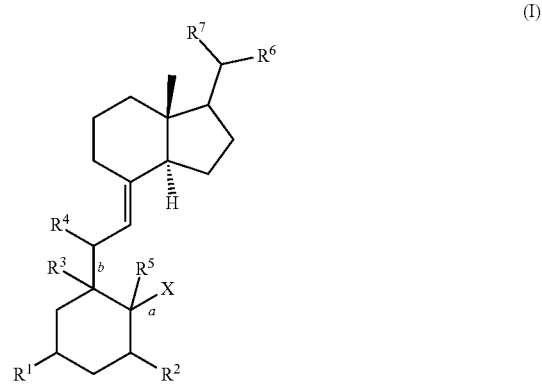

wherein a and b are each independently a single or double bond;

X is —$CH_2$ when a is a double bond, or X is hydrogen or a hydroxyl substituted alkyl when a is a single bond;

$R^1$ is hydrogen, hydroxyl, alkoxyl, tri-alkyl silyl or alkyl, optionally substituted with one to three halogen, hydroxyl, cyano or —NR'R" moieties;

$R^2$ is hydrogen, hydroxyl, —O-trialkyl silyl, or alkyl, alkoxyl or alkenyl, optionally substituted with one to three halogen, hydroxyl, cyano or —NR'R" moieties;

$R^3$ is absent when b is a double bond or $R^3$ is hydrogen, hydroxyl or alkyl, or $R^3$ and $R^1$ together with the carbon atoms to which they are attached may be linked to form 5-7 membered carbocyclic ring when b is a single bond;

$R^4$ is absent when b is a double bond or hydrogen, halogen or hydroxyl when b is a single bond;

$R^5$ is absent when a is a double bond or $R^5$ is hydrogen, halogen or hydroxyl when a is a single bond;

$R^6$ is alkyl, alkenyl, alkynyl, cycloalkyl, heterocyclicyl, alkyl-O-alkyl, alkyl-$CO_2$-alkyl optionally substituted with one to five, hydroxyl, oxo, halogen, alkoxyl, aryl, heteroaryl, cyano, nitro or —NR'R" moieties;

$R^7$ is alkyl optionally substituted with one to three hydroxyl, halogen, alkoxyl, aryl, heteroaryl, cyano, nitro or —NR'R" moieties; and, R' and R" are each, independently, hydrogen, hydroxyl, halogen, alkyl or alkoxyl, and pharmaceutically acceptable salts thereof.

In some other embodiments, the vitamin D compound is represented by Formula (II):

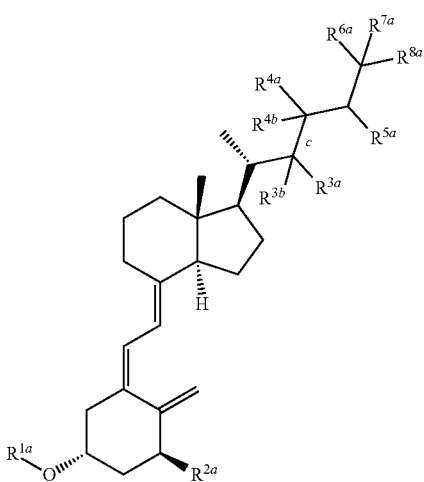

(II)

wherein c is a single or double bond;

$R^{1a}$ is hydrogen, tri-alkyl silyl or alkyl, optionally substituted with one to three halogen, hydroxyl, cyano or —NR'R" moieties;

$R^{2a}$ is hydrogen, hydroxyl, —O-trialkyl silyl, or alkyl, alkoxyl or alkenyl, optionally substituted with one to three halogen, hydroxyl, cyano or —NR'R" moieties;

$R^{3a}$, $R^{4a}$ are absent when c is a double bond, or are each independently hydrogen, hydroxyl, halogen, alkoxyl or alkyl optionally substituted with one to three hydroxyl or halogen moieties when c is a single bond $R^{3b}$, $R^{4b}$, $R^{5a}$, $R^{6a}$, $R^{7a}$, and $R^{8a}$ are each, independently, hydrogen, hydroxyl, halogen, alkoxyl or alkyl optionally substituted with one to three hydroxyl or halogen moieties, or any two of $R^{6a}$, $R^{7a}$ and $R^{8a}$ may be linked to form a 3-7 membered carbocyclic ring, and pharmaceutically acceptable salts thereof.

In yet another embodiments, the vitamin D compound is 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In a further embodiments, the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In other embodiments, the vitamin D compound exhibits similar or identical gene regulation profile as equivalent amount of calcitriol in normal keratinocytes.

In some embodiments, the vitamin D compound modulates the expression of one or more genes whose expression levels are modulated by an equivalent amount of calcitriol.

In yet other embodiments, the vitamin D compound modulates the expression of HSPA2 or HSF4 mRNA, HSPB1 or DNAJC6 mRNA in normal keratinocytes.

In another embodiment, the vitamin D compound modulates the expression of SLC1A1, KCNB2, KCNN4 or SLC1A3 protein in normal keratinocytes.

In other embodiments, the vitamin D compound modulates the expression of one or more proteins in Table 3-1 and Table 3-2 by at least about 2-fold.

In yet another embodiment, the vitamin D compound induces overexpression of one or more proteins in Tables 3-3, 3-4, 3-5 or 3-6 after about 24-hour exposure of normal keratinocytes to said vitamin D compound.

In other embodiments, the vitamin D compound induces overexpression in normal keratinocytes of one or more of: GST, Keratin 1, Keratin 17, Galectin 1, S100 A9 (Calprotectin), or S100 A13.

In some embodiments, the alopecia is alopecia areata (AA), alopecia totalis (AT), alopecia universalis (AU), or chemotherapy-induced alopecia (CIA).

In some other embodiments, the alopecia areata includes diffuse alopecia areata, alopecia areata monolocularis, alopecia areata *multilocularis*, and alopecia areata barbae.

In yet another embodiment, the alopecia excludes androgenetic alopecia (alopecia androgenetica) or post-chemotherapy alopecia (PCA).

In some embodiments, the individual is a primate.

In other embodiments, the individual is a human.

In other embodiments, the alopecia has not commenced in the individual.

In yet another embodiment, the individual is undergoing or about to undergo chemotherapy.

In some other embodiments, the pharmaceutical composition is administered to the individual prior to chemotherapy or concurrent with chemotherapy.

In yet other embodiment, the pharmaceutical composition is administered to the individual after the commencement of chemotherapy, but prior to the commencement of alopecia.

In some embodiments, the pharmaceutical composition does not substantially reduce the efficacy of chemotherapy.

In yet other embodiments, the chemotherapy is systemic chemotherapy.

In some embodiments, the chemotherapy includes one or more of: Anthracyclines (Adriamycin/Doxorubicin, Daunorubicin, Epirubicin, Idarubicin, Valrubicin), 5-FU, bevacizumab, Tamoxifen, Irinotecan, Paclitaxel (Taxol), Carboplatin, Etoposide, Cytoxan/Cyclophosphamide, Cisplatin, Erlotinib (Tarceva), Gemcitabine, Staurosporin, Vincristine, Imatinib (Gleevec), Gefitinib (Iressa), Sorafenib, Dasatinib, Dactinomycin, Hexamethamelamine (HMM, altretamine), Ifosfamide, bleomycin, methotrexate, Docetaxel (Taxotere), Vindesine, Vinorelbine, Topotecan, Amsacrine, Cytarabine, Busulphan, Melphalan, Vinblastine, Lomustine (CCNU), Thiotepa, Gemcitabine, Carmustine (BCNU), Mitroxantrone, Mitomycin C, Procarbazine, 6-Mercaptopurine, Sreptozotocin, Fludarabine, Raltitrexed (Tomudex), Capecitabine, and equivalents thereof.

In further embodiments, the vitamin D compound is topically administered to the individual at a dosage volume equivalent to about 0.1 μg of calcitriol/cm$^2$.

In yet other embodiments, the total dose is equivalent to about 2-100 μg of calcitriol/75 kg body weight.

In another aspect, the invention provides methods of preventing or treating alopecia in an individual, comprising topically administering to the individual a pharmaceutical composition comprising a therapeutically effective amount of a vitamin D compound represented by Formula (I):

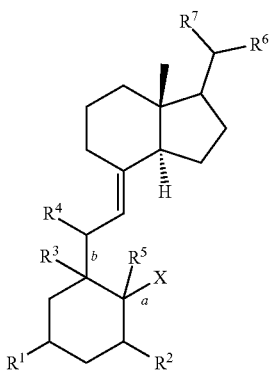

(I)

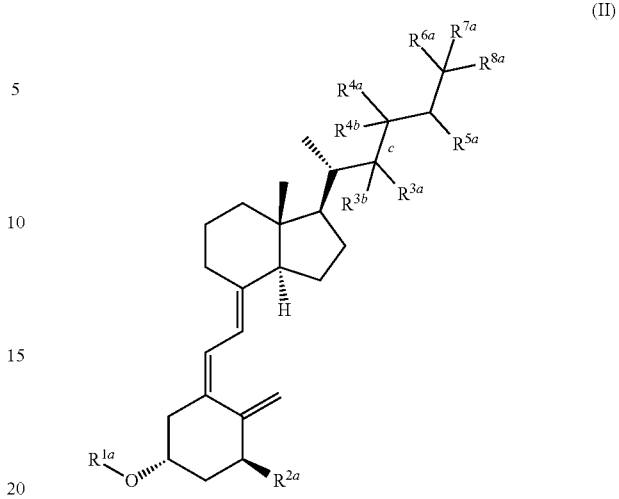

(II)

wherein
a and b are each independently a single or double bond

X is —CH$_2$ when a is a double bond, or X is hydrogen or a hydroxyl substituted alkyl when a is a single bond;

R$^1$ is hydrogen, hydroxyl, alkoxyl, tri-alkyl silyl or alkyl, optionally substituted with one to three halogen, hydroxyl, cyano or —NR'R" moieties;

R$^2$ is hydrogen, hydroxyl, —O-trialkyl silyl, or alkyl, alkoxyl or alkenyl, optionally substituted with one to three halogen, hydroxyl, cyano or —NR'R" moieties;

R$^3$ is absent when b is a double bond or R$^3$ is hydrogen, hydroxyl or alkyl, or R$^3$ and R$^1$ together with the carbon atoms to which they are attached may be linked to form 5-7 membered carbocyclic ring when b is a single bond;

R$^4$ is absent when b is a double bond or hydrogen, halogen or hydroxyl when b is a single bond;

R$^5$ is absent when a is a double bond or R$^5$ is hydrogen, halogen or hydroxyl when a is a single bond;

R$^6$ is alkyl, alkenyl, alkynyl, cycloalkyl, heterocyclicyl, alkyl-O-alkyl, alkyl-CO$_2$-alkyl optionally substituted with one to five, hydroxyl, oxo, halogen, alkoxyl, aryl, heteroaryl, cyano, nitro or —NR'R" moieties;

R$^7$ is alkyl optionally substituted with one to three hydroxyl, halogen, alkoxyl, aryl, heteroaryl, cyano, nitro or —NR'R" moieties; and, R' and R" are each, independently, hydrogen, hydroxyl, halogen, alkyl or alkoxyl, and pharmaceutically acceptable salts thereof;

wherein the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In some embodiments, the vitamin D compound is represented by Formula (II):

wherein
c is a single or double bond;

R$^{1a}$ is hydrogen, tri-alkyl silyl or alkyl, optionally substituted with one to three halogen, hydroxyl, cyano or —NR'R" moieties;

R$^{2a}$ is hydrogen, hydroxyl, —O-trialkyl silyl, or alkyl, alkoxyl or alkenyl, optionally substituted with one to three halogen, hydroxyl, cyano or —NR'R" moieties;

R$^{3a}$, R$^{4a}$ are absent when c is a double bond, or are each independently hydrogen, hydroxyl, halogen, alkoxyl or alkyl optionally substituted with one to three hydroxyl or halogen moieties when c is a single bond R$^{3b}$, R$^{4b}$, R$^{5a}$, R$^{6a}$, R$^{7a}$, and R$^{8a}$ are each, independently, hydrogen, hydroxyl, halogen, alkoxyl or alkyl optionally substituted with one to three hydroxyl or halogen moieties, or any two of R$^{6a}$, R$^{7a}$ and R$^{8a}$ may be linked to form a 3-7 membered carbocyclic ring, and pharmaceutically acceptable salts thereof.

In another aspect, the present invention provides methods of preventing or treating alopecia in an individual, comprising topically administering to the individual a pharmaceutical composition comprising a therapeutically effective amount of a vitamin D compound, wherein said vitamin D compound, when topically administered to the individual at an effective concentration of: (1) about 50 μg/mL, does not cause toxicity after at least about 25 consecutive days of drug administration; or (2) about 100 μg/mL, does not cause toxicity after at least about 7 consecutive days of drug administration.

In yet another aspect, the invention provides methods of preventing or treating alopecia in an individual, comprising topically administering to the individual a pharmaceutical composition comprising a therapeutically effective amount of a vitamin D compound for preventing or treating alopecia in said individual, without substantially interfere with the efficacy of a co-administered chemotherapeutic agent.

In one aspect, the invention provides methods of preventing or treating alopecia in an individual, comprising topically administering to the individual a pharmaceutical composition comprising a therapeutically effective amount of a vitamin D compound that:

(1) exhibits similar or identical gene regulation profile as equivalent amount of calcitriol in normal keratinocyte;

(2) modulates the expression of one or more genes whose expression levels are modulated by an equivalent amount of calcitriol;

(3) modulates the expression of HSPA2 or HSF4 mRNA, HSPB1 or DNAJC6 mRNA in normal keratinocytes;

(4) modulates the expression of SLC1A1, KCNB2, KCNN4, SLC1A3 protein in normal keratinocytes;

(5) modulates the expression of one or more proteins in Table 3-1 and Table 3-2 by at least about 2-fold;

(6) induces overexpression of one or more proteins in Tables 3-3, 3-4, 3-5 or 3-6 after about 24-hour exposure of normal keratinocytes to said vitamin D compound; or, (7) induces overexpression in normal keratinocytes of one or more of: GST, Keratin 1, Keratin 17, Galectin 1, S100 A9 (Calprotectin), or S100 A13;

wherein the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In yet another aspect, the invention provides pharmaceutical compositions for topical administration, comprising a therapeutically effective amount of a vitamin D compound for preventing or treating alopecia, wherein said vitamin D compound is formulated to be delivered to epidermis while substantially avoiding dermis delivery.

In some aspects, the pharmaceutical composition comprises about 40% (w/w) propylene glycol and about 60% (w/w) anhydrous absolute ethanol (200 proof, US), undenatured; or about 30% (w/w) propylene glycol, about 10% (w/w) ethoxydiglycol or transcutol, and about 60% (w/w) anhydrous absolute ethanol (200 proof, US), undenatured.

In some aspects, the invention provides pharmaceutical compositions for topical administration, comprising a therapeutically effective amount of a vitamin D compound for preventing or treating alopecia, wherein said vitamin D compound is represented by Formula (I):

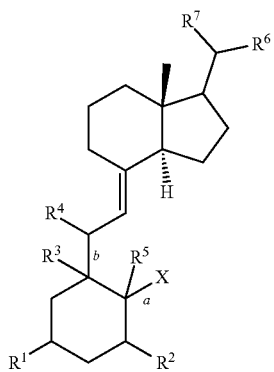

wherein a and b are each independently a single or double bond

X is —$CH_2$ when a is a double bond, or X is hydrogen or a hydroxyl substituted alkyl when a is a single bond;

$R^1$ is hydrogen, hydroxyl, alkoxyl, tri-alkyl silyl or alkyl, optionally substituted with one to three halogen, hydroxyl, cyano or —NR'R" moieties;

$R^2$ is hydrogen, hydroxyl, —O-trialkyl silyl, or alkyl, alkoxyl or alkenyl, optionally substituted with one to three halogen, hydroxyl, cyano or —NR'R" moieties;

$R^3$ is absent when b is a double bond or $R^3$ is hydrogen, hydroxyl or alkyl, or $R^3$ and $R^1$ together with the carbon atoms to which they are attached may be linked to form 5-7 membered carbocyclic ring when b is a single bond;

$R^4$ is absent when b is a double bond or hydrogen, halogen or hydroxyl when b is a single bond;

$R^5$ is absent when a is a double bond or $R^5$ is hydrogen, halogen or hydroxyl when a is a single bond;

$R^6$ is alkyl, alkenyl, alkynyl, cycloalkyl, heterocyclicyl, alkyl-O-alkyl, alkyl-$CO_2$-alkyl optionally substituted with one to five, hydroxyl, oxo, halogen, alkoxyl, aryl, heteroaryl, cyano, nitro or —NR'R" moieties;

$R^7$ is alkyl optionally substituted with one to three hydroxyl, halogen, alkoxyl, aryl, heteroaryl, cyano, nitro or —NR'R" moieties; and, R' and R" are each, independently, hydrogen, hydroxyl, halogen, alkyl or alkoxyl, and pharmaceutically acceptable salts thereof;

wherein the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In some embodiments, the vitamin D compound is represented by Formula (II):

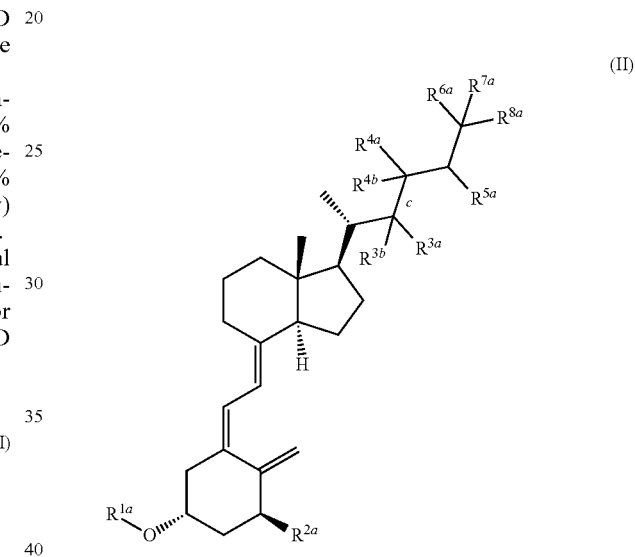

wherein c is a single or double bond;

$R^{1a}$ is hydrogen, tri-alkyl silyl or alkyl, optionally substituted with one to three halogen, hydroxyl, cyano or —NR'R" moieties;

$R^{2a}$ is hydrogen, hydroxyl, —O-trialkyl silyl, or alkyl, alkoxyl or alkenyl, optionally substituted with one to three halogen, hydroxyl, cyano or —NR'R" moieties;

$R^{3a}$, $R^{4a}$ are absent when c is a double bond, or are each independently hydrogen, hydroxyl, halogen, alkoxyl or alkyl optionally substituted with one to three hydroxyl or halogen moieties when c is a single bond;

$R^{3b}$, $R^{4b}$, $R^{5a}$, $R^{6a}$, $R^{7a}$, and $R^{8a}$ are each, independently, hydrogen, hydroxyl, halogen, alkoxyl or alkyl optionally substituted with one to three hydroxyl or halogen moieties, or any two of $R^{6a}$, $R^{7a}$ and $R^{8a}$ may be linked to form a 3-7 membered carbocyclic ring, and pharmaceutically acceptable salts thereof.

In some other aspects, the invention provides pharmaceutical compositions for topical administration, comprising a therapeutically effective amount of a vitamin D compound for preventing or treating alopecia, wherein said vitamin D compound, when topically administered to the individual at an effective concentration of:

(1) about 50 μg/mL, does not cause toxicity after at least about 25 consecutive days of drug administration; or (2) about 100 µg/mL, does not cause toxicity after at least about 7 consecutive days of drug administration.

In yet another aspect, the invention provides pharmaceutical compositions for topical administration, comprising a therapeutically effective amount of a vitamin D compound for preventing or treating alopecia, wherein said therapeutically effective amount of the vitamin D compound, when co-administered with a chemotherapeutic agent, does not substantially interfere with the efficacy of the chemotherapeutic agent.

In another aspect, the invention provides pharmaceutical compositions for topical administration, comprising a therapeutically effective amount of a vitamin D compound for preventing or treating alopecia, wherein said therapeutically effective amount of the vitamin D compound:

(1) exhibits similar or identical gene regulation profile as equivalent amount of calcitriol in normal keratinocytes;

(2) modulates the expression of one or more genes whose expression levels are promoted by an equivalent amount of calcitriol;

(3) modulates the expression of HSPA2 or HSF4 mRNA, HSPB1 or DNAJC6 mRNA in normal keratinocytes;

(4) modulates the expression of SLC1A1, KCNB2, KCNN4, or SLC1A3 protein in normal keratinocytes;

(5) modulates the expression of one or more proteins in Table 3-1 or Table 3-2 by at least about 2-fold;

(6) induces overexpression of one or more proteins in Tables 3-3, 3-4, 3-5 or 3-6 after about 24-hour exposure of normal keratinocytes to said vitamin D compound; or, (7) induces overexpression in normal keratinocytes of one or more of: GST, Keratin 1, Keratin 17, Galectin 1, S100 A9 (Calprotectin), or S100 A13;

wherein the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

It should be noted that all embodiments described herein (above and below) are contemplated to be able to combine with any other embodiment(s) where applicable, including embodiments described only under one of the aspects of the invention, and embodiments described under different aspects of the invention.

Figures 1, 18:
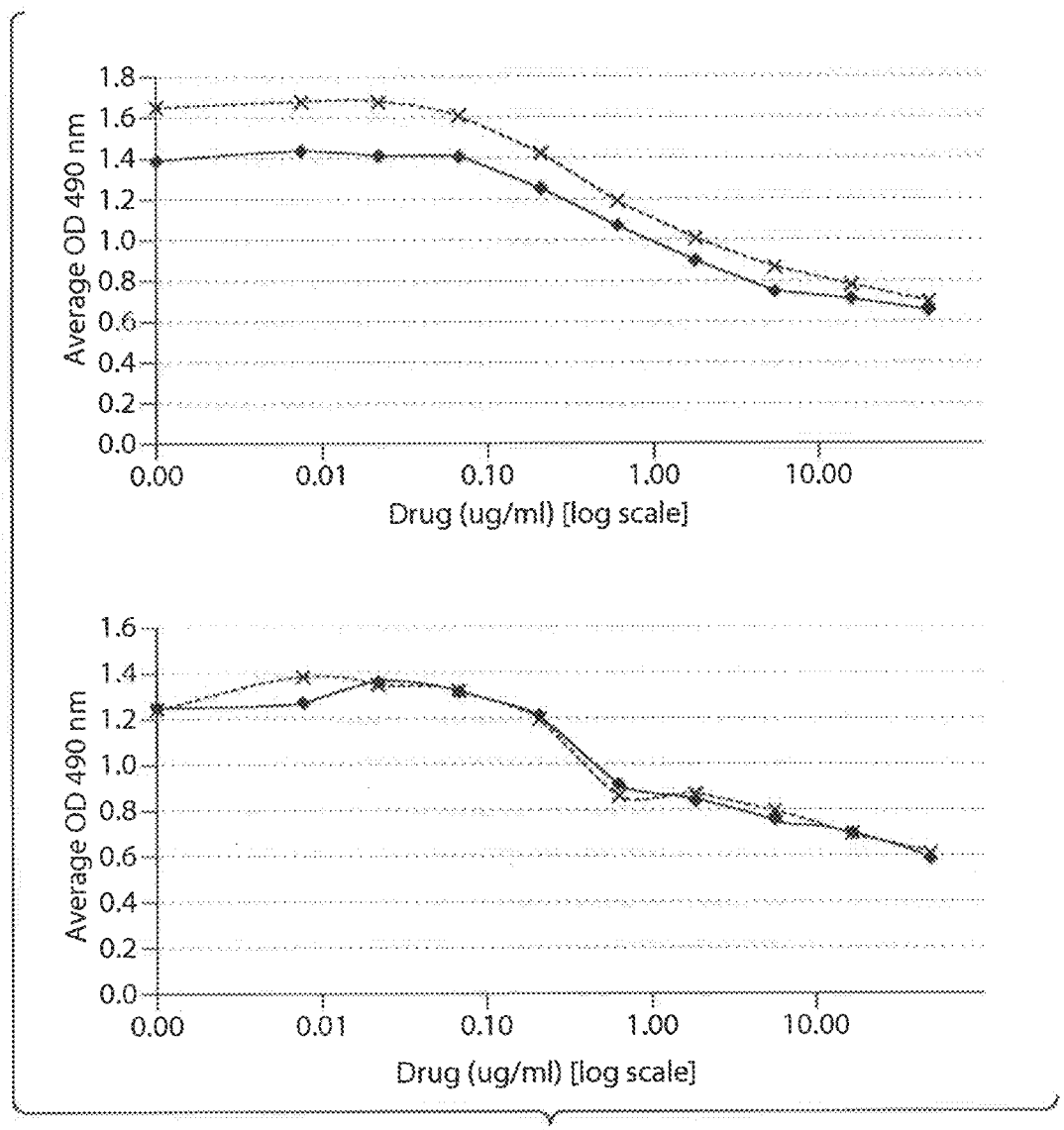
Figures 2, 18:
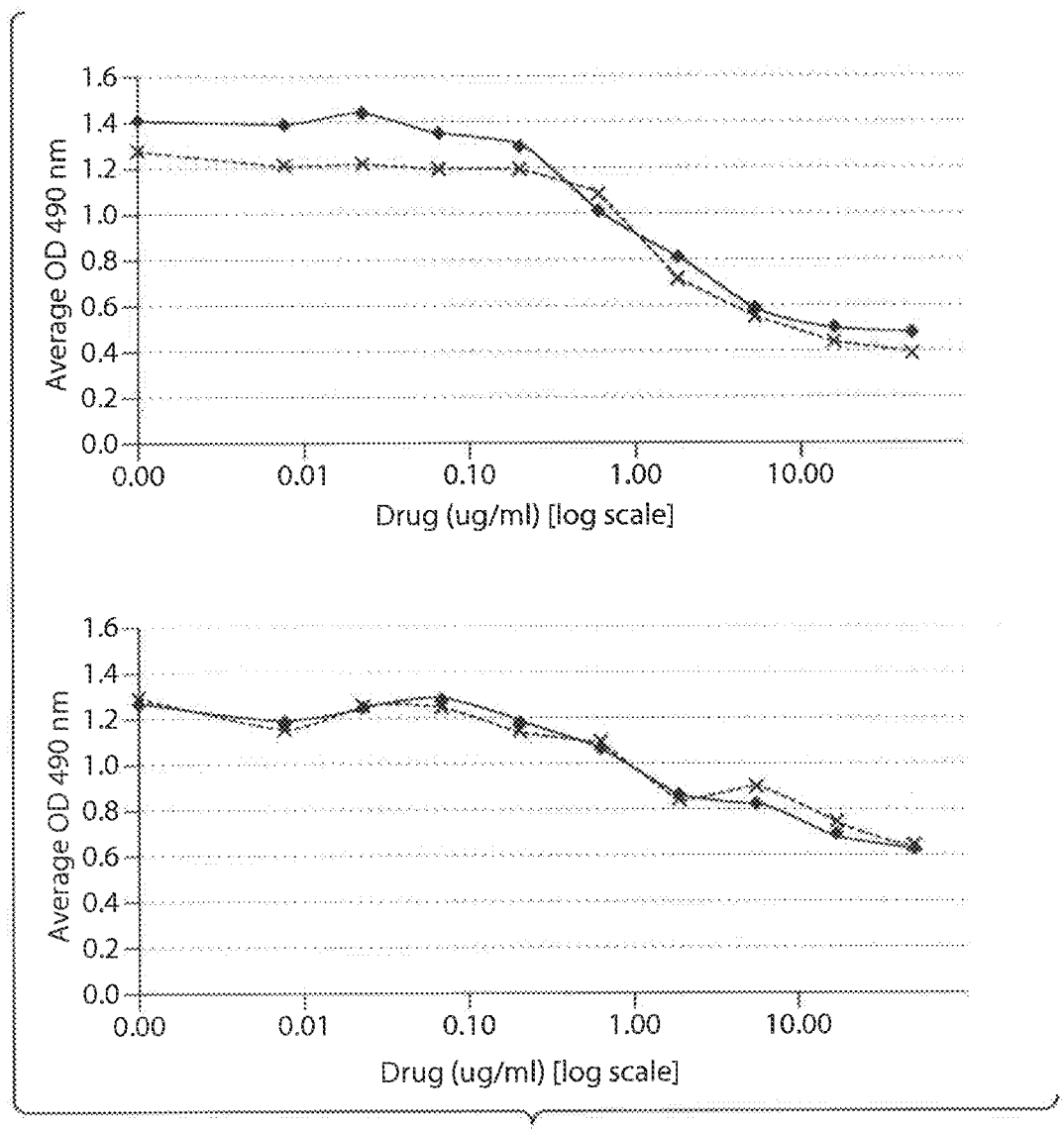

Parts I and II of FIG. 18 show that 0.1 µg/mL calcitriol protects normal keratinocytes HEKa against 5-FU, while does not appreciably affect $ED_{50}$ values of 5-FU against cancer cells.

Figure 19:
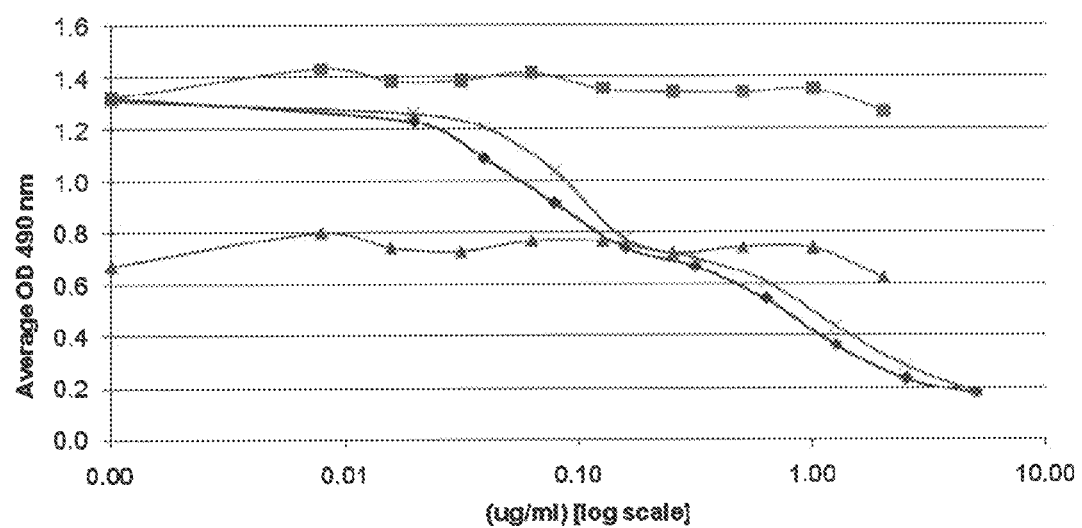

FIG. 19 shows that calcitriol does not appreciably alter the cytotoxic effect of Doxorubicin against the cancer cell line SkBr-3.

Figure 20A:
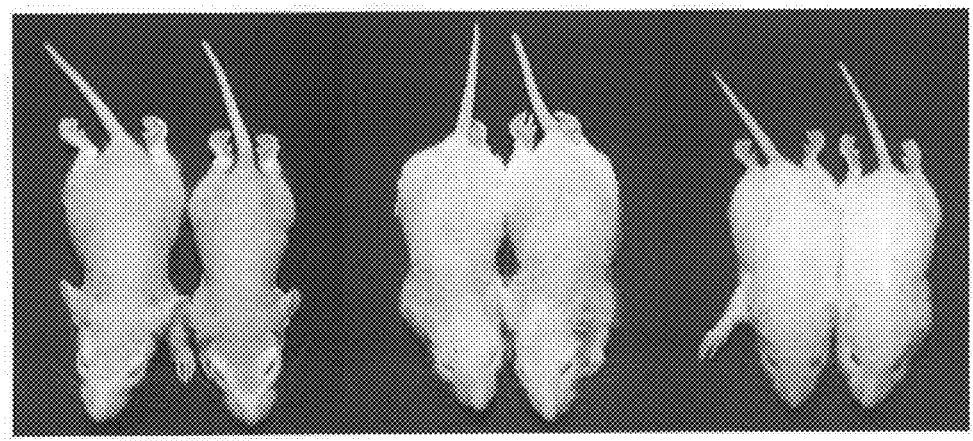
Figure 20B:
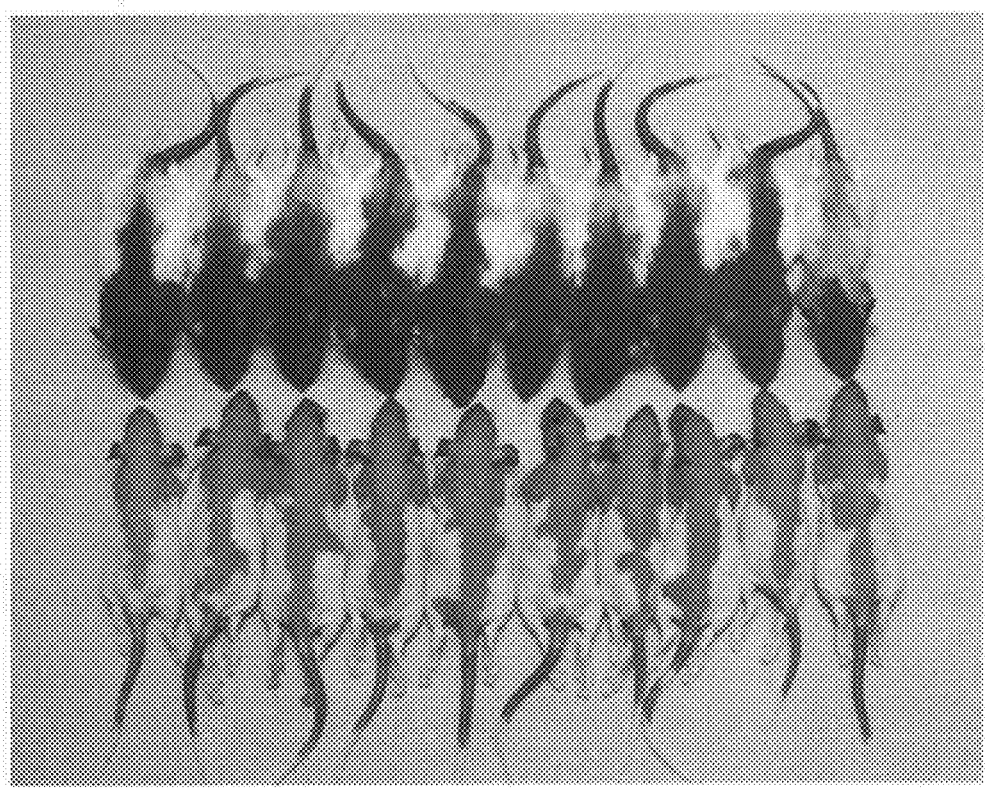

FIG. 20A shows that, in Sprague Dawley rats receiving etoposide, a topical formulation of calcitriol protects from chemotherapy-induced alopecia (CIA) in a dose-dependent manner. Left panel: rats receiving etoposide only; middle panel: rats receiving etoposide and topical application of 0.1 µg of calcitriol in a topical formulation; right panel: rats receiving etoposide and topical application of 0.3 mg of calcitriol in a topical formulation. FIG. 20B shows similar results in the color-coated Long Evans rats.

Figure 21:
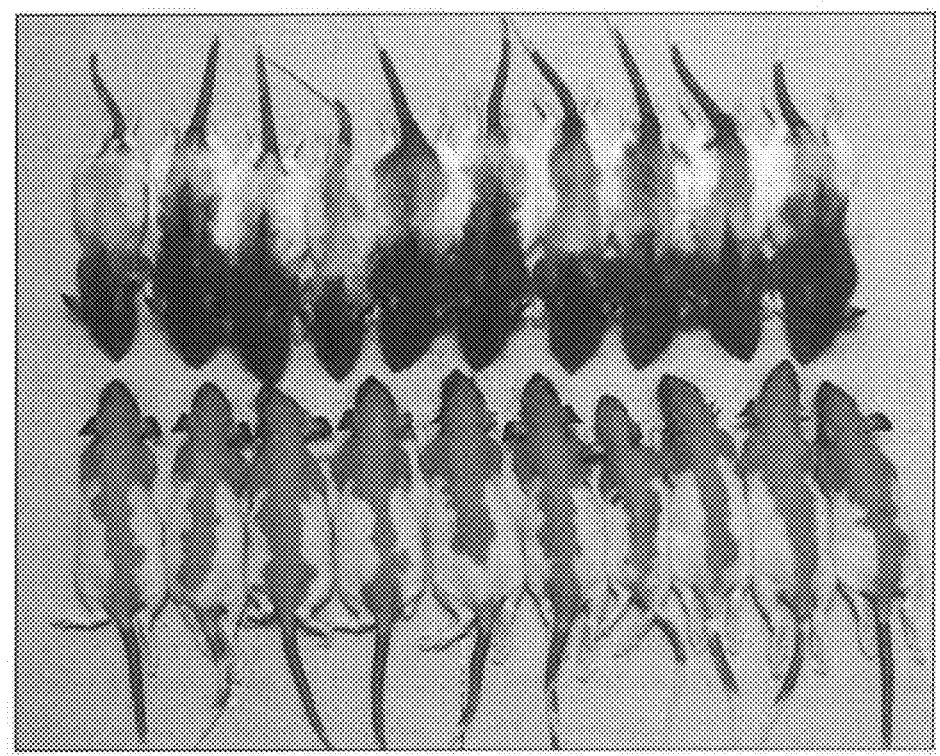

FIG. 21 shows that a calcitriol topical formulation (0.2 µg total dose) protects Long Evans rats from cyclophosphamide (CTX)-induced alopecia.

Figure 22A:
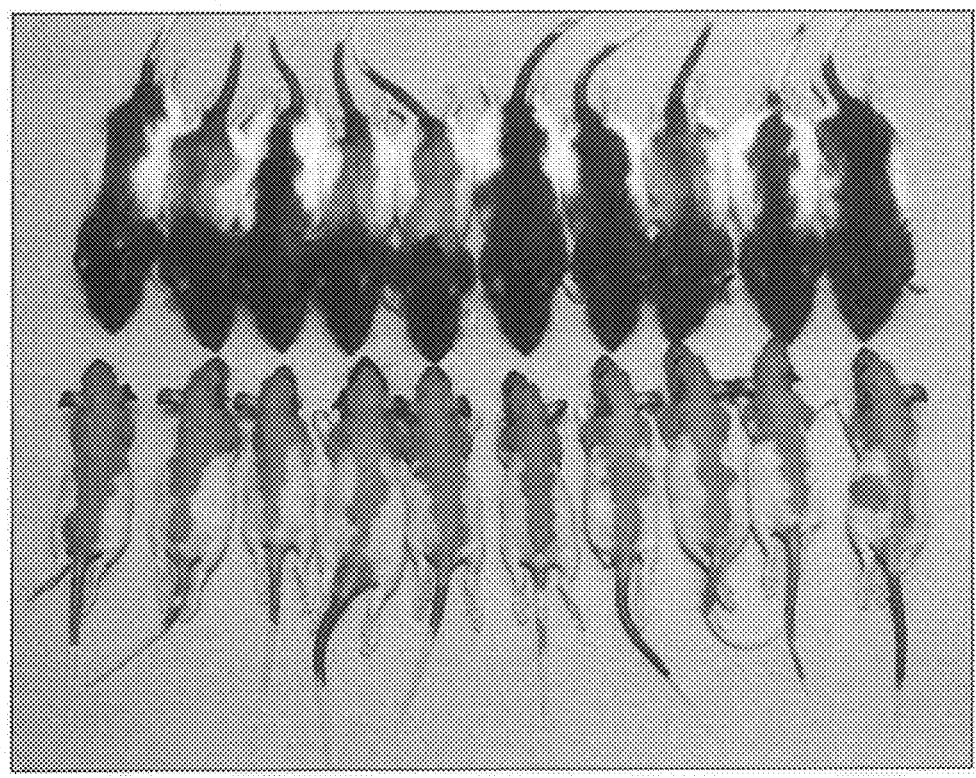
Figure 22B:
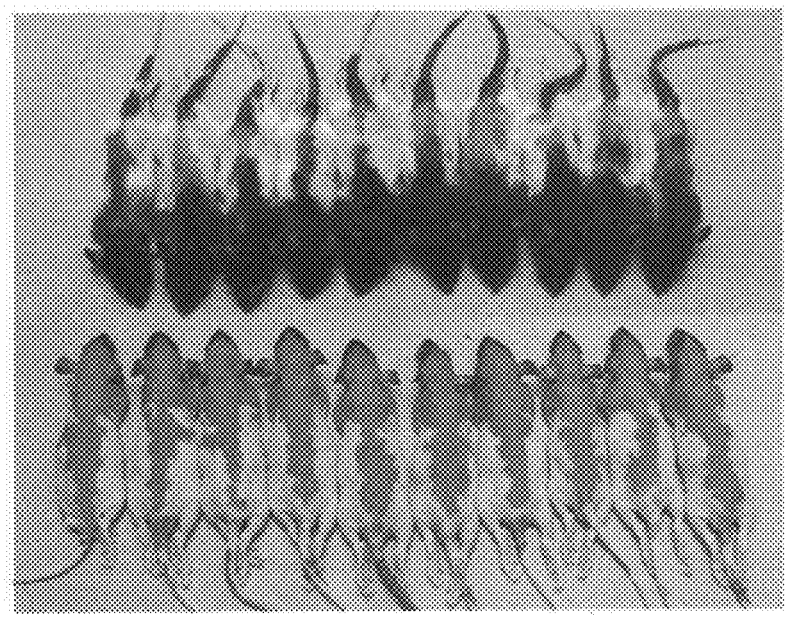

FIG. 22A shows that a calcitriol topical formulation (0.2 µg total dose) protects Long Evans rats from CTX-doxorubicin combination chemotherapy-induced alopecia. FIG. 22B shows similar protective result by a calcitriol topical formulation in rats treated by cytarabine-doxorubicin combination chemotherapy-induced alopecia.

Figure 22C:
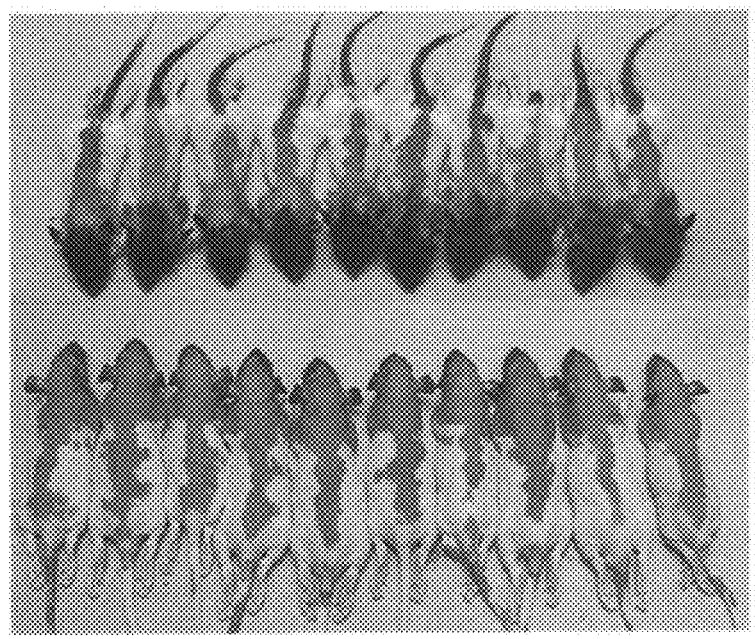

FIG. 22C shows a protective effect of a calcitriol topical formulation on rats treated by cytarabine alone.

Figure 23:
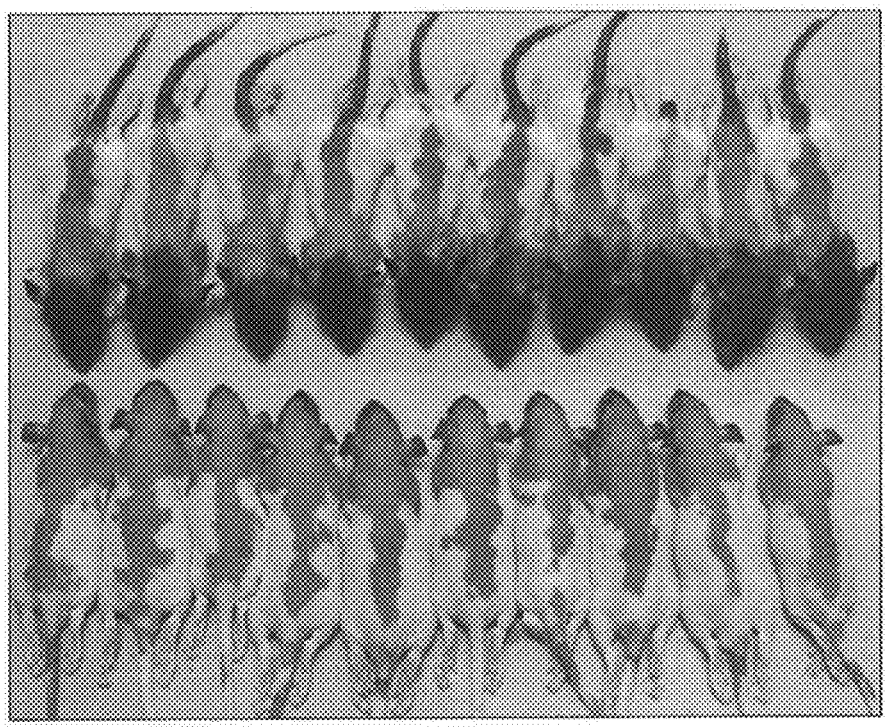

FIG. 23 shows that a topical calcitriol topical formulation (0.2 µg total dose) protects Long Evans rats injected with MIAC51 (chloroleukemia cells) from CTX-induced alopecia.

Figure 24:
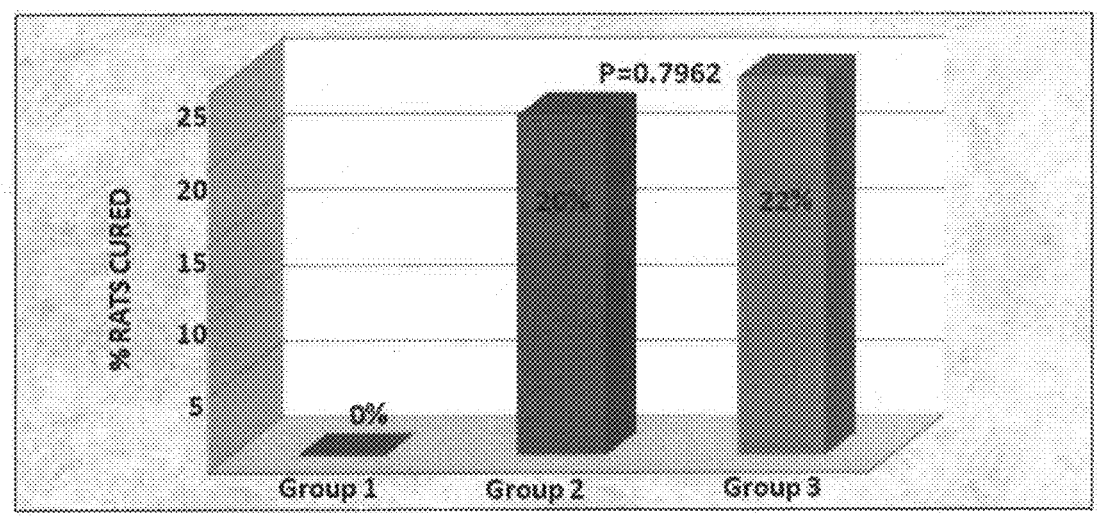

FIG. 24 shows that, in in vivo experiments conducted on Long Evans rats injected with MIAC51 (chloroleukemia cells), a calcitriol topical formulation does not protect the cancer cells from chemotherapy.

Figure 25A:
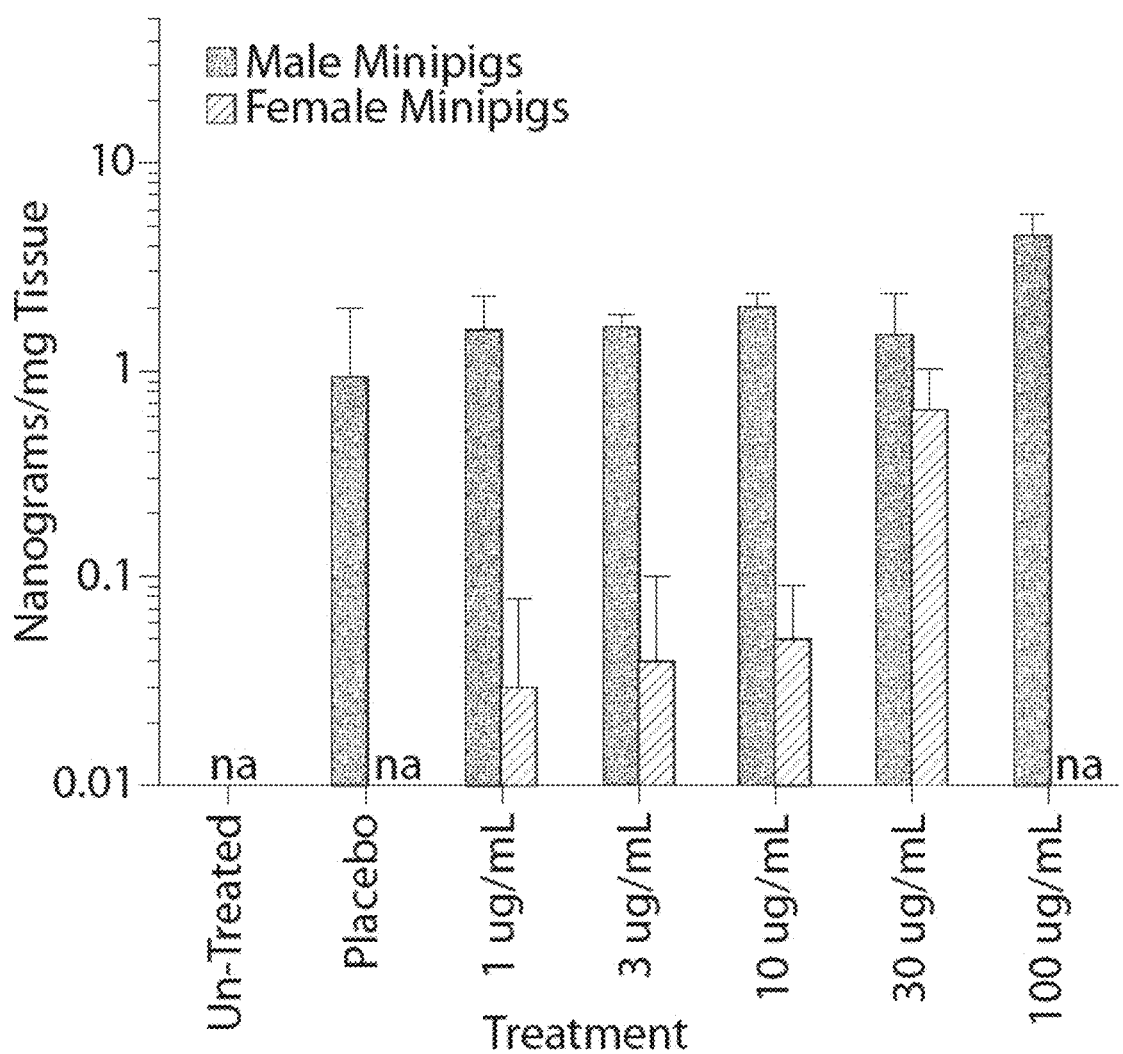
Figure 25B:
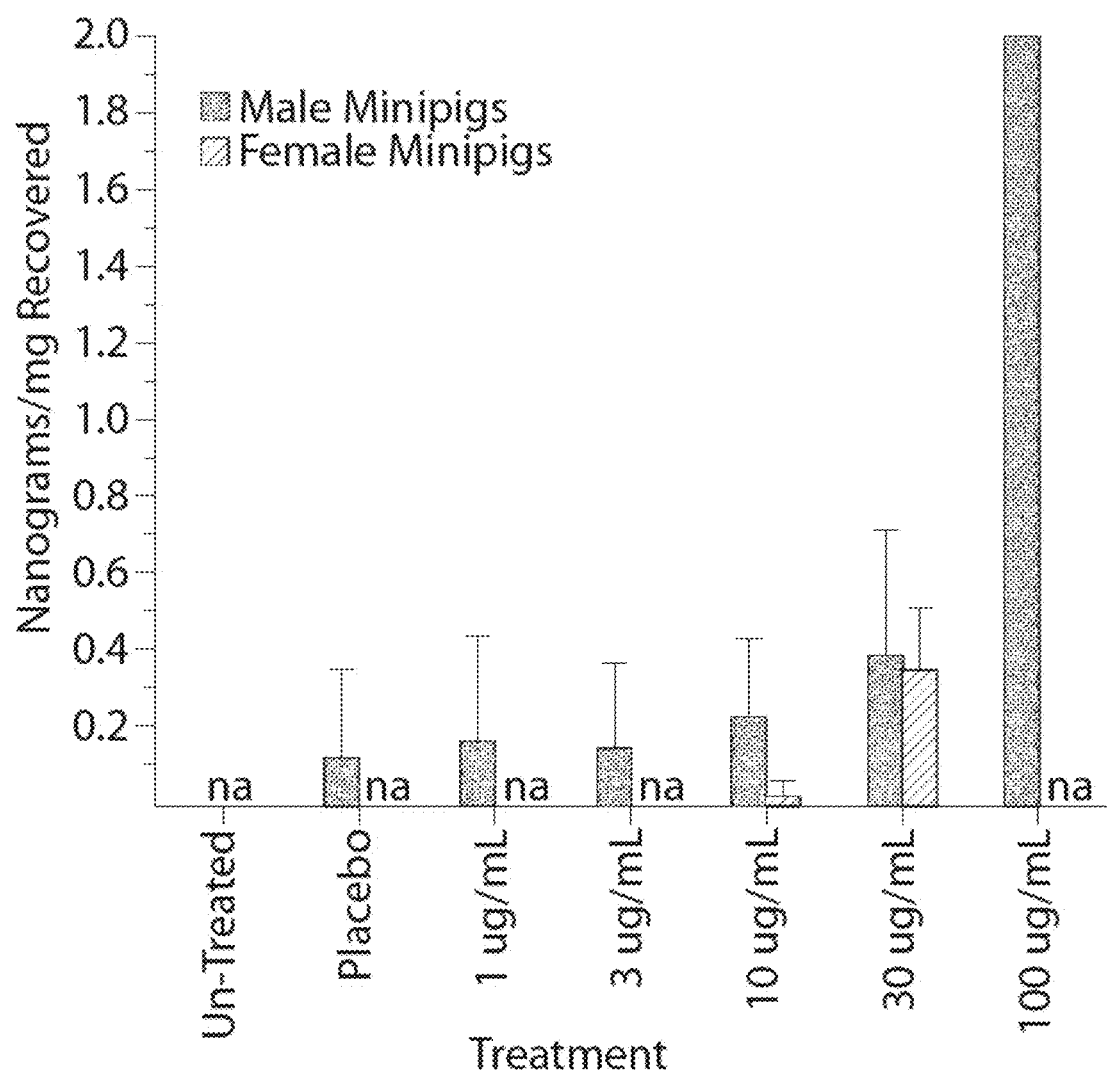

FIGS. 25A and 25B show the estimated level of recovered calcitriol (ng/mg) from the stratum corneum of the minipig epidermis and the rest of the epidermis. The amount is expressed as mean±SD of calcitriol recovered. nd=none detected, na=not available.

Figure 26:
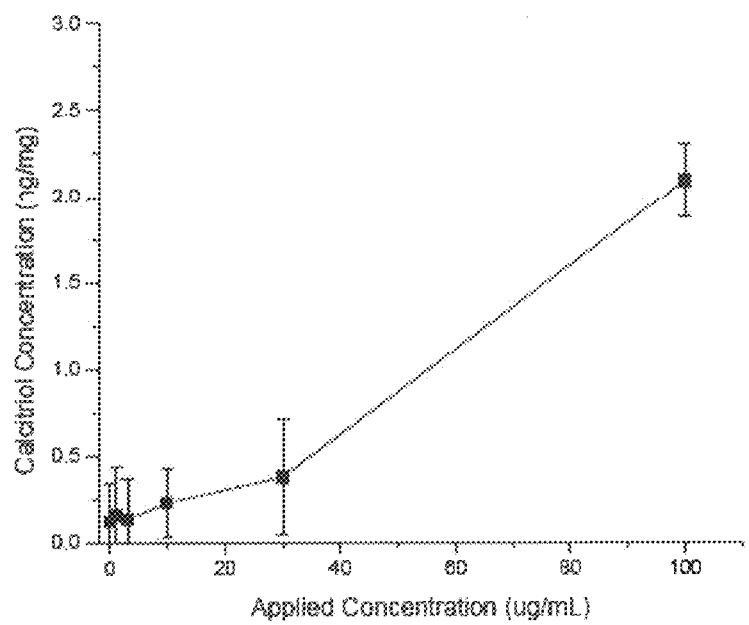

FIG. 26 shows the near linear correlation between calcitriol dose applied to recovered calcitriol tissue level in epidermis, with a range of calcitriol concentrations from 3 to 100 μg/mL applications.

Figures 27A, 27B, 27C:
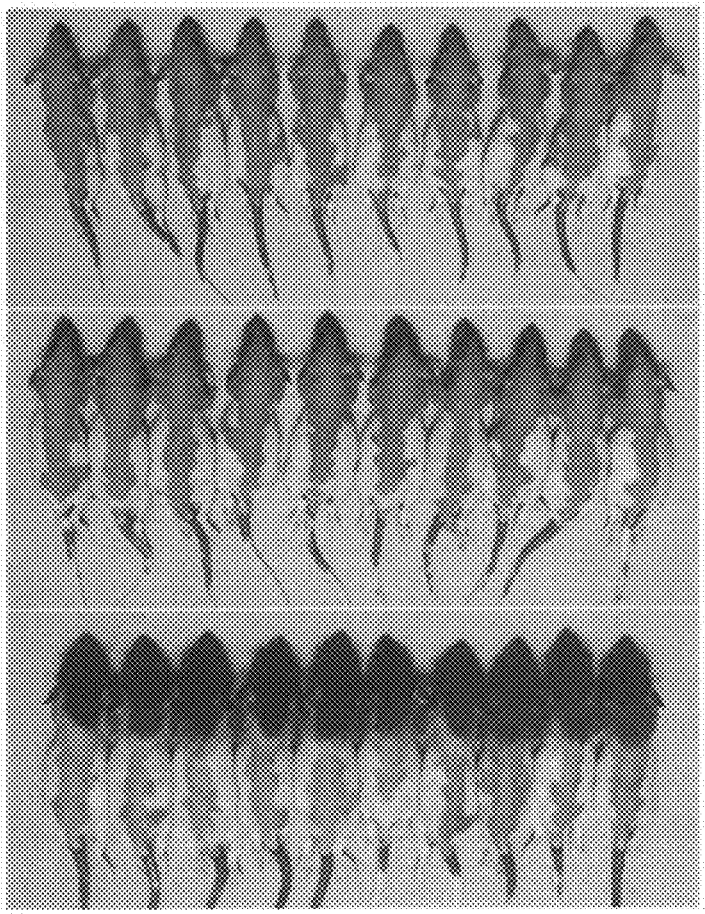

FIGS. 27A, 27B and 27C illustrate the effect of calcitriol on the first anagen course of chloroleukemic rats receiving cyclophosphamide FIG. 27A depicts rats receiving cyclophosphamide alone, FIG. 27B depicts rats receiving cyclophosphamide and vehicle, while FIG. 27C depicts rats receiving cyclophosphamide and calcitriol.

Figure 28:
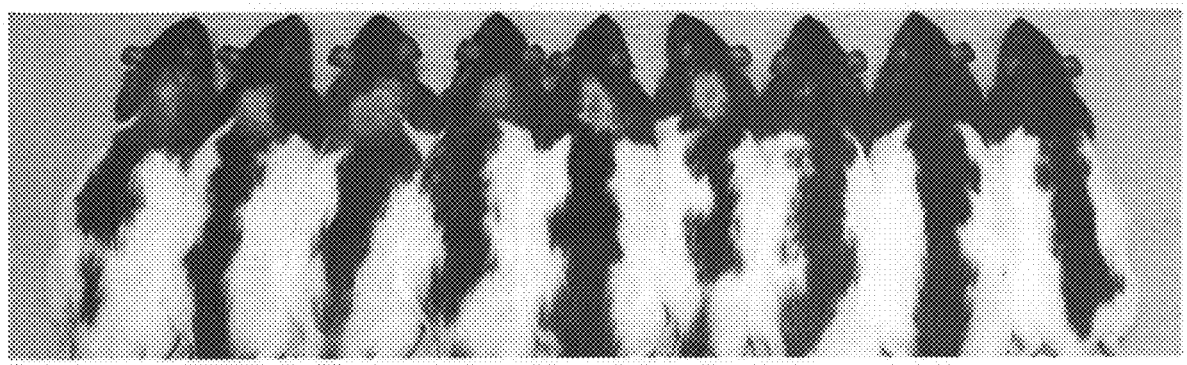

FIG. 28 illustrates the effect of calcitriol on the second anagen course of chloroleukemic rats receiving cyclophosphamide. Left to right, rats treated with cyclophosphamide alone, rats treated with cyclophosphamide and vehicle and rats treated with cyclophosphamide and calcitriol.

Figure 29A:
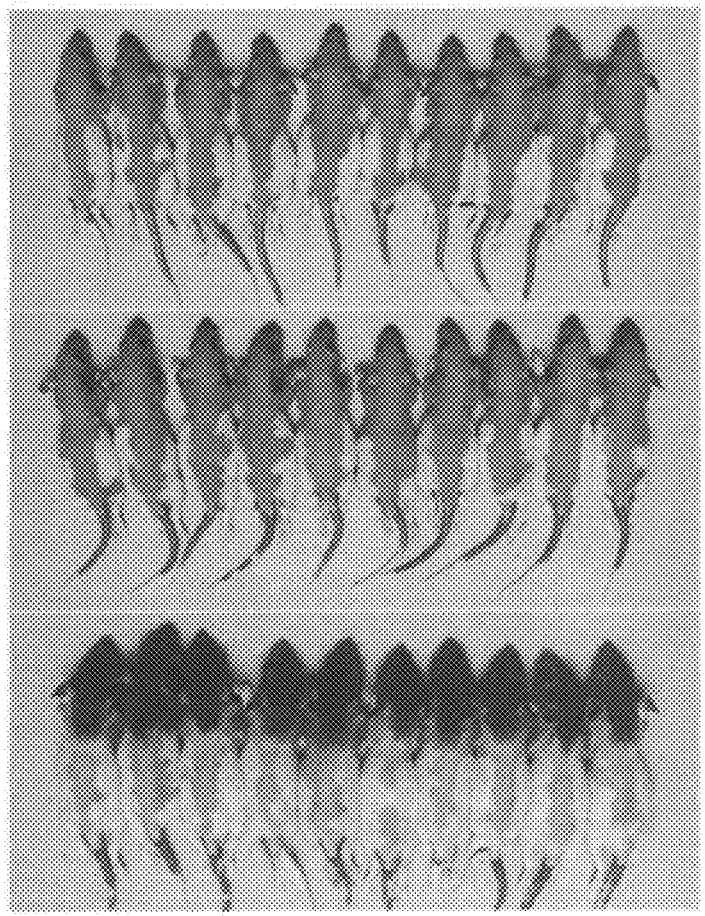
Figure 29B:
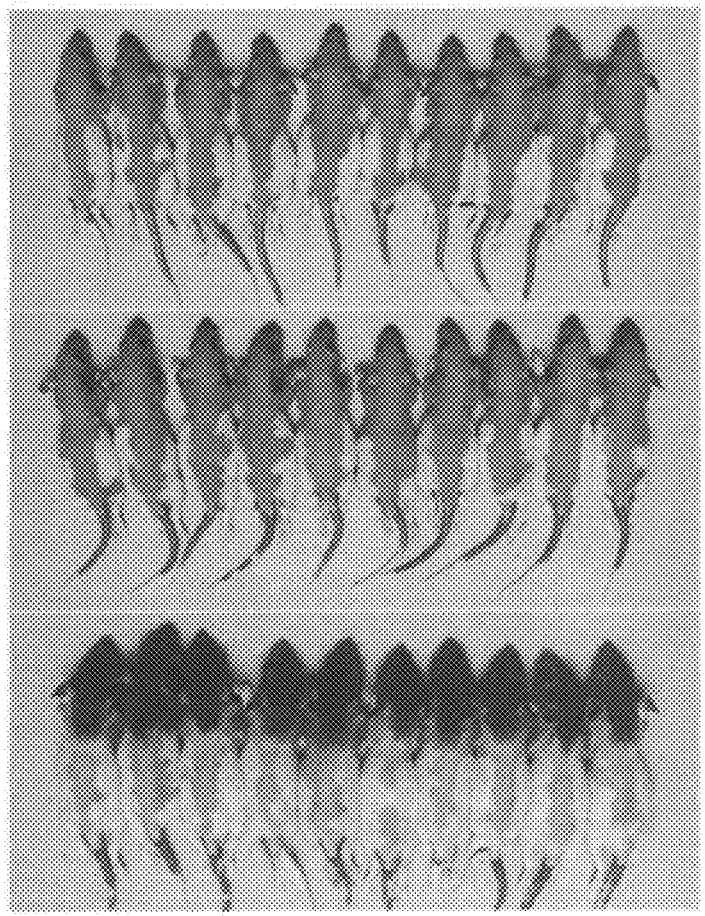
Figure 29C:
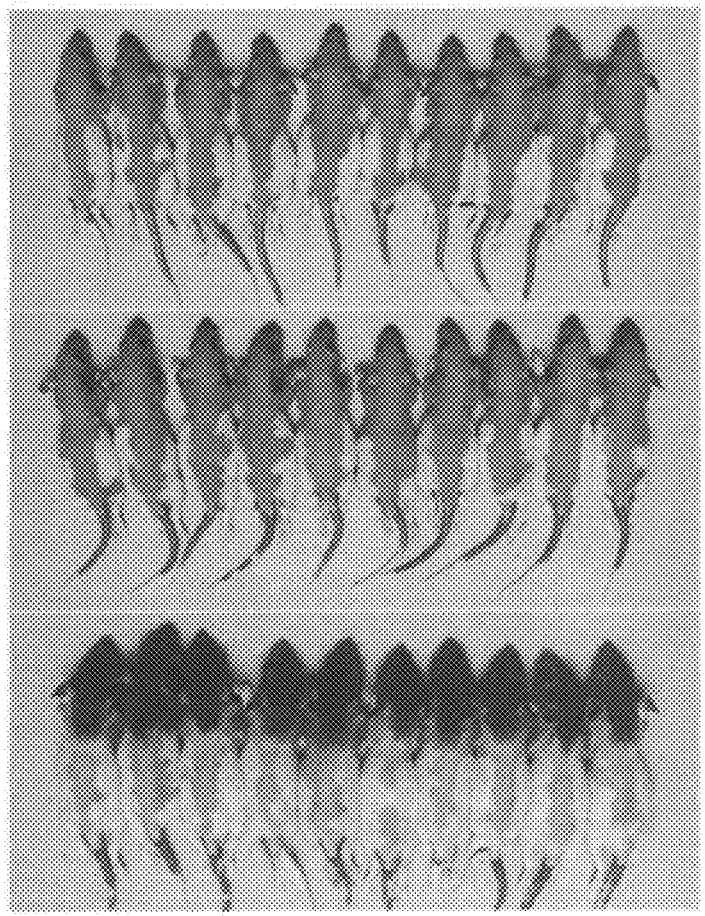

FIGS. 29A, 29B and 29C illustrate the effect of calcitriol on the first anagen course of chloroleukemic rats receiving cyclophosphamide in combination with doxorubicin. FIG. 29A depicts rats receiving cyclophosphamide and doxorubicin alone, FIG. 29B depicts rats receiving cyclophosphamide, doxorubicin and vehicle, while FIG. 29C depicts rats receiving cyclophosphamide, doxorubicin and calcitriol.

Figure 30:
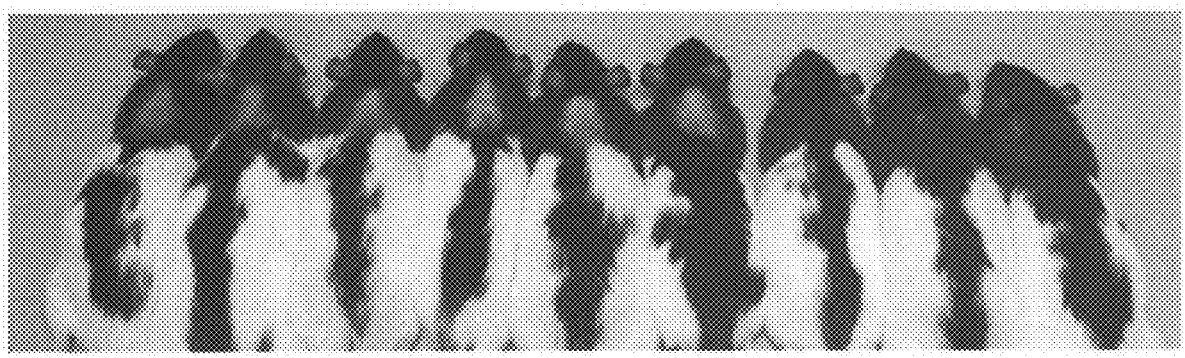

FIG. 30 illustrates the effect of calcitriol on the second anagen course of chloroleukemic rats receiving cyclophosphamide in combination with doxorubicin. Left to right, rats treated with cyclophosphamide and doxorubicin alone, rats treated with cyclophosphamide, doxorubicin and vehicle and rats treated with cyclophosphamide, doxorubicin and calcitriol.

Figures 31A, 31B, 31C:
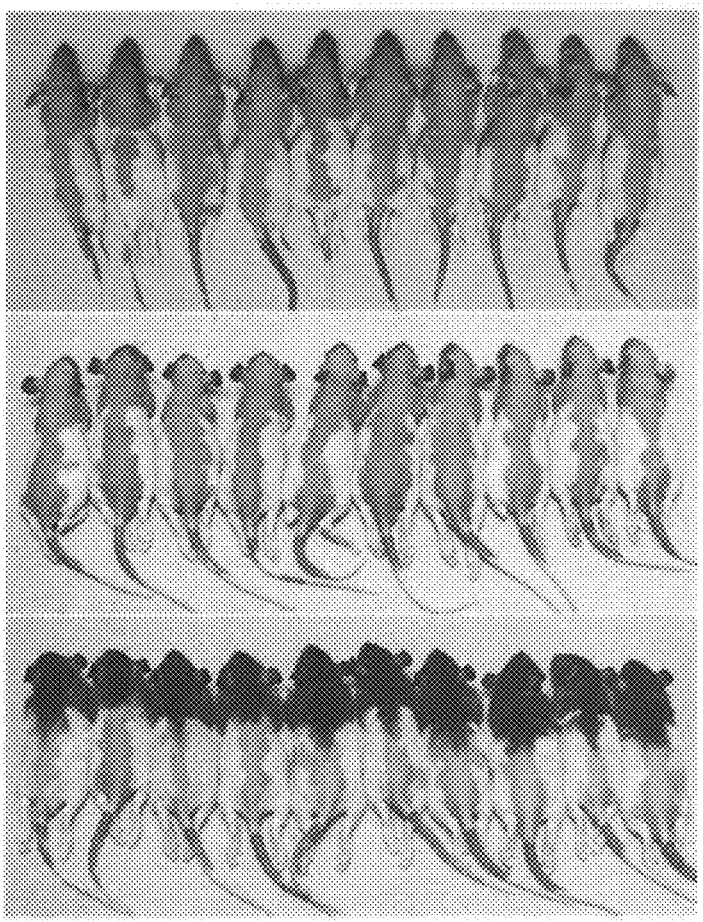

FIGS. 31A, 31B and 31C illustrate the effect of calcitriol on the first anagen course of chloroleukemic rats receiving cyclophosphamide in combination with doxorubicin and cytarabine. FIG. 31A depicts rats receiving cyclophosphamide, doxorubicin and cytarabine alone, FIG. 31B depicts rats receiving cyclophosphoramide, doxorubicin, cytarabine and vehicle, while FIG. 31C depicts rats receiving cyclophosphamide, doxorubicin, cytarabine and calcitriol.

Figure 32:
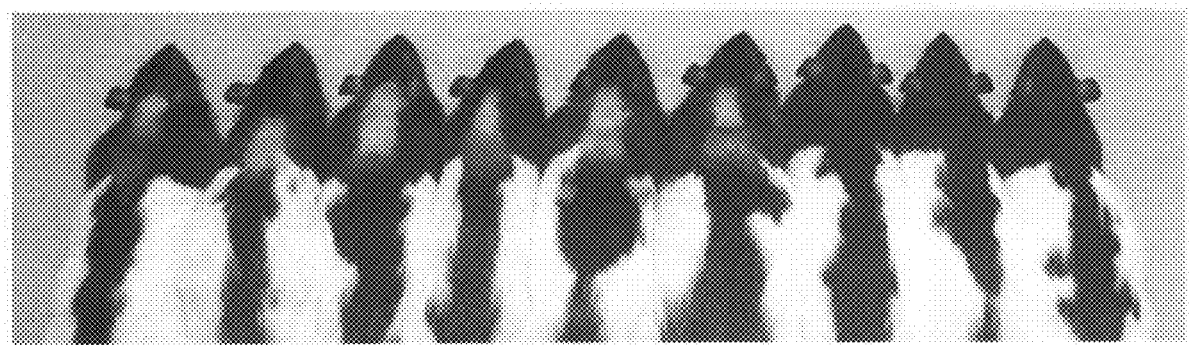

FIG. 32 illustrates the effect of calcitriol on the second anagen course of chloroleukemic rats receiving cyclophosphamide in combination with doxorubicin and cytarabine. Left to right, rats treated with cyclophosphamide, doxorubicin and cytarabine alone, rats treated with cyclophosphamide, doxorubicin, cytarabine and vehicle and rats treated with cyclophosphamide, doxorubicin, cytarabine and calcitriol.

Figures 33A, 33B, 33C:
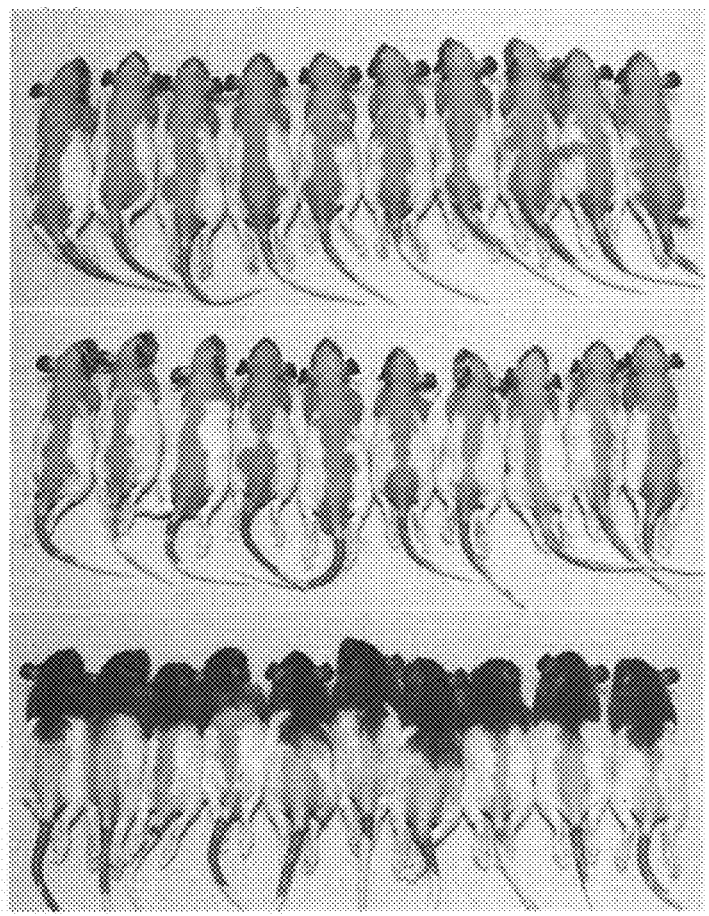

FIGS. 33A, 33B and 33C illustrate the effect of calcitriol on the first anagen course of chloroleukemic rats receiving cyclophosphamide in combination with paclitaxol and etoposide. FIG. 33A depicts rats receiving cyclophosphamide, paclitaxel and etoposide alone, FIG. 33B depicts rats receiving cyclophosphoramide, paclitaxel, etoposide and vehicle, while FIG. 33C depicts rats receiving cyclophosphamide, paclitaxel, etoposide and calcitriol.

Figure 34:
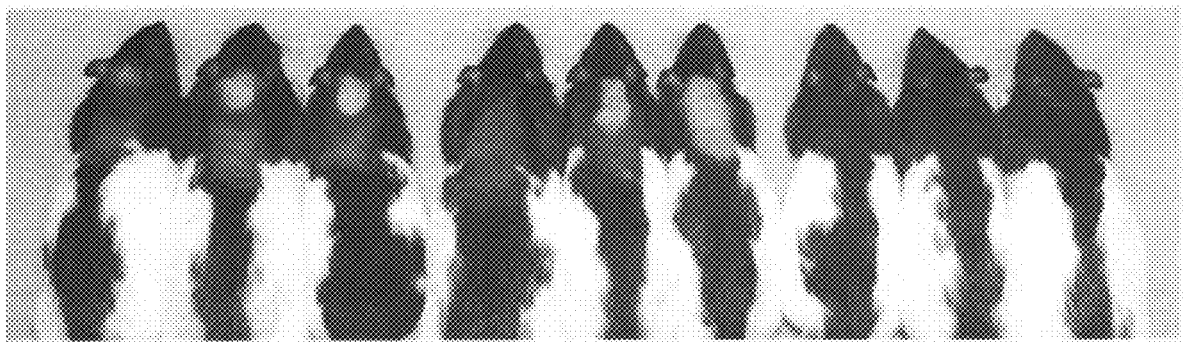

FIG. 34 illustrates the effect of calcitriol on the second anagen course of chloroleukemic rats receiving cyclophosphamide in combination with paclitaxel and etoposide. Left to right, rats treated with cyclophosphamide, paclitaxel and etoposide alone, rats treated with cyclophosphamide, paclitaxel, etoposide and vehicle and rats treated with cyclophosphamide, paclitaxel, etoposide and calcitriol.

Figures 35A, 35B, 35C:
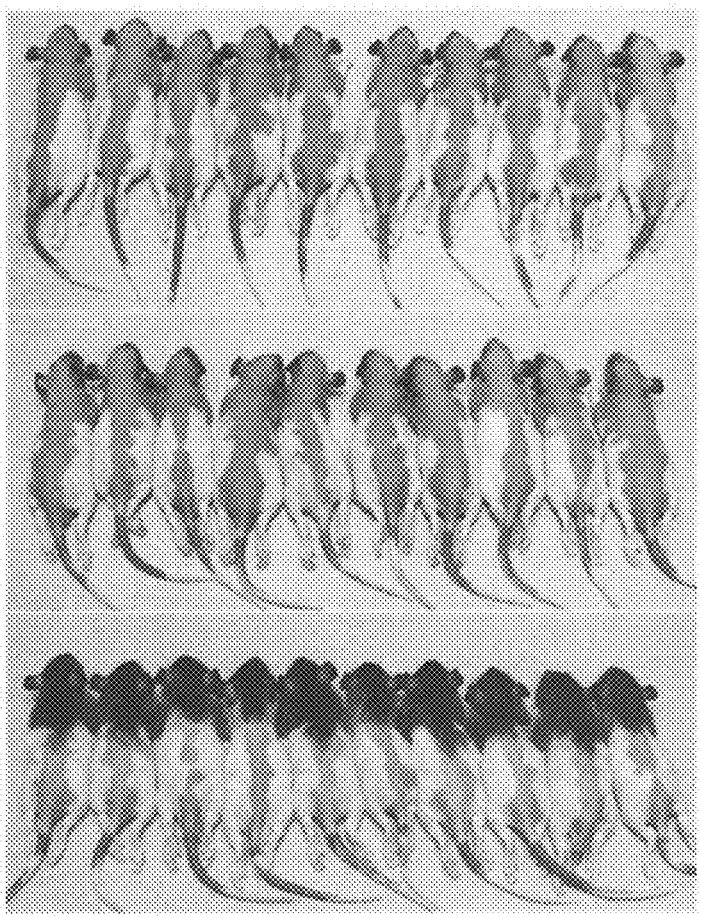

FIGS. 35A, 35B and 35C illustrate the effect of calcitriol on the first anagen course of chloroleukemic rats receiving doxorubicin in combination with paclitaxel and etoposide. FIG. 35A depicts rats receiving doxorubicin, paclitaxel and etoposide alone, FIG. 35B depicts rats receiving doxorubicin, paclitaxel, etoposide and vehicle, while FIG. 35C depicts rats receiving doxorubicin, paclitaxel, etoposide and calcitriol.

Figure 36:
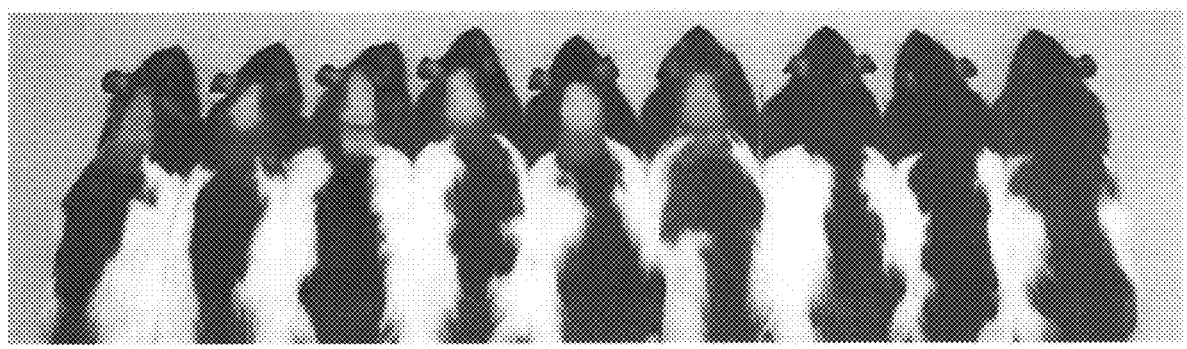

FIG. 36 illustrates the effect of calcitriol on the second anagen course of chloroleukemic rats receiving doxorubicin in combination with paclitaxol and etoposide. Left to right, rats treated with doxorubicin, paclitaxol and etoposide alone, rats treated with doxorubicin, paclitaxol, etoposide and vehicle and rats treated with doxorubicin, paclitaxol, etoposide and calcitriol.

DETAILED DESCRIPTION OF THE INVENTION

The invention described herein is partly based on the discovery that topical formulations of vitamin D compounds that can prevent or treat alopecia (e.g., chemotherapy-induced alopecia) can be selectively delivered to or accumulated in the epidermis layer of the skin while substantially avoiding delivery to and/or accumulation in the deeper dermis layer. This may be advantageous in certain patients undergoing chemotherapy treatment, where deeper accumulation of a vitamin D compound may result in a decrease in the efficacy of the chemotherapy regimen. Such topical formulations may also be advantageous in patients who have medical conditions that may be negatively impacted by the presence of excessive amount of vitamin D compounds, such as patients suffering from kidney stones, and whose condition may worsen upon calcium mobilization by certain vitamin D compounds. Therefore, in such patients, the ideal delivery of the vitamin D compound should be a local delivery of a minimal effective dose to the epidermis layer of the skin, rather than to the dermis layer that is rich in blood vessel.

The invention is also partly based on the discovery that vitamin D compounds exhibit a mild growth stimulatory effect on normal keratinocytes at a relatively low concentration/dosage, while exhibiting a growth inhibitory effect on the same cells at a relatively high concentration/dosage. Thus, the invention provides methods and pharmaceutical compositions that exhibit optimal protective effect against alopecia without causing undesirable growth inhibitory effects.

The invention is further based on the discovery that vitamin D compounds activate or inhibit the expression of multiple target genes in normal keratinocytes, therefore providing a basis to select the most suitable vitamin D compounds for specific therapeutic applications, and to identify additional vitamin D analogs with similar biological activity.

While not wishing to be bound by any particular theory, the formulations of the invention may be advantageous in terms of minimizing drug interference with chemotherapy reagents. The dermal layer of the skin is rich in blood vessels, and topical drug penetration to this layer might cause drug interference with systemically delivered chemotherapeutic reagents, leading to unfavorable protective effects to cancer cells.

Accordingly, in one aspect, the invention provides a method of preventing or treating alopecia in an individual, comprising topically administering to the individual a pharmaceutical composition comprising a therapeutically effective amount of a vitamin D compound formulated to be delivered to and/or accumulated in the epidermis while substantially avoiding dermis delivery and/or accumulation.

The language "substantially avoiding dermis delivery and/or accumulation" includes the delivery and/or accumulation to the dermis of less than about 25% of the vitamin D compound as compared to the delivery and/or accumulation of the vitamin D compound to the epidermis, for example, less than about 20%, less than about 15%, less than about 10%, less than about 5%, less than about 1% or no delivery and/or accumulation of the vitamin D compound to the dermis when compared to the amount delivered to the epidermis. In some embodiments, between about 1% and 25% of the vitamin D compound is delivered and/or accumulated to the dermis, for example, between about 1% and about 20%, between about 1% and about 15%, between about 1% and about 10% or between about 1% and about 5%, as compared to the delivery and/or accumulation to the epidermis. In some embodiments, the vitamin D compound is not delivered and/or accumulated in the dermis. In some embodiments, the amount of vitamin D compound that is delivered to, or accumulates in, the dermis is less than about 0.3 ng/cm$^2$, less than about 0.2 ng/cm$^2$ or less than about 0.1 ng/cm$^2$.

The term "alopecia" includes the involuntary complete or partial hair loss from the head or body of an individual and includes alopecia areata (AA), alopecia totalis (AT), alopecia universalis (AU), or chemotherapy-induced alopecia (CIA). Alopecia areata may include diffuse alopecia areata, alopecia areata monolocularis, alopecia areata *multilocularis*, and alopecia areata barbae. In some embodiments, alopecia does not include androgenetic alopecia (alopecia androgenetica, or male baldness) or post-chemotherapy alopecia (PCA).

Alopecia is the medical description of the loss of hair from the head or body, sometimes to the extent of baldness. Unlike the common aesthetic depilation of body hair, alopecia tends to be involuntary and unwelcome, e.g., androgenic alopecia. However, it may also be caused by a psychological compulsion to pull out one's own hair (trichotillomania) or the unforeseen consequences of voluntary hairstyling routines (mechanical "traction alopecia" from excessively tight ponytails or braids, or burns to the scalp from caustic hair relaxer solutions or hot hair irons). In some cases, alopecia is an indication of an underlying medical concern, such as iron deficiency.

When hair loss occurs in only one section, it is known as "alopecia areata." In human alopecia areata, hair is lost from some or all areas of the body, usually from the scalp. Because it causes bald spots on the scalp, especially in the first stages, it is sometimes called spot baldness. In 1%-2% of cases, the condition can spread to the entire scalp (alopecia totalis) or to the entire epidermis (alopecia universalis).

Conditions resembling AA, and having a similar cause, occur also in other species. The most common type of alopecia areata involves hair loss in one or more round spots on the scalp. Hair may also be lost more diffusely over the whole scalp, in which case the condition is called diffuse alopecia areata. Alopecia areata monolocularis describes baldness in only one spot that may occur anywhere on the head. Alopecia areata *multilocularis* refers to multiple areas of hair loss. The disease may be limited only to the beard, in which case it is called alopecia areata barbae. If the individual loses all the hair on his/her scalp, the disease is then called alopecia areata totalis.

"Alopecia universalis" is when complete hair loss on the body occurs, similar to how hair loss associated with chemotherapy sometimes affects the entire body.

"Androgenic alopecia" (also known as androgenetic alopecia or alopecia androgenetica) is a common form of hair loss in both female and male humans, chimpanzees, and orangutans. In male humans in particular, this condition is also commonly known as male pattern baldness. Hair is lost in a well-defined pattern, beginning above both temples. Over time, the hairline recedes to form a characteristic "M" shape. Hair also thins at the crown of the head. Often a rim of hair around the sides and rear of the head is left, or the condition may progress to complete baldness. The pattern of hair loss in women differs from male pattern baldness. In women, the hair becomes thinner all over the head, and the hairline does not recede. Androgenic alopecia in women rarely leads to total baldness.

The language "preventing alopecia" includes the arresting of or suppression of hair loss associated with alopecia prior to its occurrence.

The language "treating alopecia" includes reducing the severity of the hair loss associated with alopecia or reducing the extent of the hair loss associated with of alopecia. In some embodiments, treating alopecia includes the amelioration of alopecia.

The term "administering" includes providing one or more doses of the vitamin D compound to the individual in an amount effective to prevent or treat alopecia. Optimal administration rates for a given protocol of administration of the vitamin D compound can ascertained by those skilled in the art using conventional dosage determination tests conducted with regard to the specific compounds being utilized, the particular compositions formulated, the mode of application, the particular site of administration and the like.

The language "topically administering" includes delivering one or more doses of the vitamin D compound to the skin of the individual in an amount effective to treat or prevent alopecia.

The skin contains many specialized cells and structures, and has various important functions, such as serving as a protective barrier that interfaces with the environment, helping to maintain the proper body temperature, gathering sensory information from the environment, and playing an active role in the immune system.

The skin has three layers—the epidermis, dermis, and subcutaneous tissue. The epidermis is the outer layer of skin. Its thickness varies in different types of skin. It is the thinnest on the eyelids at about 0.05 mm and the thickest on the palms and soles at about 1.5 mm. From bottom to top, the epidermis contains five layers: stratum basale, stratum *spinosum*, stratum *granulosum*, stratum licidum (optional in some skins), and stratum corneum.

The stratum basale is the bottom layer of keratinocytes in the epidermis and is responsible for constantly renewing epidermal cells. This layer contains just one row of undifferentiated columnar stem cells that divide very frequently. Half of the cells differentiate and move to the next layer to begin the maturation process. The other half stay in the basal layer and divide repeatedly to replenish the basal layer. Cells that move into the *spinosum* layer (also called prickle cell layer) change from being columnar to polygonal. In this layer, the cells start to synthesize keratin. The cells in the stratum *granulosum*, or granular layer, have lost their nuclei and are characterized by dark clumps of cytoplasmic material. There is a lot of activity in this layer as keratin proteins and water-proofing lipids are being produced and organized. The stratum lucidum layer is only present in thick skin where it helps reduce friction and shear forces between the stratum corneum and stratum *granulosum*. The cells in the stratum corneum layer are known as corneocytes. These cells have flattened out and are composed mainly of keratin protein which provides strength to the layer but also allows the absorption of water. The structure of the stratum corneum layer looks simple, but this layer is responsible for maintaining the integrity and hydration of the skin—a very important function.

The dermis also varies in thickness depending on the location of the skin. It is about 0.3 mm on the eyelid and about 3.0 mm on the back. The dermis is composed of three types of tissue that are present throughout—not in layers: collagen, elastic tissue, and reticular fibers. The two layers of the dermis are the papillary and reticular layers. The upper, papillary layer, contains a thin arrangement of collagen fibers. The lower, reticular layer, is thicker and made of thick collagen fibers that are arranged parallel to the surface of the skin. The dermis contains many specialized cells and structures. For example, blood vessels and nerves course through this layer. The hair follicles are also situated in this layer with the erector pili muscle that attaches to each follicle. A portion of the hair follicle also contains stem cells capable of regrowing damaged epidermis. Stem cells may be present at the dermal-epidermal junction (DEJ). Sebaceous (oil) glands and apocrine (scent) glands are associated with the follicle. This layer also contains eccrine (sweat) glands, but they are not associated with hair follicles. The subcutaneous tissue is a layer of fat and connective tissue that houses larger blood vessels and nerves. This layer is important in the regulation of temperature of the skin itself and the body. The size of this layer varies throughout the body and from person to person.

Accordingly, as used herein, "epidermis" includes all five of its layers (when present), including the junction layer between epidermis and dermis (e.g., dermal-epidermal junction or DEJ), and stem cells that regenerates the epidermal layers (e.g., follicular stem cells and epidermal stem cells).

In some embodiments, the vitamin D compound is topically delivered to and/or accumulated in the epidermis while substantially avoiding delivery and/or accumulation in the dermis. As used herein, the language "substantially avoiding dermis delivery and/or accumulation" includes no more than about 20%, about 15%, about 10%, about 5% or about 0% delivery to/accumulation of the vitamin D compound in the dermis. In a preferred embodiment, there is no detectable delivery/accumulation of the vitamin D compound to the dermis.

In certain embodiments, the vitamin D compounds of the invention is administered to the individual over a period of about 1 day, about 2 days, about 3 days, about 4 days, about 5 days, about 6 days, about 7 days, about 8 days, about 9 days, about 10 days, about 11 days, about 12 days, about 13 days, about 2 weeks, about 3 weeks, about 4 weeks, about 6 weeks, 8 about weeks, about 3 months, about 4 months, about 5 months, about 6 months, about 7 months, about 8 months, about 9 months, about 10 months, about 11 months or about a year. In some embodiments, the vitamin D compounds of the invention may be administered every day during the treatment period, on alternative days, or once every three days.

In certain embodiments, the vitamin D compounds of the invention are administered once daily, twice daily, or three times daily in each treatment day.

In certain embodiments, each administration of the vitamin D compounds of the invention is applied to the same location, or to several different locations on the individual. When applied to different locations, the doses for each location may be the same, or be adjusted based on factors such as skin thickness and differences in drug penetration (if any).

In certain embodiments, the vitamin D compounds of the invention is topically administered to the scalp twice daily each day for two consecutive weeks prior to the commencement of chemotherapy in order to prevention or reduce the severity of any CIA that may occur upon commencement of chemotherapy.

The term "individual" includes those animals that have the ability to suffer from alopecia. In one embodiment, the individual is a mammal, for example, cats, dogs, primates, mice, rats, rabbits, cattle, horses, goats, sheep, pigs, etc. In some embodiments, the mammal is a primate, for example, chimpanzees, humans, gorillas, bonobos, orangutans, monkeys, etc. In yet another embodiments, the mammal is a human.

In some embodiments, the individual is undergoing or about to undergo chemotherapy treatment. In one embodiment, the individual has not yet developed symptoms of alopecia or the alopecia has not commenced prior to administration. In some other embodiments, the individual is suffering from cancer.

In another aspect, the invention provides methods of preventing or treating alopecia in an individual by topically administering to the individual a pharmaceutical composition comprising a therapeutically effective amount of a vitamin D compound for preventing or treating alopecia in said individual, without substantially interfering with or reducing the efficacy of a co-administered chemotherapeutic agent.

In some embodiments, the methods and pharmaceutical compositions of the invention do not substantially reduce the efficacy of chemotherapy, especially systemic chemotherapy. In other embodiments, the methods and pharmaceutical compositions of the invention enhances the efficacy of chemotherapy. The language "without interfering with the efficacy of a co-administered chemotherapeutic agent" includes the situation where the vitamin D compound, when administered with one or more chemotherapeutic agents, does not interrupt the biological or therapeutic activity of the one or more chemotherapeutic agents or prevent the one or more chemotherapeutic agents from performing its desired biological or therapeutic activity. The language "without reducing the efficacy of a co-administered chemotherapeutic agent" includes the situation where the vitamin D compound, when administered with one or more chemotherapeutic agents, does not decrease the biological or therapeutic activity of the one or more chemotherapeutic agents.

The methods and pharmaceutical compositions of the invention may be used with any chemotherapeutic agent or combination of chemotherapeutic agents that have a cytotoxic effect on the hair follicle or dermal papilla, or is otherwise capable of inducing alopecia. The language "chemotherapeutic agent," "chemotherapy," and "chemotherapeutic regimen" include Anthracyclines (Adriamycin/Doxorubicin, Daunorubicin, Epirubicin, Idarubicin, Valrubicin), 5-FU, Tamoxifen, Irinotecan, Paclitaxel (Taxol), Carboplatin, Etoposide, Cytoxan/Cyclophosphamide, Cisplatin, Erlotinib (Tarceva), bevacizumab, Gemcitabine, Staurosporin, Vincristine, Imatinib (Gleevec), Gefitinib (Iressa), Sorafenib, Dasatinib, Dactinomycin, Hexamethamelamine (HMM, altretamine), Ifosfamide, bleomycin, methotrexate, Docetaxel (Taxotere), Vindesine, Vinorelbine, Topotecan, Amsacrine, Cytarabine, Busulphan, Melphalan, Vinblastine, Lomustine (CCNU), Thiotepa, Gemcitabine, Carmustine (BCNU), Mitroxantrone, Mitomycin C, Procarbazine, 6-Mercaptopurine, Sreptozotocin, Fludarabine, Raltitrexate (Tomudex), Capecitabine, and equivalents thereof.

In some embodiments, the chemotherapy is systemic chemotherapy.

The methods and pharmaceutical compositions of the invention preferably does not substantially reduce the efficacy of chemotherapy, especially systemic chemotherapy. Preferably, the methods and pharmaceutical compositions of the invention enhances the efficacy of chemotherapy.

The methods and pharmaceutical compositions of the invention may also be used with any hormone therapies or biological therapies that can cause hair thinning.

In some embodiments, the vitamin D compound is co-administered with a chemotherapeutic agent. The language "co-administered with a chemotherapeutic agent" includes administration of the vitamin D compound at substantially the same time as the chemotherapeutic agent. For example, the vitamin D compound may be co-administered with the chemotherapeutic agent; the vitamin D compound may be administered first, and immediately followed by the administration of the chemotherapeutic agent or the chemotherapeutic agent may be administered first, and immediately followed by the administration of the vitamin D compound.

In some other embodiments, the vitamin D compound is administered to the individual prior to the occurrence of alopecia (e.g., prior to the loss of hair). In certain embodiments, the vitamin D compound is administered to the individual after the commencement of chemotherapy, but prior to the commencement of alopecia. In other embodiments, the individual has not already developed symptoms of alopecia (e.g., alopecia has not commenced). The vitamin D compound may be administered to the individual either prior to chemotherapy, or concurrent with the chemotherapy.

The language "therapeutically effective amount" includes that amount of a vitamin D compound necessary or sufficient to prevent or treat alopecia in an individual. The effective amount can vary depending on such factors as the size and weight of the subject, the type of illness, etc. One of ordinary skill in the art would be able to study the aforementioned factors and make the determination regarding the effective amount of the vitamin D compound without undue experimentation.

The vitamin D compounds of the invention may be topically administered to an individual in need thereof at a dosage volume equivalent to about 0.001 µg-5 µg of calcitriol/cm$^2$. In certain embodiments, the range is about 0.01 µg-0.5 µg of calcitriol/cm$^2$, or about 0.1 µg-0.5 µg of calcitriol/cm$^2$.

The language "dosage volume equivalent to calcitriol" includes that amount of vitamin D compound that has substantially similar biological and/or therapeutic activity as the biological and/or therapeutic activity as 0.001 µg-5 µg calcitriol/cm$^2$.

The language "effective concentration" includes the concentration of the vitamin D compound in a topical formulation that is necessary or sufficient to prevent or treat alopecia in an individual. In certain embodiments, the concentration of the vitamin D compound in the topical formulation is about 0.1, 0.2, 0.5, 1.0, 2, 3, 5, 10, 20, 30, 50, 75, 100, 150, 200, or 400 µg/mL.

In certain embodiments, the total dose of the vitamin D compound is equivalent to about 0.025-400 µg of calcitriol/75 kg body weight. In certain embodiments, the range is about 0.1-100 µg of calcitriol/75 kg body weight; about 0.4-25 µg of calcitriol/75 kg body weight; or about 1, 2, 3, 5, or 10 µg of calcitriol/75 kg body weight. In certain embodiments, the lower range of the total dose is equivalent to about 0.025, 0.05, 0.1, 0.2, 0.5, 1, or 2 µg of calcitriol/75 kg body weight. In certain embodiments, the high range of the total dose is equivalent to about 400, 200, 100, 50, 25, 10, 5, 2, or 1 µg of calcitriol/75 kg body weight.

In still another aspect, the invention provides methods of preventing or treating alopecia in an individual by topically administering to the individual a pharmaceutical composition comprising a therapeutically effective amount of a vitamin D compound, wherein said vitamin D compound, when topically administered to the individual at an effective concentration of: (1) about 50 µg/mL, does not cause toxicity after at least about 25 consecutive days of drug administration; or (2) about 100 µg/mL, does not cause toxicity after at least about 7 consecutive days of drug administration.

Possible toxic side effects caused by the administration of a vitamin D compound, may include, for example, hypercalcemia, which has symptoms including anorexia, bone pain, tiredness, vomiting, diarrhea, constipation, polyurea, pruritus, renal failure, a metallic taste in the mouth, preoteinurea, urinary casts, azoteri or metastatic calcification.

In some embodiments, the vitamin D compound is formulated to be delivered to/accumulated in human epidermis, especially epidermis of the scalp or neck region, while substantially avoiding delivery to/accumulation in the dermis. One of skill in the art would readily be able to determine the amount of the vitamin D compound, or lack thereof, delivered to/accumulated in the dermis and/or the epidermis using Example 1.

The language "vitamin D compound" includes compounds of Formula I:

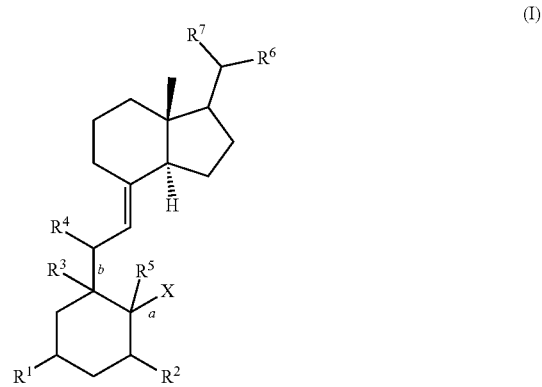

(I)

wherein a and b are each independently a single or double bond;

X is —CH$_2$ when a is a double bond, or X is hydrogen or a hydroxyl substituted alkyl when a is a single bond;

R$^1$ is hydrogen, hydroxyl, alkoxyl, tri-alkyl silyl or alkyl, optionally substituted with one to three halogen, hydroxyl, cyano or —NR'R" moieties;

R$^2$ is hydrogen, hydroxyl, —O-trialkyl silyl, or alkyl, alkoxyl or alkenyl, optionally substituted with one to three halogen, hydroxyl, cyano or —NR'R" moieties;

R$^3$ is absent when b is a double bond or R$^3$ is hydrogen, hydroxyl or alkyl, or R$^3$ and R$^1$ together with the carbon atoms to which they are attached may be linked to form 5-7 membered carbocyclic ring when b is a single bond;

R$^4$ is absent when b is a double bond or hydrogen, halogen or hydroxyl when b is a single bond;

R$^5$ is absent when a is a double bond or R$^5$ is hydrogen, halogen or hydroxyl when a is a single bond;

R$^6$ is alkyl, alkenyl, alkynyl, cycloalkyl, heterocyclicyl, alkyl-O-alkyl, alkyl CO$_2$-alkyl optionally substituted with one to five, hydroxyl, oxo, halogen, alkoxyl, aryl, heteroaryl, cyano, nitro or —NR'R" moieties;

R$^7$ is alkyl optionally substituted with one to three hydroxyl, halogen, alkoxyl, aryl, heteroaryl, cyano, nitro or —NR'R" moieties; and, R' and R" are each, independently, hydrogen, hydroxyl, halogen, alkyl or alkoxyl, and pharmaceutically acceptable salts thereof.

In some embodiments, R$^1$ is hydroxyl, R$^2$ is hydrogen or hydroxyl, a is a double bond, R$^5$ is absent, X is —CH$_2$, b is a double bond, R$^3$ and R$^4$ are absent, R$^6$ is alkyl (e.g., methyl), and R$^7$ is alkyl (e.g., a substituted or unsubstituted alkyl, for example, a hydroxyl substituted alkyl or a cycloalkyl substituted alkyl, such as —(CH$_2$)$_3$CH(CH$_3$)$_2$ or —(CH$_2$)$_3$COH(CH$_3$)$_2$) or alkenyl (e.g., —CH═CHCH(CH$_3$)CH(CH$_3$)$_2$).

In certain embodiments, the vitamin D compound is represented by Formula (II):

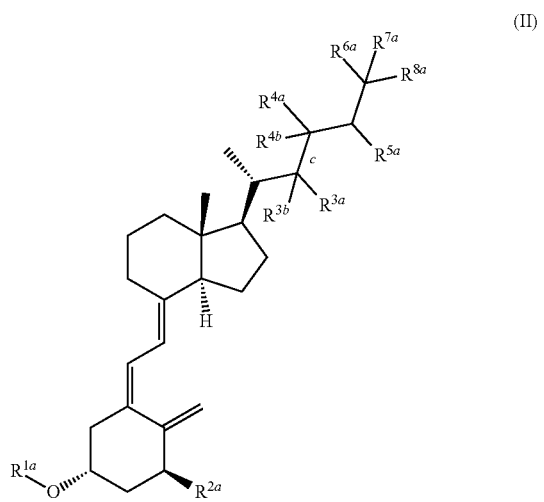

(II)

wherein c is a single or double bond;

R$^{1a}$ is hydrogen, tri-alkyl silyl or alkyl, optionally substituted with one to three halogen, hydroxyl, cyano or —NR'R" moieties;

R$^{2a}$ is hydrogen, hydroxyl, —O-trialkyl silyl, or alkyl, alkoxyl or alkenyl, optionally substituted with one to three halogen, hydroxyl, cyano or —NR'R" moieties;

R$^{3a}$ and R$^{4a}$ are absent when c is a double bond, or are each independently hydrogen, hydroxyl, halogen, alkoxyl or alkyl optionally substituted with one to three hydroxyl or halogen moieties when c is a single bond R$^{3b}$, R$^{4b}$, R$^{5a}$, R$^{6a}$, R$^{7a}$ and R$^{8a}$ are each, independently, hydrogen, hydroxyl, halogen, alkoxyl or alkyl optionally substituted with one to three hydroxyl or halogen moieties, or any two of R$^{6a}$, R$^{7a}$ and R$^{8a}$ may be linked to form a 3-7 membered carbocyclic ring, and pharmaceutically acceptable salts thereof.

In an embodiment, the compound is represented by Formula (II), wherein R$^{1a}$, R$^{3a}$ and R$^{4a}$ are each hydrogen.

In another embodiment, the compound is represented by Formula (II), wherein c represents a single bond.

In yet another embodiment, the compound is represented by Formula (II), wherein R$^{6a}$ and R$^{8a}$ are both methyl.

In one embodiment, the compound is represented by Formula (II), wherein R$^{1a}$ is hydrogen.

In another embodiment, the compound is represented by Formula (II), wherein R$^{2a}$ is hydroxyl.

In another embodiment, the compound is represented by Formula (II), wherein R$^{7a}$ is hydroxyl.

In yet another embodiment, the compound is represented by Formula (II), wherein R$^{5a}$ is hydroxyl.

In one embodiment, R$^{1a}$ is hydrogen, R$^{2a}$ is hydrogen or hydroxyl, c is a single bond, R$^{3a}$, R$^{3b}$, R$^{4a}$, R$^{4b}$ and R$^{5a}$ are each hydrogen, R$^{6a}$ and R$^{7a}$ are each alkyl (e.g., methyl) and R$^{8a}$ is hydrogen or hydroxyl.

In another embodiment, R$^{1a}$ is hydrogen, R$^{2a}$ is hydrogen or hydroxyl, c is a double bond, R$^{3a}$ and R$^{4a}$ are absent, R$^{3b}$ and R$^{4b}$ are hydrogen, R$^{5a}$ is alkyl (e.g., methyl), R$^{6a}$ and R$^{7a}$ are each alkyl (e.g., methyl) and R$^{8a}$ is hydrogen or hydroxyl.

In one embodiment, the vitamin D compound is selected from the following structures, or stereoisomers or pharmaceutically acceptable salts thereof:

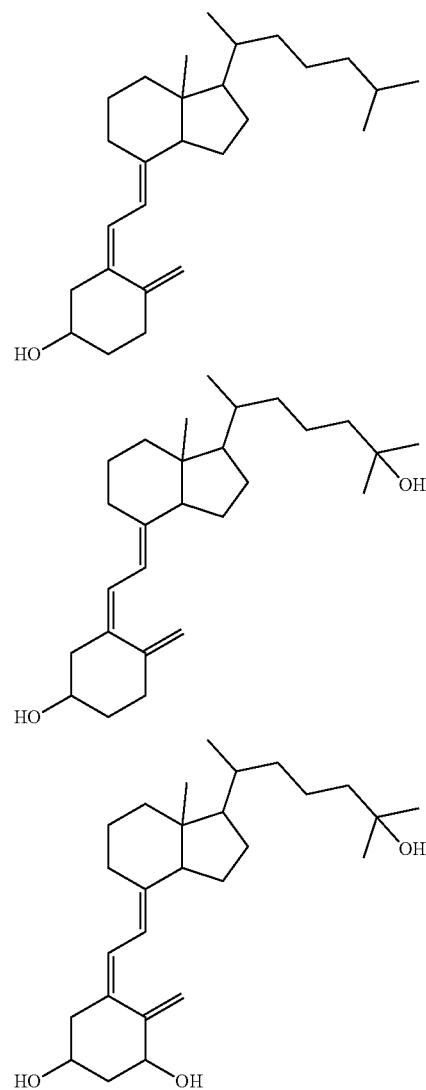

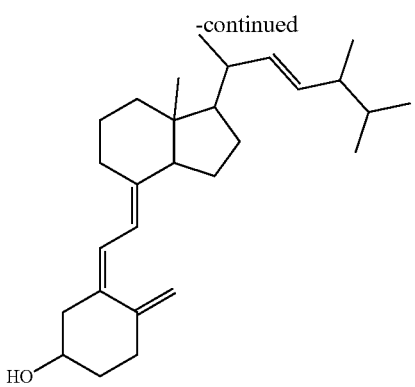

In certain embodiments, the vitamin D compound is 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

In other embodiments, the vitamin D compound is not 1,25-dihydroxyvitamin D3; 1,25-dihydroxy-16-ene-23-yne-cholecalciferol; 1,25-dihydroxy-16-ene-yne-cholecalciferol; 1α-hydroxyvitamin D3; 1α,24-dihydroxyvitamin D3, or MC 903.

Other suitable analogs, metabolites, derivatives and/or mimics of vitamin D compounds include, for example, 1,25-dihydroxyvitamin D3 (also known as calcitriol), 1,25-dihydroxy-16-ene-23-yne-cholecalciferol, and other vitamin D analogs, homologs, mimics, and derivatives of vitamin D compounds such as those described in the following patents, each of which is incorporated by reference in its entirety: U.S. Pat. No. 4,391,802 (1α-hydroxyvitamin D derivatives); U.S. Pat. No. 4,717,721 (1α-hydroxy derivatives with a 17 side chain greater in length than the cholesterol or ergosterol side chains); U.S. Pat. No. 4,851,401 (cyclopentano-vitamin D analogs); U.S. Pat. Nos. 4,866,048 and 5,145,846 (vitamin D3 analogues with alkynyl, alkenyl, and alkanyl side chains); U.S. Pat. No. 5,120,722 (trihydroxycalciferol); U.S. Pat. No. 5,547,947 (fluoro-cholecalciferol compounds); U.S. Pat. No. 5,446,035 (methyl substituted vitamin D); U.S. Pat. No. 5,411,949 (23-oxa-derivatives); U.S. Pat. No. 5,237,110 (19-nor-vitamin D compounds); U.S. Pat. No. 4,857,518 (hydroxylated 24-homo-vitamin D derivatives). Other suitable examples include ROCALTROL (Roche Laboratories); CALCIJEX injectable calcitriol; investigational drugs from Leo Pharmaceuticals including EB 1089 (24a,26a,27a,tri-homo-22,24-diene-1α,25-(OH)2-D3, KH 1060 (20-epi-22-oxa-24a,26a,27a-trihomola, 25-(OH)2-D3), MC 1288 (1,25-(OH)2-20-epi-D3) and MC 903 (calcipotriol, 1a,24s(OH)2-22-ene-26,27-dehydro-D3); Roche Pharmaceutical drugs that include 1,25-(OH)2-16-ene-D3, 1,25-(OH)2-16-ene-23-yne-D3, and 25-(OH)2-16-ene-23-yne-D3; Chugai Pharmaceuticals 22-oxacalcitriol (22-oxa-1α,25-(OH)2-D3; 1α-(OH)-D5 from the University of Illinois; and drugs from the Institute of Medical Chemistry-Schering AG that include ZK 161422 (20-methyl-1,25-(OH)2-D3) and ZK 157202 (20-methyl-23-ene-1,25-(OH)2-D3); 1α-(OH)-D2; 1α-(OH)-D3, 1α-(OH)-D4, 25-(OH)-D2; 25-(OH)-D3; and 25-(OH)-D4. Additional examples include 1α,25-(OH)2-26,27-d6-D3; 1α,25-(OH)2-22-ene-D3; 1α,25-(OH)2-D3; 1α,25-(OH)2-D2; 1α,25-(OH)2-D4; 1α,24,25-(OH)3-D3; 1α,24,25-(OH)3-D2; 1α,24,25-(OH)3-D4; 1α-(OH)-25-FD3; 1α-(OH)-25-FD4; 1α,24-(OH)-25-FD2; 1α,24-(OH)2-D4; 1α,24-(OH)2-D3; 1α,24-(OH)2-D2; 1α,24-(OH)2-25-FD4; 1α,24-(OH)2-25-FD3; 1α,24-(OH)2-25-FD2; 1α,25-(OH)2-26,27-F6-22-ene-D3; 1α,25(OH)2-26,27-F6-D3; 1α,25S—(OH)2-26-F3-D3; 1α,25-(OH)2-24-F2-D3; 1α,25S,26-(OH)2-22-ene-D3; 1α,25R,26-(OH)2-22-ene-D3; 1α,25-(OH)2-D2; 1α,25-(OH)2-24-epi-D3; 1α,25-(OH)2-23-yne-D3; 1α,25-(OH)2-24R-F-D3; 1α,25S,26-(OH)2-D3; 1α,24R—(OH)2-25F-D3; 1α,25-(OH)2-26,27-F6-23-yne-D3; 1α,25R—(OH)2-26-F3-D3; 1α,25,28-(OH)3-D2; 1α,25-(OH)2-16-ene-23-yne-D3; 1α,24R,25-(OH)3-D3; 1α,25-(OH)2-26,27-F6-23-ene-D3; 1α,25R—(OH)2-22-ene-26-F3-D3; 1α,25S—(OH)2-22-ene-26-F3-D3; 1α,25R—(OH)2-D3-26,26,26-d3; 1α,25S—(OH)2-D3-26,26,26-d3; and 1α,25R—(OH)2-22-ene-D3-26,26,26-d3. Yet additional examples can be found in U.S. Pat. No. 6,521,608, the entire disclosure of which is incorporated by reference herein. See also, e.g., U.S. Pat. Nos. 6,503,893, 6,482,812, 6,441,207, 6,410,523, 6,399,797, 6,392,071, 6,376,480, 6,372,926, 6,372,731, 6,359,152, 6,329,357, 6,326,503, 6,310,226, 6,288,249, 6,281,249, 6,277,837, 6,218,430, 6,207,656, 6,197,982, 6,127,559, 6,103,709, 6,080,878, 6,075,015, 6,072,062, 6,043,385, 6,017,908, 6,017,907, 6,013,814, 5,994,332, 5,976,784, 5,972,917, 5,945,410, 5,939,406, 5,936,105, 5,932,565, 5,929,056, 5,919,986, 5,905,074, 5,883,271, 5,880,113, 5,877,168, 5,872,140, 5,847,173, 5,843,927, 5,840,938, 5,830,885, 5,824,811, 5,811,562, 5,786,347, 5,767,111, 5,756,733, 5,716,945, 5,710,142, 5,700,791, 5,665,716, 5,663,157, 5,637,742, 5,612,325, 5,589,471, 5,585,368, 5,583,125, 5,565,589, 5,565,442, 5,554,599, 5,545,633, 5,532,228, 5,508,392, 5,508,274, 5,478,955, 5,457,217, 5,447,924, 5,446,034, 5,414,098, 5,403,940, 5,384,313, 5,374,629, 5,373,004, 5,371,249, 5,430,196, 5,260,290, 5,393,749, 5,395,830, 5,250,523, 5,247,104, 5,397,775, 5,194,431, 5,281,731, 5,254,538, 5,232,836, 5,185,150, 5,321,018, 5,086,191, 5,036,061, 5,030,772, 5,246,925, 4,973,584, 5,354,744, 4,927,815, 4,804,502, 4,857,518, 4,851,401, 4,851,400, 4,847,012, 4,755,329, 4,940,700, 4,619,920, 4,594,192, 4,588,716, 4,564,474, 4,552,698, 4,588,528, 4,719,204, 4,719,205, 4,689,180, 4,505,906, 4,769,181, 4,502,991, 4,481,198, 4,448,726, 4,448,721, 4,428,946, 4,411,833, 4,367,177, 4,336,193, 4,360,472, 4,360,471, 4,307,231, 4,307,025, 4,358,406, 4,305,880, 4,279,826, and 4,248,791, the entire disclosures of each of which are incorporated by reference herein.

Yet other compounds which may be utilized include vitamin D mimics such as bis-aryl derivatives disclosed by U.S. Pat. No. 6,218,430 and WO publication 2005/037755, the entire disclosures of each of which are incorporated by reference herein. Additional examples of non-secosteroidal vitamin D mimic compounds suitable for the present invention can be found in U.S. Pat. Nos. 6,831,106; 6,706,725; 6,689,922; 6,548,715; 6,288,249; 6,184,422, 6,017,907, 6,858,595, and 6,358,939, the entire disclosures of each of which are incorporated by reference herein.

Yet other suitable vitamin D3 analogs, metabolites, and/or derivatives which may be utilized include those identified in U.S. Patent Application Publication No. 2006/0177374, the entire disclosure of which is incorporated by reference herein.

The language "vitamin D analog" includes compounds that are similar to vitamin D in structure and function. In one embodiment, the vitamin D analog is a vitamin D3 analog (e.g., a compound that is similar to vitamin D3 in structure and function).

The language "vitamin D metabolite" includes compounds that are intermediates and the products involved in the metabolism of vitamin D. In one embodiment, the vitamin D metabolite is a vitamin D3 metabolite (e.g., a compound that is an intermediate or product involved in the metabolism of vitamin D3).

The language "vitamin D derivative" includes compound that can arise from a parent compound (e.g., vitamin D) by replacement of one atom with another atom or group of atoms. In one embodiment, the vitamin D derivative is a vitamin D3 derivative (e.g., a compound that can arise from vitamin D3 by replacement of one atom with another atom or group of atoms).

The language "vitamin D mimic" includes compounds that can chemically imitate vitamin D in a biological process. In one embodiment, the vitamin D mimic is a vitamin D3 mimic (e.g., a compound that can chemically imitate vitamin D3 in a biological process).

Vitamin D3 is absorbed after ingestion of fish liver oils or irradiated yeast. Plants and animal sources contain only the inactive vitamin D precursors, 7-dehydrocholesterol or ergosterol. 7-Dehydrocholesterol is stored in the skin and can be converted by sunlight into vitamin D3. However, whether ingested or formed by ultraviolet irradiation in the skin, Vitamin D has to be transformed into active metabolites. Vitamin D3 is converted to 25-hydroxycholecalciferol by liver enzymes. Then in the kidneys two compounds 1,25-dihydroxycholecalciferol and 24,25-dihydroxycholecalciferol are formed. The vitamin D active metabolites play an important role in the absorption of calcium from the intestinal tract, bone deposition and bone reabsorption.

The vitamin D compounds of the invention share certain common biological activities, such as the ability to prevent apoptosis in keratinocytes, partly via their ability to up- or down-regulate certain target gene expressions in, for example, normal keratinocytes (e.g., HEKa). Therefore, in certain embodiments, the vitamin D compounds of the invention may exhibit a similar or identical gene regulation profile as an equivalent amount of calcitriol in, for example, normal keratinocytes (e.g., HEKa).

As used herein, "equivalent amount" includes the same molar amount if the vitamin D compounds have substantially the same or equal biological or therapeutic activity in substantially the same molar amount. However, when different vitamin D compounds are not substantially the same or equal in biological or therapeutic activity, the language "equivalent amount" includes that amount of a vitamin D compound that gives rise to substantially the same amount of biological or therapeutic activity compared to a reference vitamin D compound (e.g., calcitriol).

The language "gene regulation profile" includes the list or spectrum of genes that are statistically significantly (e.g., $p<0.05$) modulated (e.g., up- or down-regulated) when comparing to appropriate controls. For example, upon contacting a cell with a vitamin D compound for a pre-determined period of time (e.g., 24 hours), a target cell may display a spectrum of genes whose mRNA or protein expression level is modulated (e.g. up- or down-regulated) compared to mock/vehicle-treatment control. The list of genes modulated (e.g., up- or down-regulated) at the time of detection constitutes a snapshot of the gene expression profile of the cell at that specific moment.

The language "similar gene regulation profile" includes the situation where more than 50%, 60%, 70%, 80%, 90%, or more of the total number of target genes examined exhibit substantially the same direction of gene expression (e.g., both up-regulated or both down-regulated, although the magnitude or extent of up- or down-regulation in each gene may differ).

The language "identical gene regulation profile" includes the situation where nearly all target genes examined exhibit the same direction of gene expression (e.g., both up-regulated or both down-regulated, although the magnitude or extent of up- or down-regulation in each gene may differ).

In one embodiment, a vitamin D compound of the invention promotes the expression of one or more target genes whose expression levels are promoted by an equivalent amount of a reference vitamin D compound (e.g., calcitriol). In other embodiments, the vitamin D compound of the invention inhibits the expression of one or more genes whose expression levels are inhibited by an equivalent amount of a reference vitamin D compound (e.g., calcitriol).

In certain embodiments, a vitamin D compound of the invention may modulate the expression of proteins in normal keratinocytes. The language "modulate expression of proteins" includes the up-regulation and the down-regulation of proteins in normal keratinocytes. In some embodiments, the vitamin D compound modulates the expression of HSPA2, HSF4 mRNA, HSPB1 or DNAJC6 mRNA. For example, in some embodiments, the vitamin D compound up-regulates the expression of HSPA2 or HSF4 mRNA, and/or down-regulates the expression of HSPB1 or DNAJC6 mRNA in normal keratinocytes (e.g., HEKa).

In certain embodiments, a vitamin D compound of the invention modulates the expression of SLC1A1, KCNB2, KCNN4 protein or SLC1A3 protein in normal keratinocytes. In some embodiments, the vitamin D compound may up-regulate the expression of SLC1A1, KCNB2, or KCNN4 protein, and/or down-regulate the expression of SLC1A3 protein in normal keratinocytes (e.g., HEKa).

In certain embodiments, a vitamin D compound of the invention may modulated one or more proteins in Table 3-1 and Table 3-2. For example, in one embodiment, the vitamin D compound may up-regulate the expression of one or more proteins in Table 3-1 by at least about 2-fold, and/or down-regulate the expression of one or more proteins in Table 3-2 by at least about 2-fold in, for example, normal keratinocytes (e.g., HEKa).

In certain embodiments, a vitamin D compound of the invention may induce over-expression of one or more proteins in any of Tables 3-3, 3-4, 3-5 or 3-6, after about 24-hour exposure of normal keratinocytes (e.g., HEKa) to the vitamin D compound.

In certain embodiments, a vitamin D compound of the invention may induce over-expression in normal keratinocytes (e.g., HEKa) of one or more of: GST, Keratin 1, Keratin 17, Galectin 1, S100 A9 (Calprotectin), or S100 A13.

As used herein, the term "alkyl" includes fully saturated branched or unbranched (e.g., straight chain or linear) hydrocarbon moiety, comprising 1 to 20 carbon atoms, for example, 1 to 7 carbon atoms, or 1 to 4 carbon atoms. Representative examples of alkyl moieties include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl.

Moreover, the term "alkyl" includes both "unsubstituted alkyls" and "substituted alkyls." Representative examples of substituents for alkyl moieties are hydroxy, halogen, cyano, nitro, cycloalkyl, alkenyl, alkynyl, alkoxy, alkenyloxy, alkynyloxy, halogen or amino (including alkyl amino, di-alkylamino, arylamino, di-arylamino).

As used herein, the term "alkoxy" includes alkyl-O—, wherein alkyl is defined herein above. Representative examples of alkoxy moieties include, but are not limited to, methoxy, ethoxy, propoxy, 2-propoxy, butoxy, tert-butoxy, pentyloxy, hexyloxy, cyclopropyloxy-, cyclohexyloxy- and the like. In some embodiments, the alkoxy groups have about 1-7 carbons, for example 1-4 carbons. The term alkoxy includes substituted alkoxy. Examples of substituted alkoxy groups include halogenated alkoxy groups. Examples of halogen substituted alkoxy groups are fluoromethoxy, difluoromethoxy, trifluoromethoxy, chloromethoxy, dichloromethoxy, and trichloromethoxy.

The term "alkoxyalkyl" includes alkyl groups, as defined above, in which the alkyl group is substituted with alkoxy. Moreover, the term "alkoxyalkyl" includes both "unsubstituted alkoxyalkyl" and "substituted alkoxyalkyl." Representative examples of substituents for alkoxyalkyl moieties include, but are not limited to, hydroxy, halogen, cyano, nitro, alkyl, cycloalkyl, alkenyl, alkynyl, alkoxy, alkenyloxy, alkynyloxy, halogen or amino (including alkyl amino, di-alkylamino, arylamino, di-arylamino).

The term "alkenyl" includes branched or unbranched hydrocarbons having at least one carbon-carbon double bond. Representative examples of alkenyl moieties include, but are not limited to, vinyl, prop-1-enyl, allyl, butenyl, isopropenyl or isobutenyl. Moreover, the term "alkenyl" includes both "unsubstituted alkenyls" and "substituted alkenyls." Representative examples of substituents for alkenyl moieties include, but are not limited to, hydroxy, halogen, cyano, nitro, alkyl, cycloalkyl, alkenyl, alkynyl, alkoxy, alkenyloxy, alkynyloxy, halogen or amino (including alkyl amino, di-alkylamino, arylamino, di-arylamino).

The term "alkynyl" includes branched or unbranched hydrocarbons having at least one carbon-carbon triple bond. Representative examples of alkynyl moieties include, but are not limited to, ethynyl, prop-1-ynyl (propargyl), butynyl, isopropynyl or isobutynyl. Moreover, the term "alkynyl" includes both "unsubstituted alkynyls" and "substituted alkynyls." Representative examples of substitutents for alkynyl moieties include, but are not limited to, hydroxy, halogen, cyano, nitro, alkyl, cycloalkyl, alkenyl, alkynyl, alkoxy, alkenyloxy, alkynyloxy, halogen or amino (including alkyl amino, di-alkylamino, arylamino, di-arylamino).

As used herein, the term "cycloalkyl" includes saturated or unsaturated monocyclic, bicyclic or tricyclic hydrocarbon groups of 3-12 carbon atoms, for example, 3-8, or 3-7 carbon atoms. Exemplary monocyclic hydrocarbon groups include, for example, cyclopropyl, cyclobutyl, cyclopentyl, cyclopentenyl, cyclohexyl and cyclohexenyl. Exemplary bicyclic hydrocarbon groups include, for example, bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, and 2,6,6-trimethylbicyclo[3.1.1]heptyl, bicyclo[2.2.2]octyl. An example of a tricyclic hydrocarbon group includes, for example, adamantyl.

The term "cycloalkyl" includes both "unsubstituted cycloalkyl" and "substituted cycloalkyl." Representative examples of substitutents for cycloalkyl moieties include, but are not limited to, hydroxy, halogen, cyano, nitro, alkyl, cycloalkyl, alkenyl, alkynyl, alkoxy, alkenyloxy, alkynyloxy, halogen or amino (including alkyl amino, di-alkylamino, arylamino, di-arylamino).

The term "aryl" includes monocyclic or bicyclic aromatic hydrocarbon groups having 6-20 carbon atoms in the ring portion. Representative examples of aryl moieties include, but are not limited to, phenyl, naphthyl, anthracyl, phenanthryl or tetrahydronaphthyl. Moreover, the term aryl includes both "unsubstituted aryl" and "substituted aryl." Representative examples of substitutents for aryl moieties include, but are not limited to, hydroxy, halogen, cyano, nitro, alkyl, cycloalkyl, alkenyl, alkynyl, alkoxy, alkenyloxy, alkynyloxy, halogen or amino (including alkyl amino, di-alkylamino, arylamino, di-arylamino).

The term "heteroaryl" includes monocyclic or bicyclic heteroaryl moieties, containing from 5-10 ring members selected from carbon atoms and 1 to 5 heteroatoms, selected from O, N or S. Examples of heteroaryl groups include, but are not limited to, thienyl, furyl, pyrrolyl, imidazolyl, pyrazolyl, thiazolyl, isothiazolyl, oxa-2,3-diazolyl, oxa-2,4-diazolyl, oxa-2,5-diazolyl, oxa-3,4-diazolyl, thia-2,3-diazolyl, thia-2,4-diazolyl, thia-2,5-diazolyl, thia-3,4-diazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-,4-, or 5-pyrimidinyl. A heteroaryl group may be mono-, bi-, tri-, or polycyclic.

The term "heteroaryl" further includes groups in which a heteroaromatic ring is fused to one or more aryl, cycloaliphatic, or heterocyclyl rings, where the radical or point of attachment is on the heteroaromatic ring or on the fused aryl ring. Representative examples of such heteroaryl moieties include, but are not limited to, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d] thiazolyl, pyrazino[2,3-d]pyridazinyl, imidazo[2,1-b] thiazolyl, imidazo[1,2-b][1,2,4]triazinyl, 7-benzo[b]thienyl, benzoxazolyl, benzimidazolyl, benzothiazolyl, benzoxazinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl. Moreover, the term "heteroaryl" includes both "unsubstituted heteroaryl" and "substituted heteroaryl."

The aromatic ring of an "aryl" or "heteroaryl" group can be unsubstituted or substituted at one or more ring positions with substituents including, for example, halogen, hydroxy, cyano, nitro, alkyl, cycloalkyl, alkenyl, alkynyl, aryl, heteroaryl, heterocyclyl, alkoxy, cycloalkyloxy, alkenyloxy, alkynyloxy, aryloxy, heteroaryloxy, heterocyclyloxy, arylalkyloxy, heteroarylalkyloxy, heterocyclylalkyloxy, ketones (including alkylcarbonyl, cycloalkylcarbonyl, alkenylcarbonyl, alkynylcarbonyl, aroyl, arylalkylcarbonyl, heteroarylcarbonyl, heterocyclylcarbonyl), esters (including alkoxycarbonyl, cycloalkyloxycarbonyl, aryloxycarbonyl, heteroaryloxycarbonyl, heterocyclyoxycarbonyl, alkylcarbonyloxy, cycloakylcarbonyloxy, arylcarbonyloxy, heteroarylcarbonyloxy, heterocyclylcarbonyloxy), carbonates (including alkoxycarbonyloxy, aryloxycarbonyloxy, heteroaryloxycarbonyloxy), carbamates (including alkoxycarboxylamino, aryloxycarbonylamino, alkenyloxycarbonylamino, alkynyloxycarbonylamino, aryloxycarbonylamino, aminocarbonyloxy, alkylaminocarbonyloxy, di-alkylaminocarbonyloxy, arylaminocarbonyloxy), carbamoyl (including alkylaminoacarbonyl, di-alkylaminocarbonyl, arylaminocarbonyl, arylalkylaminocarbonyl, alkenylaminocarbonyl), amido (including alkylcarbonylamino, alkylcarbonylalkylamino, arylcarbonylamino, heteroarylcarbonylamino), arylalkyl, heteroarylalkyl, heterocycloalkyl, amino (including alkyl amino, di-alkylamino, arylamino, di-arylamino, and alkylarylamino), sulfonyl (including alkylsulfonyl, arylsulfonyl, arylalkylsufonyl, heteroarylsulfonyl, alkoxysulfonyl, aryloxysulfonyl, heteroaryloxysulfonyl, cycloalkylsulfonyl, heterocyclylsulfonyl), sulfamoyl, sulfonamido, phosphate, phosphonato, phosphinato, thioether (including alkylthio, arylthio, heteroarylthio), ureido, imino, amidino, thiocarboxyl (including alkylthiocarbonyl, arylthiocarbonyl), sulfinyl (including alkylsulfinyl, arylsulfinyl), carboxyl, wherein each of the afore-mentioned hydrocarbon groups may be optionally substituted with one or more alkyl, alkenyl, alkynyl, cycloalkyl, halogen, hydroxy or alkoxy groups.

As used herein, the term "heterocyclyl" or "heterocyclo" includes unsubstituted or substituted, saturated or unsaturated non-aromatic ring or ring systems, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocyclyl moieties include, for example, dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxazinyl, oxaazepanyl, oxathianyl, thiepanyl, azepanyl, dioxepanyl, and diazepanyl.

The term "heterocyclyl" includes heterocyclic groups as defined herein that may be substituted with 1, 2 or 3 substituents such as =O, =S, halogen, hydroxy, cyano, nitro, alkyl, cycloalkyl, alkenyl, alkynyl, aryl, heteroaryl, heterocyclyl, alkoxy, cycloalkyloxy, alkenyloxy, alkynyloxy, aryloxy, heteroaryloxy, heterocyclyloxy, arylalkyloxy, heteroarylalkyloxy, heterocyclylalkyloxy, ketones (including alkylcarbonyl, cycloalkylcarbonyl, alkenylcarbonyl, alkynylcarbonyl, aroyl, arylalkylcarbonyl, heteroarylcarbonyl, heterocyclylcarbonyl), esters (including alkoxycarbonyl, cycloalkyloxycarbonyl, aryloxycarbonyl, heteroaryloxycarbonyl, heterocyclyloxycarbonyl, alkylcarbonyloxy, cycloakylcarbonyloxy, arylcarbonyloxy, heteroarylcarbonyloxy, heterocyclylcarbonyloxy), carbonates (including alkoxycarbonyloxy, aryloxycarbonyloxy, heteroaryloxycarbonyloxy), carbamates (including alkoxycarboxylamino, aryloxycarbonylamino, alkenyloxycarbonylamino, alkynyloxycarbonylamino, aryloxycarbonylamino, aminocarbonyloxy, alkylaminocarbonyloxy, dialkylaminocarbonyloxy, arylaminocarbonyloxy), carbamoyl (including alkylaminoacarbonyl, dialkylaminocarbonyl, arylaminocarbonyl, arylalkylaminocarbonyl, alkenylaminocarbonyl), amido (including alkylcarbonylamino, alkylcarbonylalkylamino, arylcarbonylamino, heteroarylcarbonylamino), arylalkyl, heteroarylalkyl, heterocyclylalkyl, amino (including alkyl amino, dialkylamino, arylamino, diarylamino, and alkylarylamino), sulfonyl (including alkylsulfonyl, arylsulfonyl, arylalkylsufonyl, heteroarylsulfonyl, alkoxysulfonyl, aryloxysulfonyl, heteroaryloxysulfonyl, cycloalkylsulfonyl, heterocyclylsulfonyl), sulfamoyl, sulfonamido, phosphate, phosphonato, phosphinato, thioether (including alkylthio, arylthio, heteroarylthio), ureido, imino, amidino, thiocarboxyl (including alkylthiocarbonyl, arylthiocarbonyl), sulfinyl (including alkylsulfinyl, arylsulfinyl), carboxyl wherein each of the afore-mentioned hydrocarbon groups may be optionally substituted with one or more alkyl, alkenyl, alkynyl, cycloalkyl, halogen, hydroxy or alkoxy groups.

The term "heterocyclylalkyl" is an alkyl substituted with heterocyclyl. The term includes unsubstituted and substituted heterocyclylalkyl moieties which may be substituted with one or more alkyl, alkenyl, alkynyl, cycloalkyl, halogen, hydroxy or alkoxy groups.

The term "carbonyl" or "carboxy" includes compounds and moieties which contain a carbon connected with a double bond to an oxygen atom (C=O). The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, urea, anhydrides, etc.

The term "hydroxy" or "hydroxyl" includes groups with an —OH or —O⁻.

The term "halogen" includes fluorine, bromine, chlorine, iodine, etc.

The term "perhalogenated" includes moieties in which all hydrogens are replaced by halogen atoms.

The vitamin D compounds of the invention, or their pharmaceutically acceptable salts, solvates or prodrugs thereof, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "stereoisomer" includes compounds made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposable mirror images of one another.

The present invention includes all pharmaceutically acceptable isotopically-labeled vitamin D compounds in which one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Substitution with heavier isotopes such as deuterium, i.e. $^2$H, may afford certain therapeutic advantages resulting from greater metabolic stability, for example, increased in vivo half-life or reduced dosage requirements. Isotopically-labeled vitamin D compounds can generally be prepared by conventional techniques known to those skilled in the art using an appropriate isotopically-labeled reagent in place of the non-labeled reagent previously employed.

The term "prodrugs" includes compounds that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphorirc acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The language "pharmaceutical composition" includes formulations of a compound of the invention (e.g., a vitamin D compound) and a medium generally accepted in the art, for delivery of the vitamin D compound to an individual. Such a medium includes all pharmaceutically acceptable carriers, diluents or excipients thereof.

In some embodiments, the compositions of the invention can be topically administered to any epithelial surface. An "epithelial surface" include an area of tissue that covers external surfaces of a body, or which lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, gels, creams, emulsions, lotions, slurries, powders, sprays, foams, pastes, ointments, salves, balms, or drops.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, *ceratonia*, dextran and derivatives thereof, ghatti gum, hectorite, ispaghula husk, polyvinypyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Standard composition strategies for topical agents can be applied to the vitamin D compounds in order to enhance the persistence and residence time of the drug, and to improve the prophylactic efficacy achieved.

Topical transdermal patches may also be used. Transdermal patches have the added advantage of providing controlled delivery of the compositions of the invention to the body. Such dosage forms can be made by dissolving or dispersing the agent in the proper medium.

Powders and sprays can contain, in addition to the vitamin D compounds, carriers such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the vitamin D compounds together with conventional pharmaceutically acceptable carriers and stabilizers. The carriers and stabilizers vary with the requirements of the particular compound, but typically include nonionic surfactants (e.g., Tweens, Pluronics, polyethylene glycol and the like), proteins like serum albumin, sorbitan esters, oleic acid, lecithin, amino acids such as glycine, buffers, salts, sugars or sugar alcohols. Aerosols generally are prepared from isotonic solutions. Generation of the aerosol or any other means of delivery of the present invention may be accomplished by any of the methods known in the art. For example, in the case of aerosol delivery, the compound is supplied in a finely divided form along with any suitable carrier with a propellant.

Liquefied propellants are typically gases at ambient conditions and are condensed under pressure. The propellant may be any acceptable and known in the art including propane and butane, or other lower alkanes, such as those of up to 5 carbons. The composition is held within a container with an appropriate propellant and valve, and maintained at elevated pressure until released by action of the valve.

In one embodiment, the vitamin D compound may be administered prophylactically. For prophylactic applications, the vitamin D compound can be applied prior to potential alopecia. The timing of application can be optimized to maximize the prophylactic effectiveness of the vitamin D compound. The timing of application will vary depending on the mode of administration, doses, the stability and effectiveness of composition, the frequency of the dosage, e.g., single application or multiple dosage. One skilled in the art will be able to determine the most appropriate time interval required to maximize prophylactic effectiveness of the vitamin D compound.

The vitamin D compound when present in a composition will generally be present in an amount from about 0.000001% to about 100%, more preferably from about 0.001% to about 50%, and most preferably from about 0.01% to about 25% of total weight.

For compositions of the present invention comprising a carrier, the composition comprises, for example, from about 1% to about 99%, preferably from about 50% to about 99%, and most preferably from about 75% to about 99% by weight of at least one carrier.

Also, the separate components of the compositions of the invention may be preblended or each component may be added separately to the same environment according to a predetermined dosage for the purpose of achieving the desired concentration level of the treatment components and so long as the components eventually come into intimate admixture with each other. Further, the present invention may be administered or delivered on a continuous or intermittent basis.

In one embodiment, the formulation includes the vitamin D active ingredient, formulated in about 40% (w/w) propylene glycol and about 60% (w/w) anhydrous absolute ethanol (200 proof, US), optionally with other minor pharmaceutically acceptable excipients, carriers, or diluents, such as about 0.4% (w/v) of Phospholipon 90G. In another embodiment, the formulation includes the vitamin D active ingredient, formulated in about 30% (w/w) propylene glycol, about 10% (w/w) Ethoxydiglycol or Transcutol, and about 60% (w/w) anhydrous absolute ethanol (200 proof, US), optionally with other minor pharmaceutically acceptable excipients, carriers, or diluents, such as about 0.4% (w/v) of Phospholipon 90G. In some embodiments, the ethanol is anhydrous absolute 200 proof (U.S.) undenatured ethanol (USP). The formulation described herein provides a level of dermal penetration and delivery of the active vitamin D compounds, and provides an effective means to prevent alopecia, or to reduce the severity of alopecia, especially chemotherapy-induced alopecia (CIA).

In certain embodiments, the pharmaceutical composition comprises about 40% (w/w) propylene glycol (USP grade) and about 60% (w/w) anhydrous absolute ethanol (200 proof, US), undenatured USP.

In some embodiments, the pharmaceutical composition comprises about 40% (w/w) propylene glycol (e.g., USP grade or better), and about 60% (w/w) anhydrous absolute ethanol (200 proof, US), undenatured (e.g., USP grade or better).

In other embodiments, the pharmaceutical composition comprises about 30% (w/w) propylene glycol, about 10% (w/w) Ethoxydiglycol or Transcutol, and about 60% (w/w) anhydrous absolute ethanol (200 proof, U.S.).

In yet other embodiments, the pharmaceutical composition comprises about 0.1, 0.2, 0.3, 0.4, 0.5, 0.6, 0.7, 0.8, 0.9, or 1% of Phospholipon, such as Phospholipon 90G.

In other embodiments, the precise percentage (w/w) of propylene glycol and/or anhydrous absolute ethanol may be varied based on the 40%:60% ratio. For example, the % ratio of propylene glycol to anhydrous absolute ethanol may be 20:80; 25:75; 30:70; 35:65; 36:64; 37:63; 38:62; 39:61; 41:59; 42:58; 43:57; 44:56; 45:55, etc. The effectiveness of such other formulations may be verified using and art recognized the techniques, such as the procedure described in Example I.

In certain embodiments, the anhydrous absolute ethanol in the formulation may be replaced with 95% ethanol, 96% ethanol, 97% ethanol, 98% ethanol, or 99% ethanol.

In certain embodiments, the pharmaceutical composition may also include trace amount of other inactive ingredients, excipients, or components. The presence of such ingredients does not substantially affect the effectiveness of the vitamin D compounds or its dermal penetration/accumulation behavior.

The vitamin D compounds of the invention are formulated for delivering to epidermis while having substantially no penetration of the dermis layer. A previous different formulation developed by Roche Dermatology was ineffective in protecting against CIA when used at a dose of about 500-1000 µg per application, and caused dermatitis in the majority of the human subjects in Phase I study. The same Roche formulation also failed to work in the rat chloroleukemic model (infra).

One of the exemplary formulations of the invention can be prepared according to the following (non-limiting) procedure:

| Formula I: Calcitriol at 1.2 µg/g (1.2 ppm) | |
|---|---|
| Ingredient | % w/w |
| 100 ppm Calcitriol concentrate | 1.2 |
| 200 Proof Ethanol | 58.8 |
| Propylene Glycol | 40 |
| Total | 100 |

Formula I is prepared as follows: the calcitriol is dissolved in the ethanol; the propylene glycol is then added and mixed until the resulting solution is clear and uniform in appearance. The specific gravity of the above formulation is approximately 0.875 g/mL. The target concentration of the above formula expressed in w/v is 1.05 µg/mL.

| Formula II: Calcitriol at 3.6 µg/g (3.6 ppm) | |
|---|---|
| Ingredient | % w/w |
| 100 ppm Calcitriol concentrate | 3.6 |
| 200 Proof Ethanol | 56.4 |
| Propylene Glycol | 40 |
| Total | 100 |

Formula II is prepared as follows: the calcitriol is dissolved in the ethanol; the propylene glycol is then added and mixed until the resulting solution is clear and uniform in appearance. The specific gravity of the above formulation is approximately 0.875 g/mL. The target concentration of the above formula expressed in w/v is 3.15 µg/mL.

The reagents used are all USP Grade reagents (meeting the requirements of the U.S. Pharmacopeia).

Using the formulation of the invention, a dosage of about 0.2 µg (administered as 100 µL of 2 µg/mL topical solution) is protective against CIA in neonatal rat. Based on this information, one of skill in the art can readily adjust the proper dosage level based on the average body weight of the mammal to be treated. For example, in human subjects, a total dose of calcitriol (or other equivalent amount of vitamin D compounds) of about 2.5 µg, 5 µg, 10 µg, 25 µg, 50 µg, 75 µg, or 100 µg may be used. Preliminary animal toxicology study shows that a dose of about 100 µg caused no dermal irritation, and exhibited excellent epidermal penetration without substantial dermal penetration (e.g., extremely low penetration to dermis). See description above for additional dosage information.

EXAMPLES

The following examples illustrate certain aspects of the invention, and are not limiting in any respect. While the examples have been described in some details for purposes of clarity and illustration, one skilled in the art will appreciate that various changes in forms and details can be made without departing from the true scope of the invention.

Example 1. Evaluation of the Percutaneous Absorption of Calcitriol, In Vitro, Using the Franz Human Skin Finite Dose Model This example was designed to evaluate the percutaneous absorption pharmacokinetics of various calcitriol formulations. Absorption was measured in human cadaver skin, in vitro, using the finite dose technique and Franz Diffusion Cells. The in vitro human cadaver skin model has proven to be a valuable tool for the study of percutaneous absorption and the determination of the pharmacokinetics of topically applied drugs. The model used human cadaver skin mounted in specially designed diffusion cells that allowed the skin to be maintained at a temperature and humidity that match typical in vivo conditions. A finite dose (e.g., 4-7 mg/cm$^2$) of formulation was applied to the outer surface of the skin and drug absorption was measured by monitoring its rate of appearance in the receptor solution bathing the inner surface of the skin. Data defining total absorption, rate of absorption, as well as skin content was then accurately determined in this model. The method has historic precedent for accurately predicting in vivo percutaneous absorption kinetics. Thus, the in vitro finite dose model on human skin permitted the characterization of the percutaneous absorption pharmacokinetics of vitamin D compounds, such as calcitriol.

In this experiment, six formulations containing calcitriol were tested on three replicate skin sections per formulation on each of three different cadaver skin donors, for the percutaneous absorption of calcitriol over a 48 hour dose period. At pre-selected times after dose application, the dermal receptor solution was removed in its entirety, replaced with fresh receptor solution, and an aliquot saved for subsequent analysis. In addition, the stratum corneum, epidermis, and dermis were recovered and evaluated for drug content. The samples were analyzed for calcitriol content by High Performance Liquid Chromatography (HPLC). A brief description of the protocol used herein is provided below.

Human cadaver trunk skin without obvious signs of skin disease, obtained within 24-48 hours of death, was used in this study. The skin was dermatomed, cryopreserved, and sealed in a water-impermeable plastic bag, and stored at <−70° C. until the day of the experiment. Prior to use, the skin was thawed in ~37° C. water, then rinsed in tap water to remove any adherent blood or other material from the surface. Skin from a single donor was cut into multiple smaller sections large enough to fit on static 2.0 cm$^2$ Franz diffusion cells. Three replicates per donor were tested for each formulation. The dermal chamber was filled to capacity with a reservoir solution of phosphate-buffered isotonic saline (PBS), pH 7.4±0.1, and the epidermal chamber was left open to ambient laboratory environment. Volpo (Oleth-20), a non-ionic surfactant known to increase the aqueous solubility of poorly water soluble compounds, may be added to PBS. Volpo in the reservoir solution insures diffusion sink conditions during percutaneous absorption, and is known not to affect the barrier properties of the test skin. The cells were then placed in a diffusion apparatus in which the dermal reservoir solution was stirred magnetically at ~600 RPM and its temperature maintained to achieve a skin surface temperature of 32.0±1.0° C.

To assure the integrity of each skin section, its permeability to tritiated water was determined before application of the test products. Following a brief (0.5-1 hour) equilibrium period, $^3H_2O$ (NEN, Boston, Mass., sp. Act. ~0.5 µCi/mL) was layered across the top of the skin by dropper so that the entire exposed surface was covered (approximately 250-500 µL). After 5 minutes, the $^3H_2O$ aqueous layer was removed. At 30 minutes, the reservoir solution was collected and analyzed for radioactive content by liquid scintillation counting. Skin specimens in which absorption of $^3H_2O$ is less than 1.56 µL-equ/cm$^2$ are considered acceptable. All skin samples used had $^3H_2O$ absorption of less than about 0.50 µL-equ/cm$^2$ (results not shown).

Dose Administration and Sample Collection:

Just prior to dosing, a pre-dose sample was taken and the reservoir solution was replaced with a fresh solution of 0.1× PBS with 0.2% Volpo (also known as Oleth-20, a non-ionic surfactant used to ensure miscibility of the drug in an aqueous solution). The chimney was removed from the Franz Cell to allow full access to the epidermal surface of the skin. All formulations were then applied to the skin sections using a positive displacement pipette set to deliver 10 µL formulation/cm$^2$. The dose was spread across the surface with the Teflon tip of the pipette. Five to ten minutes after application, the chimney portion of the Franz Cell was replaced. At pre-selected times after dosing, (6, 12, 24, and 48 hours) the reservoir solution was removed in its entirety, replaced with fresh reservoir solution, and a predetermined volume aliquot saved for subsequent analysis.

A single skin section from each donor was mounted onto cells which were not dosed but used to evaluate for the appearance of substances diffusing out of the skin, which may represent endogenous calcitriol. After the last sample was collected, the skin surfaces were washed twice (1.0 mL volume each) with 80:20 Ethanol:Water to collect un-absorbed formulation from the surface of the skin. Following the wash, the skin was removed from the chamber and split into epidermis and dermis. Each layer was extracted overnight in 80:20 Ethanol:Water.

Quantification of calcitriol was by High Performance Liquid Chromatography (HPLC). Briefly, HPLC was conducted on a Hewlett-Packard 1100 Series HPLC system with an Agilent 1100 Series LC/MSD. A solvent system consisting of A) 0.1% Ammonium Acetate in Water and B) 0.1% Ammonium Acetate in Methanol was run through a Phenomenex Luna C18 (2) column (100A, 3µ, 100×4.6 mm) at a flow rate of 0.550 mL/min Peak areas were quantified to concentration using an external standard curve prepared daily from the neat standard. Samples not assayed on the day of collection were stored at or below −20° C.

In the pilot study, a single formulation from the group was dosed to six chambers at about 5 µL/cm$^2$ dose on a single donor. Receptor solutions were collected at 0, 2, 4, 8, 12, 24, 32, and 48 hours. Following the last receptor solution sample, the surface was washed and the skin collected for analysis as previously described. All samples were processed and analyzed for calcitriol content.

The final design of the pivotal study was based on the results observed in the pilot study, in particular, applied dose, receptor solution sampling schedule, and sample processing methods. These modifications were made to optimize the detection and quantification of calcitriol in the pivotal study samples. For example, although the pilot protocol states that reservoir samples were taken at 2, 4, 8, 12, 24, 32, and 48 hours, it was determined after the pilot study, that reservoir samples would be taken at 6, 12, 24, and 48 hours to facilitate better detection levels of Calcitriol in the reservoir samples. In addition, following a pilot study, it was determined that dosing to 2 cm$^2$ with 20 µL (dosing amount was then 10 µL/cm$^2$) would improve detection of calcitriol in the reservoir solution samples. However, the non-dosed chambers were retained at 1 cm$^2$. The following parameters were calculated: a) total absorption (sum of all reservoir solutions); b) rate and extent of penetration across the study period; and c) mass balance of the applied dose. For data evaluation, a) if any sample was <LLQ (Lower Limit of Quantification), then that sample may be treated as a non-data value. For radioactive samples (e.g., the water integrity test), LLQ was defined as the predetermined mean background of blank samples. At the discretion of the investigator, all values <LLQ were declared as zero values or actual value measured for the purpose of calculating key parameters; b) a suspected outlier were confirmed if it is greater than the mean±3SD range of the same values from the set of remaining replicate chambers, or as determined by the Dean and Dixon Outlier test. At the discretion of the investigator, values declared as outliers were removed from the overall summation of the data (but are noted as such in the text or data tables); c) within a chamber, if a given time-point value has been declared a non-data value, or is missing due to other reasons, the time-point value was replaced with an interpolated value to calculate the relevant parameters. The interpolated value is calculated on a line that connects the adjacent values as follows:

Given 3 points: (T1,A), (T2,B) and (T3,C) with (B) missing,

Where T=Time and A-C=measured data values

Estimated B=A−[((A-C)/|T1-T3|)× (|T1-T2|)]

For statistical evaluation, replicates within donors were averaged and standard deviation calculated for each key parameter. Within donor averages were then collated and the across donor population mean with standard error was calculated. Differences between test articles were evaluated using the Student's t-test.

Using this protocol, the following test formulations were evaluated:

A: (1 ppm): dissolve 0.2 mL (1% (w/v)) of 100 ppm calcitriol concentrate (lot number H, below) into 19.8 mL (99% (w/v)) of 200 proof ethanol (1 µg/mL).

B (1 ppm): first, dissolve 0.2 mL (1% (w/v)) of 100 ppm calcitriol concentrate (lot number H, below) into 11.8 mL (59% (w/v)) of 200 proof ethanol; then add 8 mL (40% (w/v)) of propylene glycol, and mix until clear and uniform (1 µg/mL).

C (1 ppm): first, dissolve 0.2 mL (1% (w/v)) of 100 ppm calcitriol concentrate (lot number H, below) into 11.8 mL (59% (w/v)) of 200 proof ethanol; then add 6 mL (30% (w/v)) of propylene glycol and 2 mL (10% (w/v)) of ethoxydiglycol, and mix until clear and uniform (1 µg/mL).

D (3 ppm): first, dissolve 0.6 mL (3% (w/v)) of 100 ppm calcitriol concentrate (lot number H, below) into 11.4 mL (57% (w/v)) of 200 proof ethanol; then add 6 mL (30% (w/v)) of propylene glycol and mix until clear and uniform; finally add 2 mL (10% (w/v)) of ethoxydiglycol and mix until clear and uniform (3 µg/mL).

E (1 ppm): first, dissolve 0.2 mL (1% (w/v)) of 100 ppm calcitriol concentrate (lot number H, below) into 11.72 mL (58.6% (w/v)) of 200 proof ethanol (DP-04-099); then add 6 mL (30% (w/v)) of propylene glycol and mix until clear and uniform; then add 2 mL (10% (w/v)) of Transcutol P and mix until clear and uniform; finally, add 0.08 mL (0.4% (w/v)) of Phospholipon 90G concentrate (lot number G, below) and disperse into solution, mix until clear and uniform (1 µg/mL).

F (3 ppm): first, dissolve 0.6 mL (3% (w/v)) of 100 ppm calcitriol concentrate (lot number H, below) into 11.32 mL (56.6% (w/v)) of 200 proof ethanol; then add 6 mL (30% (w/v)) of propylene glycol and mix until clear and uniform; then add 2 mL (10% (w/v)) of Transcutol P and mix until clear and uniform; finally, add 0.08 mL (0.4% (w/v)) of Phospholipon 90G concentrate (lot number G, below) and disperse into solution, mix until clear and uniform (31 µg/mL).

G: mix 50 g (50% (w/v)) of 200 proof ethanol with 50 g (50% (w/v)) of Phospholipon 90G, and mix until clear and uniform.

H: completely dissolve 0.01 mg (0.01% (w/v)) of calcitriol in 100 mL (99.99% (w/v)) of 200 proof ethanol.

All reagents used in this study were analytical reagent grade or better. Source of unique reagents will be noted after the first mention of each chemical within the text of the final report.

The results of this study are summarized in the Summary table below:

Summary Table: Average Results Across Donors for Calcitriol Content in Epidermis, Dermis, and Total Absorption Percutaneous Absorption of Calcitriol using Human Cadaver Skin over 48 hours from a Single Application. Mean ± SE as Total Mass (ng)

| Test Article | Epidermis (ng/cm$^2$) | Dermis (ng/cm$^2$) | Total Absorption (ng/cm$^2$) |
|---|---|---|---|
| Lot A | 0.98 ± 0.19 | 0.11 ± 0.11 | 9.85 ± 0.62 |
| Lot B | 1.63 ± 0.44 | 0.19 ± 0.19 | 9.84 ± 0.67 |
| Lot C | 1.89 ± 0.54 | 0.00 ± 0.00* | 9.74 ± 0.43 |
| Lot D | 6.44 ± 0.74 | 0.00 ± 0.00 | 10.51 ± 0.10 |
| Lot E | 2.19 ± 0.14 | 0.00 ± 0.00 | 9.96 ± 0.32 |
| Lot F | 4.83 ± 0.42 | 0.00 ± 0.00 | 8.80 ± 0.25 |
| Non-Dosed Blank Cells | 0.37 ± 0.37 | 0.00 ± 0.00 | 13.75 ± 0.59** |

*Zero values indicated results below the lower limit of detection.
**Presumed to be endogenous calcitriol being released from the skin.

The data indicate that calcitriol did penetrate into, but not necessarily through, human cadaver skin, in vitro, from the test formulations evaluated. Blank, non-dosed, skin sections from each donor demonstrated an HPLC/MS coeluting peak consistent with endogenous calcitriol. The amount present in the reservoir solution, being essentially identical across all test formulations, and similar to the non-dosed skin sections, was most likely the diffusion of endogenous calcitriol being released from the skin sections. As little difference was seen across the test formulations and the non-dosed chambers, it is unlikely that the amount seen in the reservoir solution represents calcitriol coming from the topically applied test formulations.

Figure 1:
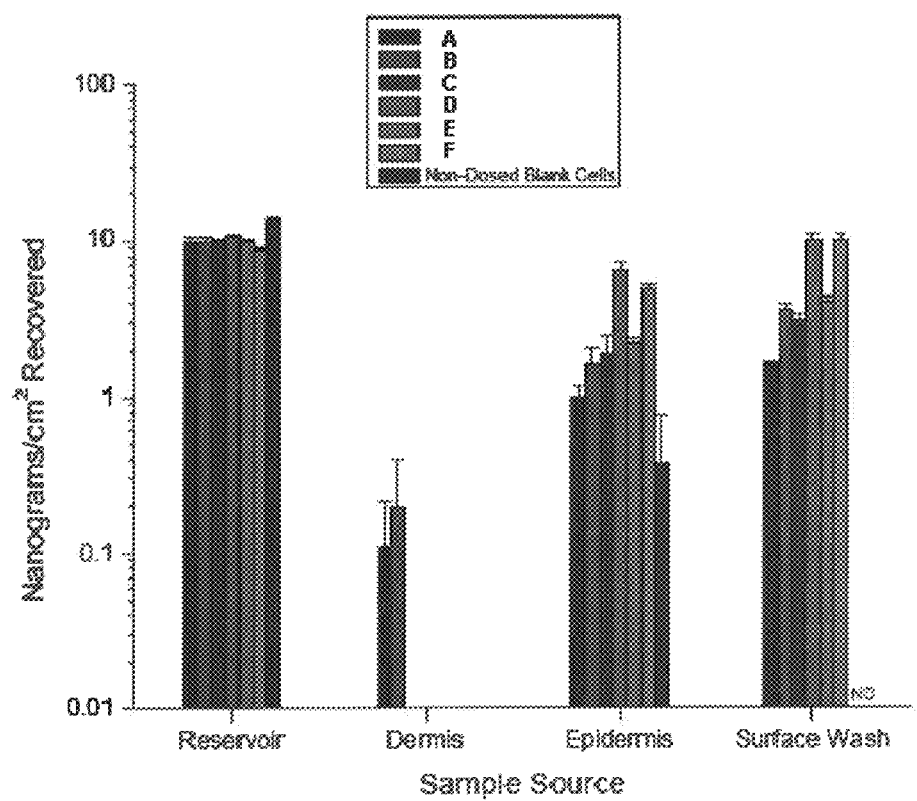
FIG. 1 shows total absorption and mass balance results across the three skin donors, and the distribution of calcitriol from intact human cadaver skin over 48 hours from a single application. Results are shown in log scale as mean±SE as total mass (ng/cm$^2$).

Evidence of calcitriol absorption was observed, as dermal contents, in those skin sections that were dosed with two formulations (A and B), is seen in FIG. 1. As no measurable levels in the dermal skin layer was seen from the non-dosed skin sections, the measurable dermal levels from these two test formulations are interpreted, therefore, to represent absorption from the applied dose. In addition, all epidermal samples dosed with test formulations demonstrated calcitriol levels greater (~3× to ~17×) than the non-dosed skin sections. Rank ordering based upon epidermal calcitriol content arranges the test formulations as:

D>F>E>C>B>A>>>Non-Dosed Skin

Consistent with this rank order is that the test formulations demonstrating the greater epidermal contents where those that contain the higher concentrations (3 μg/mL vs. 1 μg/mL) of calcitriol (D and F). A very similar rank order is observed in the surface wash results (recovery of residual test article from the surface of the skin). No calcitriol was found in the surface wash of the non-dosed blank skin sections.

Example 2. Identification of Key Proteins Involved in Epidermal Cell Culture Response to Calcitriol—Real Time PCR (RTPCR)

This and the following several examples provide additional information regarding the identity of proteins or genes in the activation pathways for Calcitriol. These experiments allow the identification of the mechanism of action and key proteins/genes involved in the cellular response of epidermal cells to vitamin D compounds.

Specifically, it was found that exposing the keratinocyte cell line HEKa to calcitriol caused a significant impact on cellular processes. The experiments described herein focus on the identification of key proteins/genes that were involved in calcitriol induced changes in calcium channel transport and changes in regulation of heat shock proteins. Real-time polymerase chain reaction (RTPCR) methods were employed in this example to identify changes in the level of mRNA's for genes involved in ion channels, transport proteins, and heat shock proteins.

Using PCR arrays as a screening tool, a spectrum of molecular targets that would potentially offer an insight to the mode of biological action of calcitriol within the cells were evaluated. Changes in mRNA levels were evaluated using real-time PCR quantification to assess mRNA levels in preselected subsets containing 80 pathway specific targets (see Appendix). The PCR array analysis utilized two groups of genes—those related to Heat Shock Proteins (SABiosciences), and those related to Neuroscience Ion Channels and Transporters (SABioscience).

Cell Culture:

Primary human epidermal keratinocytes (HEKa) were maintained in Epilife Medium (Cascade Biologics, Inc., Portland Oreg.) along with Human Keratinocyte Growth Supplement (Cascade Biologics, Inc., Portland Oreg.). Cells were grown at 37° C. with 5% $CO_2$.

D3 Treatment of HEKa Cells:

HEKa cells were treated with 0.1 μg/mL of calcitriol or the control vehicle. To give a 0.1 μg/mL final concentration of calcitriol, 1 mg of Calcitriol was dissolved in 2 mL of ethanol, and 1 μL of the resulting stock was added to 5 mL of media. Vehicle control group of cells were treated with 5 mL media containing 1 μL of ethanol. Cells were harvested 3, 6, 16, 24, 48, or 72 hours after the start of the treatment.

RNA Isolation:

Cells were lysed for RNA isolation at different treatment times using the RNeasy Mini kit (Qiagen, Inc., Valencia Calif.) following the manufacturer's instructions. RNA was quantified by measuring optical density at 260 nm. First Strand Synthesis: First strand cDNA was synthesized from 1 μg of total RNA using the RT2 First Strand Synthesis kit (SABiosciences, Frederick Md.) as per manufacturer's recommendations.

Real-Time PCR:

Products from the first strand synthesis were diluted with water, mixed with the SYBR green master mix (SABiosciences, Frederick Md.) and loaded onto PCR arrays. Real time PCR was run on the PCR Arrays (Heat Shock Protein Arrays, and Neuroscience and Ion Channel Arrays) (SABiosciences, Frederick Md.) on a Biorad CFX96. Data analyses were performed using the PCR array data analysis software available on the SABiosciences website.

Table 2-1 below shows the genes on the Heat Shock Protein Gene Array that are regulated in HEKa cells after calcitriol treatment. Results show only those genes that were regulated in two independent experiments.

TABLE 2-1

Genes in the Heat Shock Protein Array Regulated by Vitamin D3 Treatment.

| Gene symbol | Protein | Regulation Pattern |
|---|---|---|
| HSPB1 | Heat shock 27 kDa protein 1 | Down regulated at 48 hours |
| DNAJC6 | DnaJ (Hsp40) homolog, subfamily C, member 6 | Downregulated |
| HSPA2 | Heat shock 70 kDa protein 2 | Upregulated at 48 hours |
| HSF4 | Heat shock transcription factor 4 | Upregulated at 48 hours |

Two of the genes that were regulated at the mRNA level by calcitriol treatment in HEKa cells were HSPB1 and HSPA2. HSPB1 is a 27 kDa protein that is expressed not only in the cell membrane, but also in the cytosol, mitochondria, and the golgi bodies. HSPA2 is a 70 kDa protein present in the cell membrane and nucleus, and is regulated by HSF1. Both HSPB1 and HSPA2 have been implicated in apoptosis. HSF4 is regulated by retinoic acid, and is involved in cell differentiation. DNAJC6 belongs to the HSP40 group of proteins. It is present in clathrin coated vesicles and in the cytoplasm.

Similarly, results obtained from the Neuroscience and Ion Channels Array consistent from three independent experiments are summarized below in Table 2-2.

TABLE 2-2

Genes in the Neuroscience and Ion Channels Array Regulated by Vitamin D3 Treatment

| Gene Symbols | Gene | Regulation Pattern |
|---|---|---|
| SLC1A1 | Solute Carrier family 1 (neuronal/epithelial high affinity glutamate transporter, system Xag), member 1) | upregulated at 16 hrs |
| KCNB2 | Potassium voltage-gated channel, Shab-related subfamily, member 2 | upregulated until 24 hours |
| KCNN4 | Potassium intermediate/small conductance calcium-activated channel, subfamily N, member 4 | upregulated at 48 hours |
| SLC1A3 | Solute carrier family 1 (glial high affinity glutamate transporter), member 3 | downregulated at 48 hours |

Changes in glutamate transporters and in potassium channels was consistently observed. SLC1A1 (also known as EAAC1 or EAAT3) is known to be primarily responsible for transport of the excitatory neurotransmitter glutamate across the membrane. This solute carrier protein has been found outside of the nervous system in tissues such as the heart and skin. In rat keratinocytes, there is evidence showing the involvement of glutamate signaling and SLC1A1 in wound healing (Genever et al., 1999). Inhibition of SLC1A1 by Riluzole, a drug currently in clinical trials for melanoma (Clinical Trials.gov, Mosby's Drug Consult, 13th Edition) is indicative of a biological role of SLC1A1 in skin cells. Given that SLC1A1 has been implicated in anti-apoptotic mechanisms in injured motor neurons (Kiryu-Seo et al., 2006), the observation in this experiment that SLC1A1 is upregulated by D3 treatment in HEKa cells suggests a potential protective mechanism pathway link.

SLC1A3 (also known as EAAT1 or EA6) is another solute carrier which allows a sodium-dependent glutamate and aspartate transport. Typically found in glial cells in the brain, this transporter is involved in cleaning up the synaptic space of glutamate, thereby preventing prolonged depolarization of post synaptic neurons. SLC1A3 is known to interact with glial derived neurotropic factor (GDNF) and phosphodiesterase 6B (PDE6B). It is possible that SCL1A3 is involved in reducing cytotoxicity.

KCNN4 is a potassium intermediate/small conductance calcium-activated channel, subfamily N, member 4. Following its activation, the cell membrane is hyperpolarized and there is increased calcium influx into the cell. This potassium channel is localized in many tissues outside of the nervous system.

KCNB2, potassium voltage-gated channel, Shab-related subfamily, member 2, is upregulated at about 24 hours post calcitriol treatment. This potassium channel is important in regulating neurotransmitter release, insulin secretion and smooth muscle contraction.

Although calcitriol was used in these experiments, one of skill in the art will readily understand that other vitamin D compounds of the invention (such as those described herein above) may also exhibit similar activities in regulating target gene expression. It is contemplated that, in certain embodiments, the vitamin D compounds of the invention exhibit a similar or identical gene modulation profile as that of calcitriol in these experiments, e.g., up-regulating the expression (mRNA and/or protein) of one or more target genes similarly up-regulated by calcitriol, or down-regulating the expression (mRNA and/or protein) of one or more target genes similarly down-regulated by calcitriol.

Example 3. Identification of Key Proteins Involved in Epidermal Cell Culture Response to Calcitriol—Antibody Array Evaluation of protein changes upon calcitriol stimulation was also evaluated through utilization of antibody microarrays, which are capable of screening for changes in over 700 potential target proteins.

In this experiment, an antibody microarray (Panorama XP725 Antibody Array, Sigma) encompassing antibodies against over 700 target proteins was utilized to assess changes in protein concentration/level in HEKa cells treated with calcitriol for about 3, 6, or 24 hours, respectively. Briefly, the treated HEKa cells were first harvested and then extracted to obtain a soluble protein supernatant. Two portions of the extracted protein sample (~1 mg total) from each sample (at 1 mg/mL) were each labeled with fluorescent dye (Cy3 and Cy5, respectively). The excess dye was removed from the protein sample, and the resulting labeled protein samples were used for microarray incubation.

To determine the expression level of a particular target protein at a later time point (e.g., at hour 6 or 24) relative to that at an earlier time point (e.g., at hour 3), the samples were labeled by different labels (e.g., 3-hour extract labeled with Cy3, 6-hour or 24-hour extract labeled with Cy5). Then the two labeled samples containing equal amounts of total protein were mixed (e.g., Cy3-labeled 3-hour sample is mixed with Cy5-labeled 6-hour or 24-hour samples, respectively). After incubation with the microarray chip (according to manufactures recommended protocols), the chips were washed and dried. The microarrays were then scanned with a fluorescent laser scanner to measure the relative fluorescence intensity of the Cy3 and Cy5 dyes.

If the amount of a particular type of target protein increased (or decreased) over time, more (or less) of the dye associated with the later time point (e.g., Cy5) will be retained by the microarray. For example, in this experiment, the earliest time point (e.g., 3-hour) was used as a baseline to determine the relative protein expression level at two later time points (e.g., 6-hour vs. 24-hour). If more Cy5 is retained by the array between 6-24 hours, the expression level of the target protein increased over the time period. Conversely, if there is a decrease in retained Cy5 between hour 6 and 24, the target protein expression level is decreased.

Initial analysis using this method focused on those target proteins exhibiting relative expression level changes >2-fold (increase or decrease). Overall, the antibody array experiments using the calcitriol-treated (24 hour) HEKa cells identified the following target proteins (in Tables 3-1 and 3-2) with significantly altered expression level in response to vitamin calcitriol:

TABLE 3-1

Target Proteins with Increased (>2-fold) Protein Levels Following Calcitriol Treatment

| | |
|---|---|
| Amyloid Precursor Protein | HDAC2 |
| ARTS | HDAC6 |
| ASAP1 Centaurin b4 | ILK |
| BACH1 | MAP Kinase Activated Protein Kinase2 MAPKAPK2 |
| Bclx | MAP Kinase ERK1 |
| BclxL | Melanocortin3 Receptor |
| BID | Myosin IX Myr5 |
| Bmf | Neurofilament 200 |
| CENPE | Nitric Oxide Synthase bNOS |
| cMyc | p120ctn |
| Cofilin | PAD14 |
| Connexin 32 | Par4 Prostate Apoptosis Response 4 |
| Csk | Presenilin1 |
| CtBP1 | Proliferating Cell Protein Ki67 |
| DcR2 | Protein Kinase Ba |
| Dimethyl Histone H3 diMeLys4 | PUMA bbc3 |
| Dimethyl Histone H3 diMeLys9 | ROCK1 |
| Dystrophin | S100 |
| ERK5 BIG MAPKBMK1 | SHPTP2 |
| Estrogen Receptor | Sin3A |
| FKHRL1 FOXO3a | Substance P Receptor |
| Focal Adhesion Kinase pp125FAK | Synaptopodin |
| FOXP2 | Tumor Necrosis Factor a |
| Glutamic Acid Decarboxylase 65 | Ubiquitin Cterminal Hydrolase L1 |
| Glutamic Acid Decarboxylase GAD65 67 | Uvomorulin ECadherin |
| gTubulin | Vitronectin |

TABLE 3-2

Target Proteins with Decreased (>2-fold) Protein Levels Following Calcitriol Treatment Crk II
Growth Factor Independence1
Serine Threonine Protein Phosphatase 1b
Cathepsin D
Transforming Growth Factorb pan
WAVE
Protein Tyrosine Phosphatase PEST
CD40

Evaluation of calcitriol treated HEKa cells at 24-hour with the same protein antibody array method identified about fifty proteins that were significantly upregulated. These proteins generally fall within four categories: (i) transcriptional and cell cycle control (Table 3-3); (ii) structural, cytoskeletal and adhesion proteins (Table 3-4); (iii) apoptosis regulation proteins (Table 3-5); and (iv) nerve cell differentiation and Alzheimer's disease (Table 3-6).

TABLE 3-3

Over-expressed Proteins relating to Cell Cycle and Transcriptional Control (after 24 Hours of Calcitriol treatment)

| Protein | Function |
|---|---|
| BACH1 | transcription factor (Alzheimer's) |
| CENPE | Centromere protein that accumulates in the G2 phase of the cell cycle |
| cMyc | transcription factor (Cancer oncogene) |
| C-src tryosine kinase (Csk) | cell growth (Cancer) |
| CtBP1 | transcriptional repressor |
| Dimethyl Histone H3 diMeLys4 | transcription regulation |
| Dimethyl Histone H3 diMeLys9 | transcription regulation |
| Estrogen Receptor | ligand dependent nuclear receptor |
| FKHRL1 FOXO3a | transcription factor, linked to ROCK kinase and NO signaling |
| FOXP2 | transcription regulator, in development of brain, lung, gut |
| HDAC2 | regulates gene expression |
| MAP Kinase Activated Protein Kinase2 MAPKAPK2 | A kinase involved in many cellular processes (stress and inflammatory responses, nuclear export, gene expression regulation and cell proliferation. Heat shock protein HSP27 was shown to be one of the substrates. |
| MAP Kinase ERK1 | acts in a signaling cascade that regulates various cellular processes such as proliferation, differentiation, and cell cycle progression in response to a variety of extracellular signals, phosphorylates nuclear proteins |
| Melanocortin3 Receptor | hormone receptor |
| Proliferating Cell Protein Ki67 | proliferation marker |
| S100 | calmodulin-like calcium binding protein involved in regulation of multiple cell processes |
| SHPTP2 | a kinase that plays a regulatory role in various cell signaling events |
| Sin3A | transcriptional regulatory protein |

TABLE 3-4

Over-expressed Proteins relating to Structural, cytosckeletal and adhesion (after 24 Hours of Calcitriol treatment)

| Protein | Function |
|---|---|
| ARTS | Regulates cytoskeletal organization |
| ASAP1 Centaurin b4 | reculate actin cytoskeleton |
| Cofilin | dissembles actin filaments |
| Connexin 32 | major component of peripheral myelin |
| Dystrophin | large protein for cytoskelton connection |
| Focal Adhesion Kinase pp125FAK | Phosphorylation of focal adhesion kinase is increased in keratinocytes induced to migrate |

TABLE 3-4-continued

Over-expressed Proteins relating to Structural, cytosckeletal and adhesion (after 24 Hours of Calcitriol treatment)

| Protein | Function |
| --- | --- |
| gTubulin | microtubial, spindle pole |
| Myosin IX Myr5 | motor proteins |
| Neurofilament 200 | nerve cell related structural protein |
| p120ctn | adhesion and signal transduction |
| PAD14 | converts arginine residues to citrulline residues; may regulate intermediate filament proteins and intermediate filament-associated proteins in cells undergoing degenerative processes |
| ROCK1 | kinase, contributes to actin stability |
| Uvomorulin ECadherin | Ca-dependent cell adhesion molecule, transmembrane glycoprotein that functions to regulate epithelial cell recognition and adhesion |
| Vitronectin | promotes cell adhesion and spreading |

TABLE 3-5

Over-expressed Proteins relating to Apoptosis control (after 24 Hours of Calcitriol Treatment)

| Protein | Function |
| --- | --- |
| Bclx | Apotosis regulation |
| BclxL | Apotosis regulation |
| BID | Apotosis regulation |
| Bmf | Apotosis regulation |
| DcR2 | Receptor contains an extracellular TRAIL-binding domain, a transmembrane domain, and a truncated cytoplamic death domain. This receptor does not induce apoptosis, and has been shown to play an inhibitory role in TRAIL-induced cell apoptosis. |
| ERK5 BIG MAPKBMK1 | Protects Endothelial Cells From Apoptosis by phosphorylation of Bad |
| Integrin-linked kinase (ILK) | regulating integrin-mediated signal transduction, may prevent apoptosis in association with PKB/Akt pathways |
| Protein Kinase Ba | (Akt) involved in cell survival and inhibition of apoptosis |
| PUMA bbc3 | apoptosis regulator |

TABLE 3-6

Over-expressed Proteins Associated with Nerve Cell Differentiation and Alzheimer's Disease (after 24 Hours of Calcitriol treatment)

| Protein | Function |
| --- | --- |
| Amyloid Precursor Protein | Amyloid precursor protein (APP) is an integral membrane protein expressed in many tissues and concentrated in the synapses of neurons. Its primary function is not known, though it has been implicated as a regulator of synapse formation[2] and neural plasticity.[3] |
| BACH1 | transcription factor (Alzheimer's) |
| Presenilin1 | the sub-component of gamma secretase that is responsible for cutting APP (mutations observed in Alzheimer's) |
| Glutamic Acid Decarboxylase 65 | neurotransmitter production (Schizophrenia) |
| Glutamic Acid Decarboxylase GAD65 67 | neurotransmitter production (Schizophrenia) |
| Neurofilament 200 | nerve cell related structural protein |
| Nitric Oxide Synthase bNOS | inducible, cell signaling, immune systems |
| Substance P Receptor | a neuropeptide receptor |
| Synaptopodin | actin binding protein, involved in spine apparatus formation in neurons |
| Connexin 32 | major component of peripheral myelin |
| Tumor Necrosis Factor a | regulation of immune cells |
| Ubiquitin Cterminal Hydrolase L1 | neuron specificity (Alzheimer's and Parkenson) |

Example 4. Identification of Key Proteins Involved in Epidermal Cell Culture Response to Calcitriol—Proteomic Analysis A series of HEKa cultures were treated with calcitriol, and cell pellets were harvested at 3, 6, and 24 hours after calcitriol 3 exposure. The cell pellets were then analyzed using proteomic methods, such as 2-D gel and Western blot analysis. In the experiment described below, HEKa cells were treated with 0.1 µg/mL calcitriol, and samples obtained at 3-, 6-, and 24-hour were processed by 2-D gel electrophoresis and the associated comparative analysis (results not shown).

In all, analysis of about 458 protein spots in the comparative study was performed, comparing the control sample against the 3-, 6-, and 24-hour treatment samples. Six spots showing statistically significant differential changes were identified. These spots were excised, and their protein contents subjected to sequence identification by trypsin digestion and mass spectrometry characterization.

Results (Table 4-1) showed that the set of six spots from the HEKa keratinocyte samples contained pure endogenous keratins, as opposed to keratin often observed as a common contaminant. Two S100 proteins were identified as being strongly regulated, along with Glutathione S-transferase and Galectin 1. There was evidence that Galectin 1 was glycosylated.

TABLE 4-1

Proteins identified as being strongly modulated by
Calcitriol based on 2-D gel electrophoresis study

| Spot | Identified Protein | Name | Response | Function | Cellular Location |
|---|---|---|---|---|---|
| 4 | Glutathione S-transferase | GST | up at 3, 6, and 24 hours | GST transfer | cytoplasm |
| 2 | Keratin 1 | KRT1 | up at 6 hours and down at 24 hours | intermediate filament | cytoplasm |
| 8 | Keratin 17 | KR17 | down at 24 hours | intermediate filament | cytoplasm |
| 10 | S100 A9 (Calprotectin) | S100A9 | down at 6 and 24 hours | Calcium binding protein | cytoplasm |
| 14 | S100 A13 | S100A13 | up at 6 and 24 hours | Calcium binding protein | cytoplasm |
| 27 | Galectin 1 | LGALS1 | up at 6 and 24 hours | beta-galactoside-binding protein | Extracelluar |

The two S100 proteins (A9 and A13) belong to the calprotectin family of proteins. There are 21 different types of these low molecular weight proteins in the family. These S100 proteins bind calcium (EF-hand motif), and each type is expressed in a cell-specific manner, and in a level dependent upon environmental factors. Various diseases are associated with altered S100 protein levels (cardiomyopathies, neurodegenerative and inflammatory disorders, and cancer). Note that the S100 proteins were also identified in the antibody array results as being upregulated upon contacting calcitriol.

Example 5. Effect of Calcitriol on Keratinocyte Growth

A series of HEKa cultures were treated with different concentrations of calcitriol, and the growth behavior of the HEKa cells analyzed after a pre-determined growth period. All experiments were conducted in 96-well plate format. Each well contained the same amount of HEKa cells in about 100 µL of media (usually between 2,000-5,000 cell/well). Calcitriol was dissolved in ethanol to make a stock solution. The stock solution was serially diluted 1:2 in the growth media, covering a range of between 4.0 µg/mL to about 15.5 ng/mL (9 test concentrations). About 100 µL of each test concentration of calcitriol was added a corresponding test well, resulting in a final volume of about 200 µL/well. The tested calcitriol concentrations are in the range of between 2.0-0.008 µg/mL (e.g., corresponded to columns 2 through 10 in the 96-well plate). Column 11 was used as negative control (no calcitriol). All experiments were conducted in duplicates.

Figure 2:
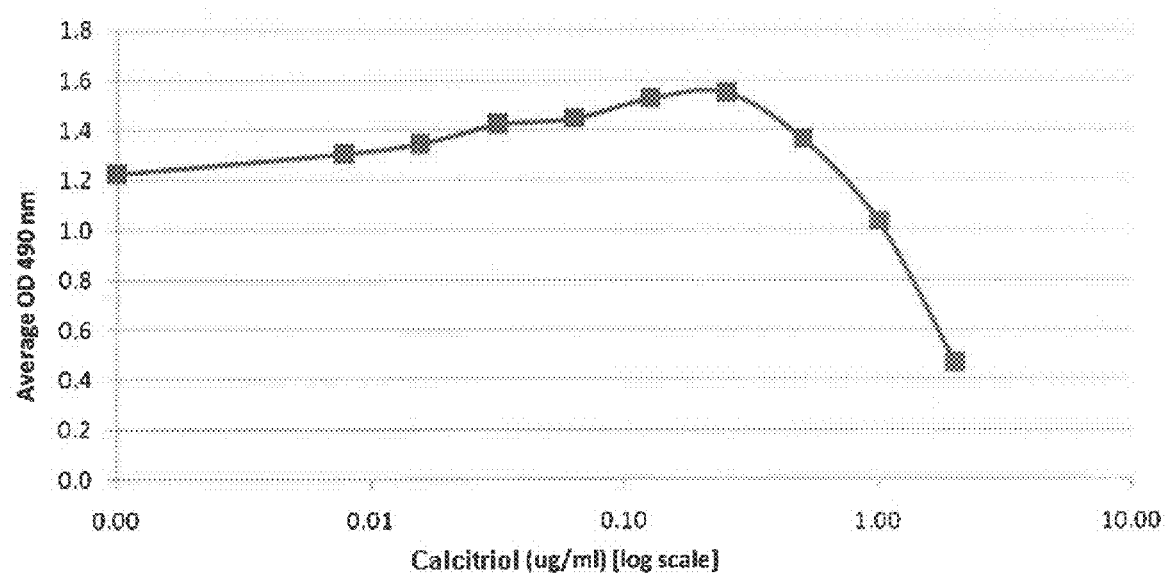
FIG. 2 shows an exemplary growth curve of HEKa cells over different concentrations of calcitriol present in the growth media. Note the log scale of the calcitriol concentration.

As shown in FIG. 2, calcitriol was titrated into HEKa cells over a concentration range from about 0.008-2.0 µg/mL. The lowest levels of calcitriol were well tolerated in the HEKa cells, and calcitriol appears to mildly stimulate HEKa cell growth (~10-20%). However, at calcitriol concentrations of about 1.0 µg/mL or greater, cell growth is inhibited. The overall dose response by the HEKa cells to calcitriol was consistent over a series of nineteen independent experiments over a period of about six weeks (data not shown).

Example 6. Effect of Calcitriol on Cancer Cell Growth

Figure 3:
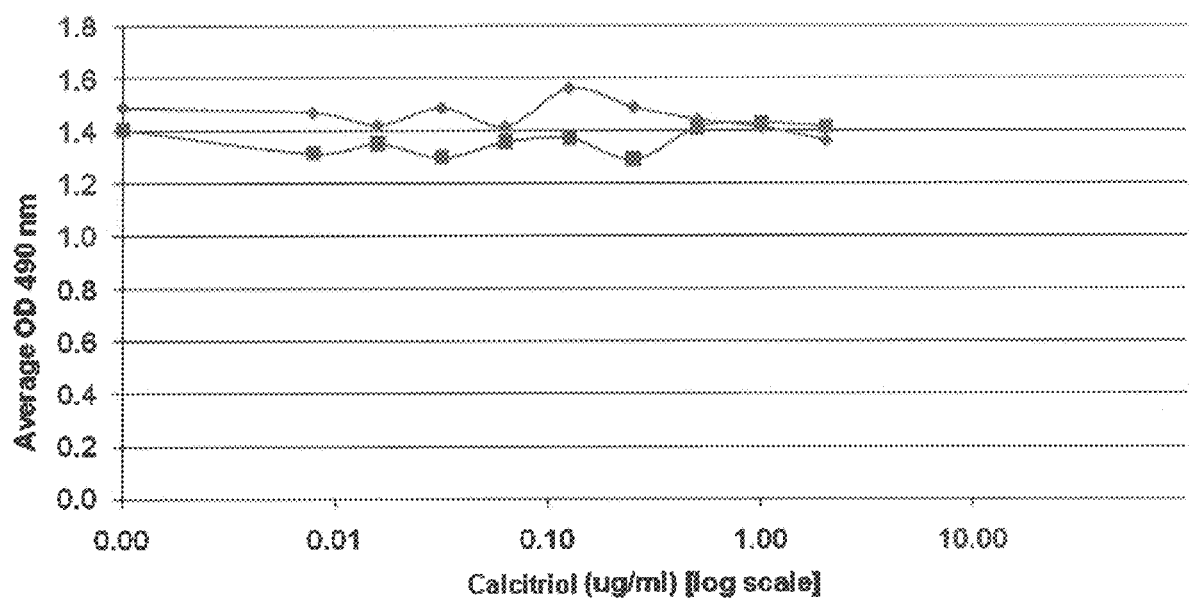
FIG. 3 shows an exemplary growth curve by the pancreatic carcinoma cell line PaCa2, which growth curve is not responsive to the presence of 0.1 µg/mL of calcitriol.

Unlike what was observed in the normal keratinocytes HEKa, no significant growth promoting or growth inhibiting effects were observed for most cancer or immortalized cell lines tested, including SkBr-3 (breast adenocarcinoma cancer, Her2 overexpressed), SKMEL-28 (melanoma), PaCa2 (pancreatic carcinoma), NCI-ES-0808, and NIH-3T3 (immortalized fibroblast). One exemplary growth curve exhibited by such cancer/immortal cell lines is shown in FIG. 3 for the pancreatic carcinoma cell line PaCa2. Note that the growth of PaCa2 was not affected over a wide range of calcitriol concentrations.

Figure 4A:
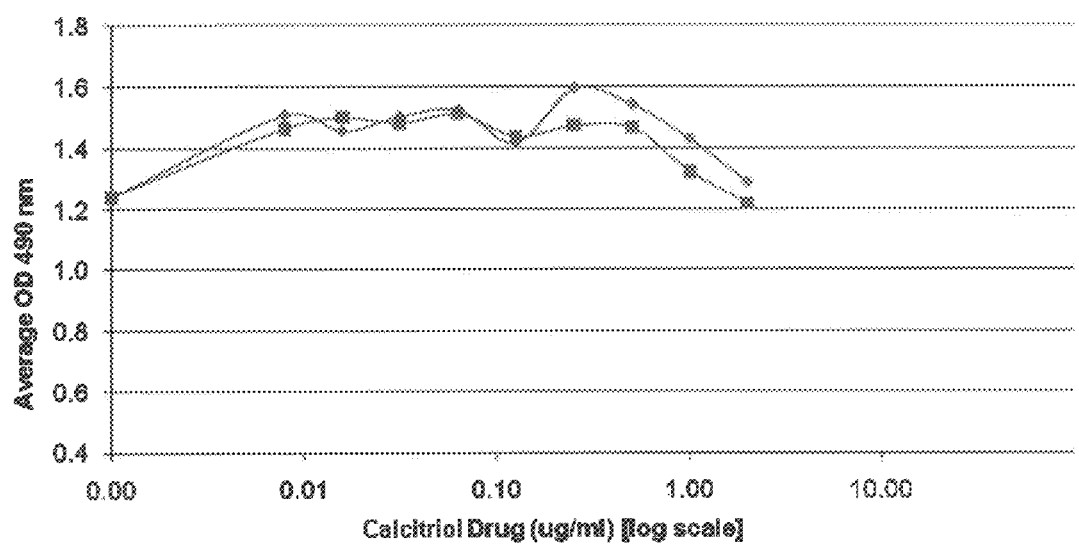
FIGS. 4A and 4B show the growth of Hep-G2 cells and MCF-7 cells, respectively, in the presence of increasing concentrations of calcitriol.
Figure 4B:
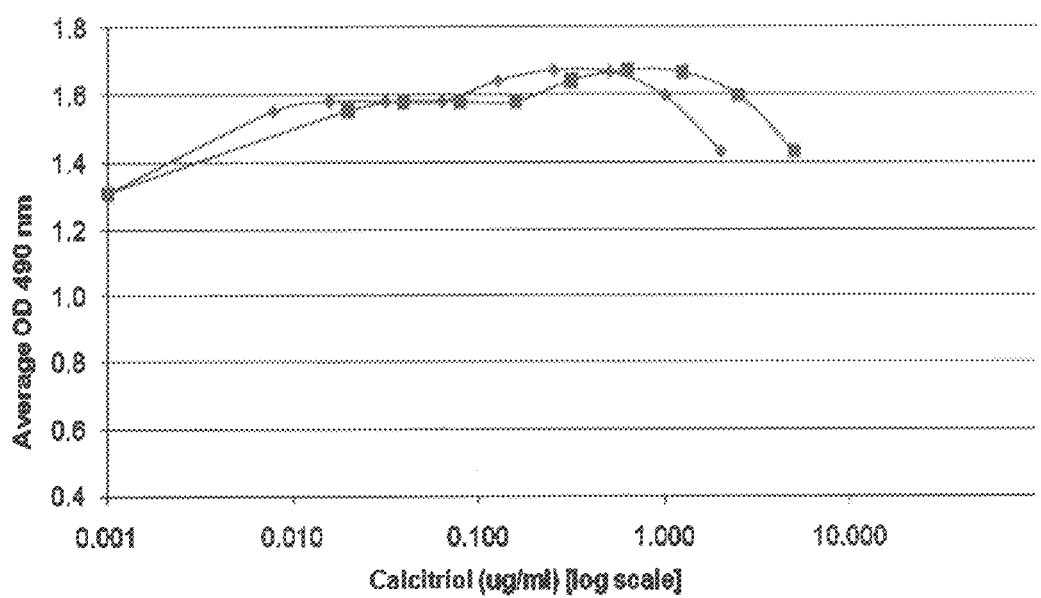
Figure 5:
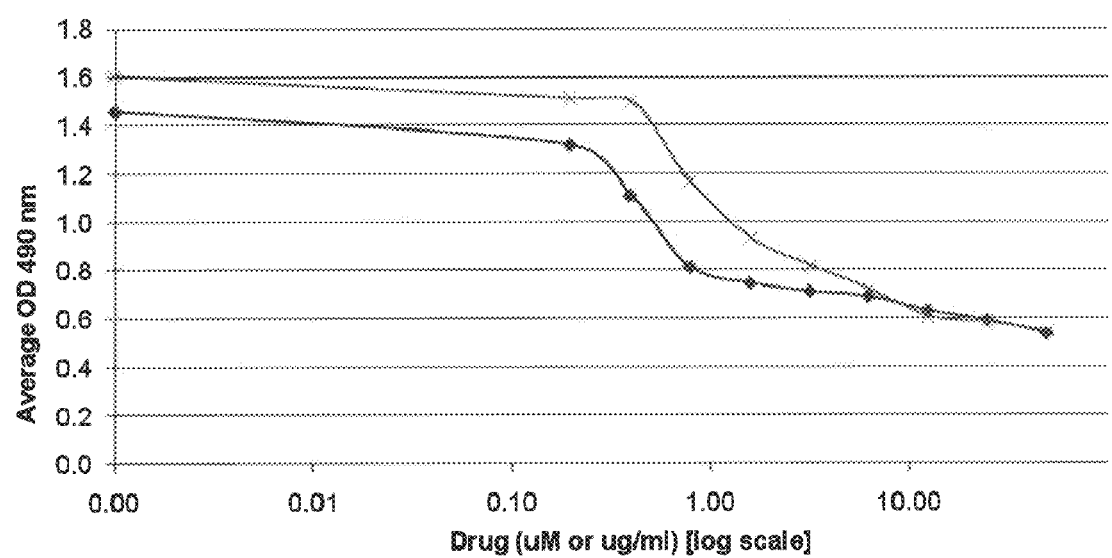
FIG. 5 shows dosing curves of erlotinib (Tarceva), an EGFR Tyr kinase inhibitor, in the absence (♦) or presence of 0.1 µg/mL calcitriol (x).
Figure 6:
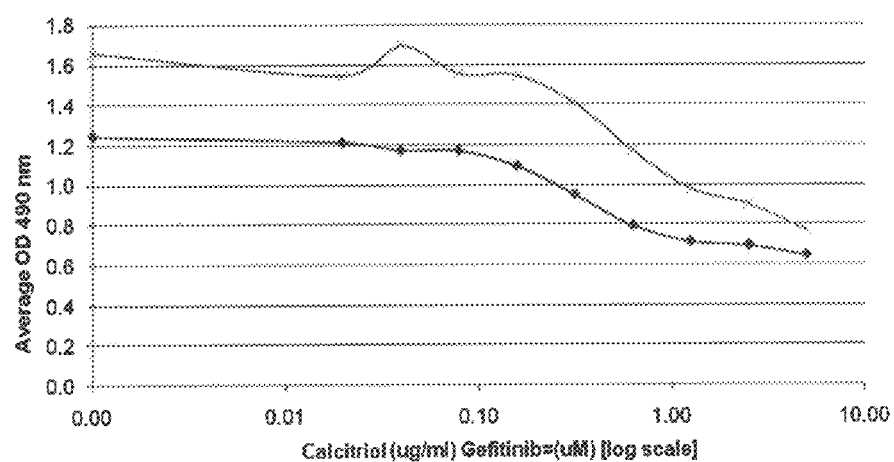
FIG. 6 shows dosing curves of gefutubub (Iressa), another EGFR Tyr kinase inhibitor, in the absence (♦) or presence of 0.1 µg/mL calcitriol (x).
Figure 7:
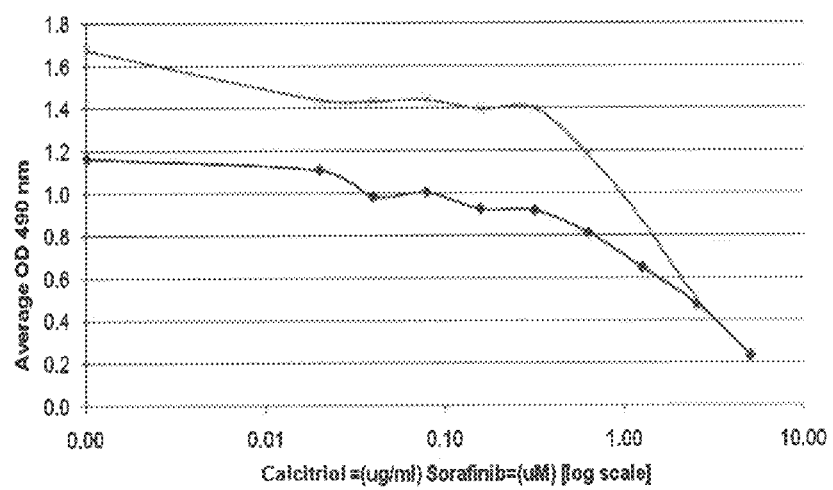
FIG. 7 shows dosing curves of sorafinib in the absence (♦) or presence of 0.1 µg/mL calcitriol (x). Sorafenib is known to inhibit several kinases (Raf, VEGF-R2, c-kit, PDGR-R).
Figure 8:
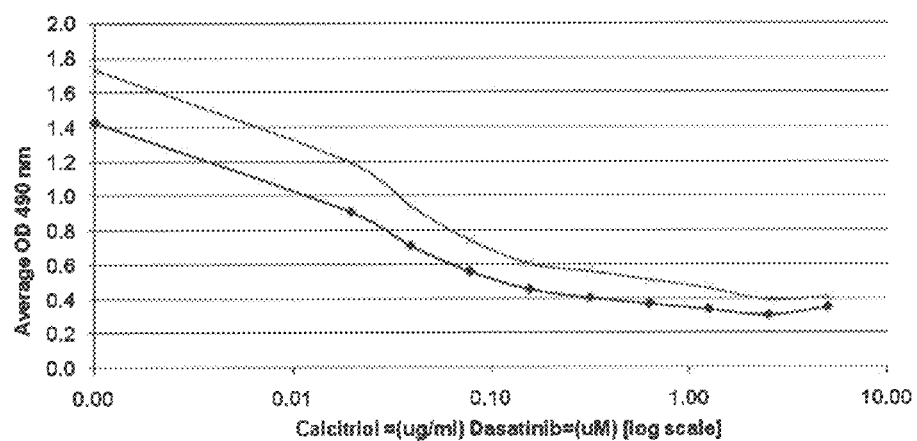
FIG. 8 shows dosing curves of dasatinib in the absence (♦) or presence of 0.1 µg/mL calcitriol (x). Dasatinib inhibits BCR/ABL Tyr kinases.
Figure 9:
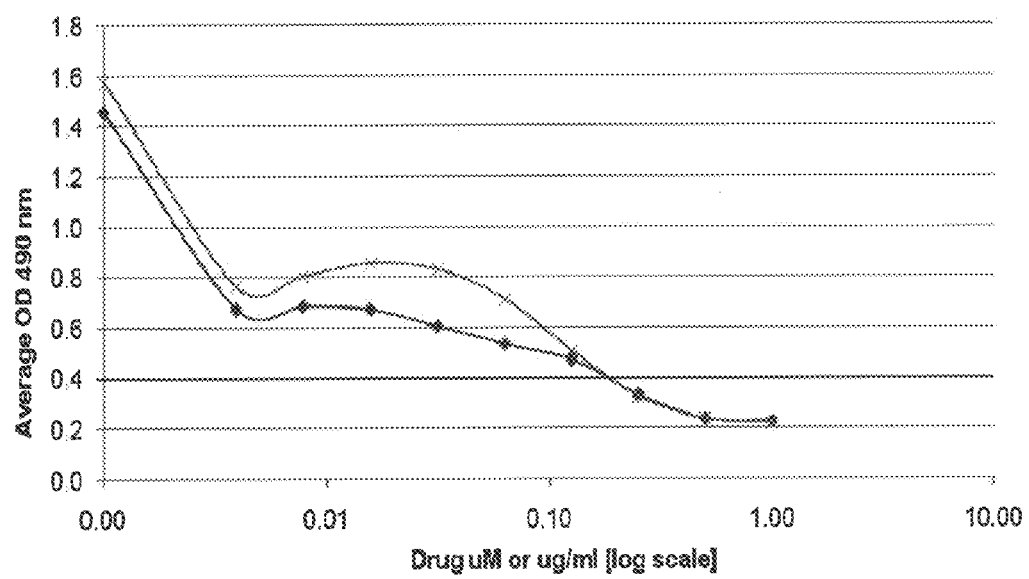
FIG. 9 shows dosing curves of staurosporin in the absence (♦) or presence of 0.1 µg/mL calcitriol (x). Staurosporin is a relatively nonspecific kinase inhibitor.

One two of the tested cancer cell lines, MCF-7 (breast cancer with p53 mutation) and HepG2 (liver cancer), similarly responded to calcitriol stimulation at low vitamin D3 concentrations (0.05-0.25 µg/mL), and calcitriol inhibition at high calcitriol concentrations (>0.5 µg/mL). See FIG. 4.

These data suggest that the subject vitamin D compounds, when applied to normal keratinocytes (such as HEKa) up to a certain concentration limit, may be able to promote the growth of these normal keratinocytes, without simultaneously promoting cancer cell growth. Exceeding the concentration limit, the vitamin D compounds may in fact inhibit the growth of normal keratinocytes.

Example 7. Protective Effect of Calcitriol on HEKa Cells Against Various Chemotherapeutic Drugs This example demonstrates that, with few exceptions, the vitamin D compounds of the invention can protect the normal keratinocytes (such as HEKa) against the cytotoxic effects of most types of front-line chemotherapeutic drugs. Specifically, seventeen anti-cancer drugs were tested to evaluate the impact of calcitriol on the cytotoxic effect of these drugs. The drug names and their respective mechanisms of actions are listed in the table below.

TABLE 7-1

Drugs tested for chemoprotective activity of calcitriol in HEKa cells

| Drug Tested | Mechanism |
|---|---|
| Doxorubicin | cytotoxic |
| 5-FU | pyrimidine antimetabolite |
| Tamoxifen | binds to estrogen receptors |
| Irinotecan | topoisomerase 1 inhibitor |
| Paclitaxel | mitotic inhibitor |
| Carboplatin | DNA alkylating agent |

TABLE 7-1-continued

Drugs tested for chemoprotective activity of calcitriol in HEKa cells

| Drug Tested | Mechanism |
| --- | --- |
| Etoposide | topoisomerase 2 inhibitor |
| Cyclophosphamide | alkylating agent |
| Cisplatin | DNA alkylating agent |
| Erlotinib (Tarceva) | EGFR tyrosine kinase inhibitor |
| Gemcitabine | pyrimidine antimetabolite |
| Staurosporin | nonspecific kinase inhibitor |
| Vincristine | microtubial inhibitor |
| Imatinib (Gleevec) | tyrosine kinase inhibitor (abl, c-kit, PDGF-R) |
| Gefitinib (Iressa) | EGFR tyrosine kinase inhibitor |
| Sorafenib | tyrosine kinase inhibitor (Raf, VEGF-R2, c-kit, PDGF-R) |
| Dasatinib | tyrosine kinase inhibitor (BCR/ABL) |

In the first series of experiments, a number of kinase inhibitor-based drugs were used in assays designed to assess the ability of 0.1 µg/mL calcitriol to provide a protective effect on HEKa cells. These include: erlotinib (Tarceva), an EGFR Tyr kinase inhibitor; gefutubib (Iressa), an EGFR Tyr kinase inhibitor; sorafenib, inhibitor of several Tyr kinases (Raf, VEGF-R2, c-kit, PDGR-R); Dasatinib, a BCR/ABL Tyr kinase inhibitor; and staurosporin, a relatively nonspecific kinase inhibitor.

The dosing curves obtained in these experiments show a general trend that, at low drug dosage levels (not unlike those affecting the skin of patients undergoing systemically delivered chemotherapy), calcitriol provided certain growth stimulation and protected the HEKa cells (see FIGS. 5-9). In addition, it appears that calcitriol has a more pronounced protective effect against more specific kinase inhibitors as compared to more non-specific kinase inhibitors.

Figure 10:
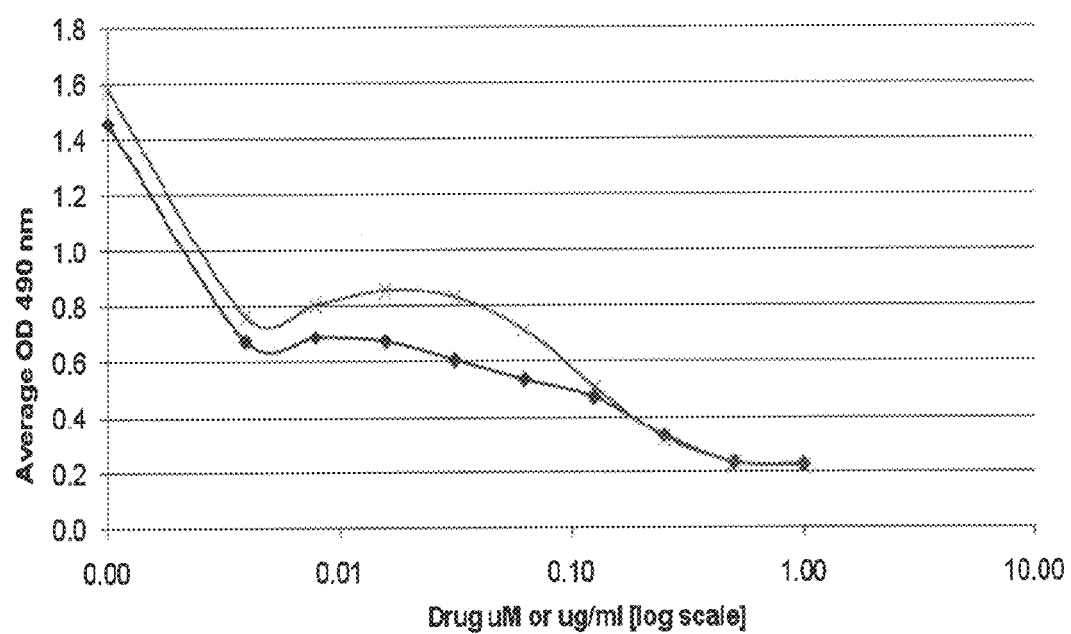
FIG. 10 shows dosing curves of cisplatin in the absence (♦) or presence of 0.1 µg/mL calcitriol (x). Cisplatin is a DNA alkylating agent.
Figure 11:
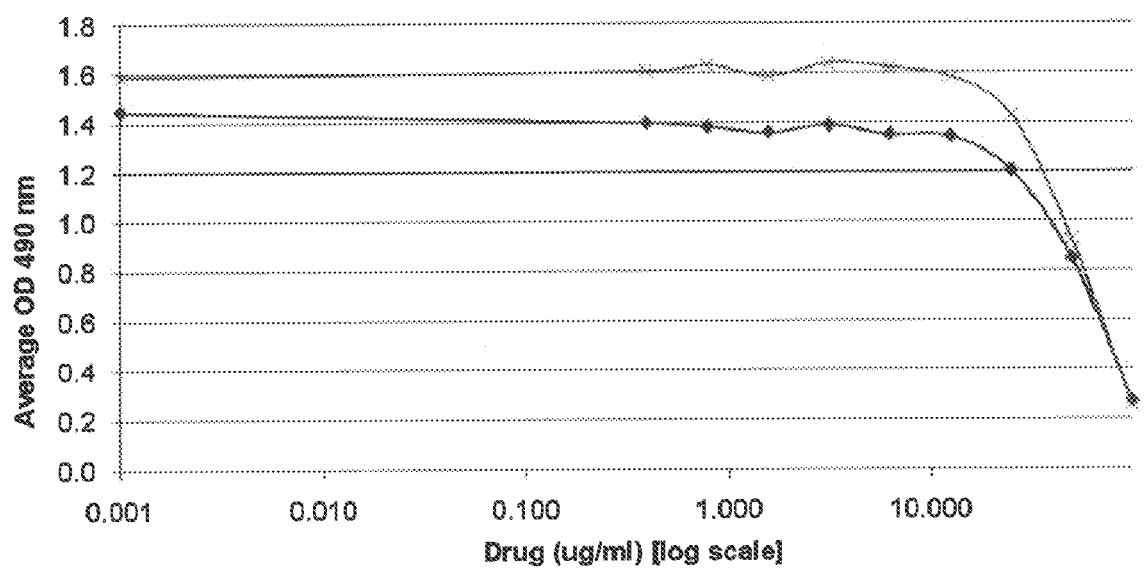
FIG. 11 shows dosing curves of carboplatin in the absence (♦) or presence of 0.1 µg/mL calcitriol (x). Carboplatin is also a DNA alkylating agent.

Similarly, calcitriol also exhibited a moderate level of protection against low dosage levels of alkylating agents, such as cisplatin and carboplatin (see FIGS. 10 and 11).

Figure 12:
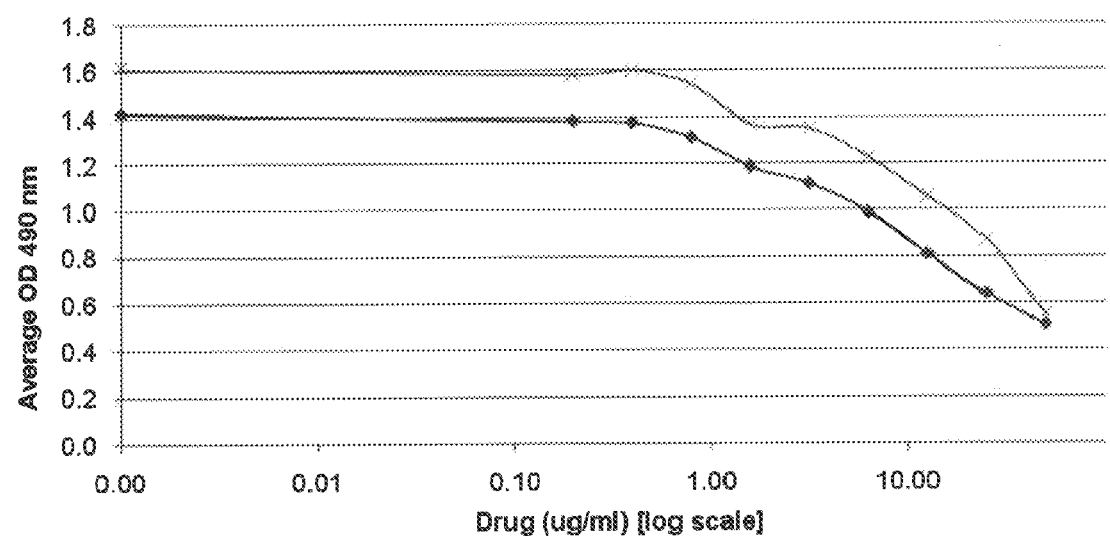
FIG. 12 shows dosing curves of irinotecan in the absence (♦) or presence of 0.1 µg/mL calcitriol (x).

Irinotecan presumably inhibits cell growth through interaction with topoisomerase I. A positive protective effect against irinotecan was also observed in the presence of calcitriol (FIG. 12).

Figure 13:
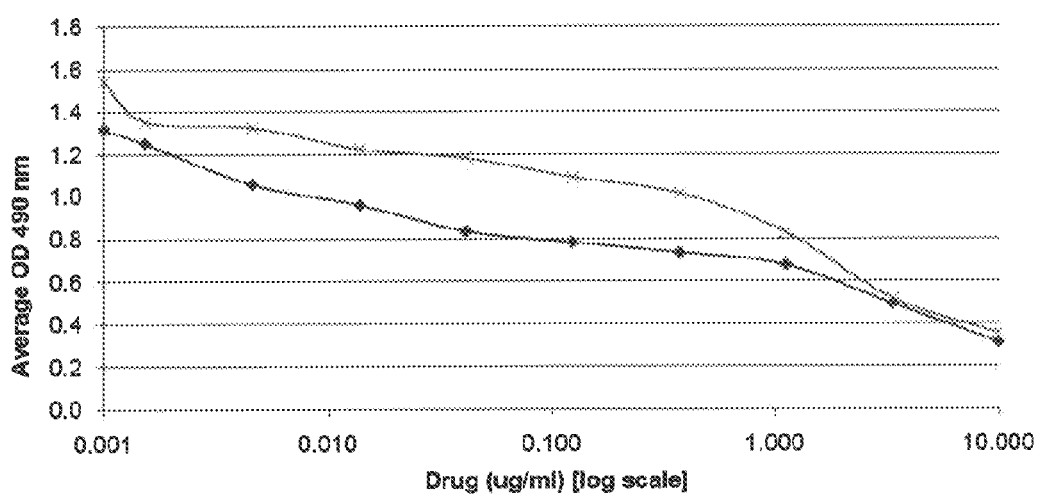
FIG. 13 shows dosing curves of paclitaxol in the absence (♦) or presence of 0.1 µg/mL calcitriol (x).

Paxlitaxol is a mitotic inhibitor. The presence of 0.1 µg/mL of calcitriol did provide some protective effects against Paxlitaxol (FIG. 13).

Figure 14:
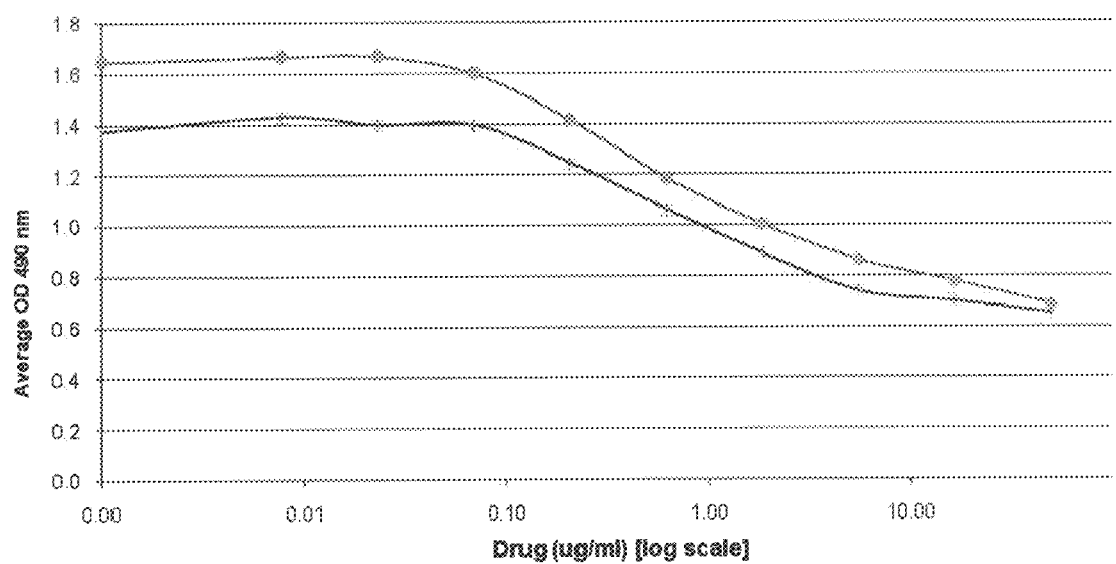
FIG. 14 shows dosing curves of 5-FU in the absence (♦) or presence of 0.1 µg/mL calcitriol (x).

Pyrimidine antimetabolite based drugs, such as 5-Fluorouricil (5-FU), act in several ways, but principally as a thymidylate synthase inhibitor. 5-FU blocks the synthesis of thymidine, which is required for DNA replication. Thus 5-Fluorouracil has been used topically for treating actinic (solar) keratoses and some types of basal cell carcinomas of the skin. At least a mild protective effect against 5-FU is seen when 0.1 µg/mL of calcitriol was present (FIG. 14).

Figure 15:
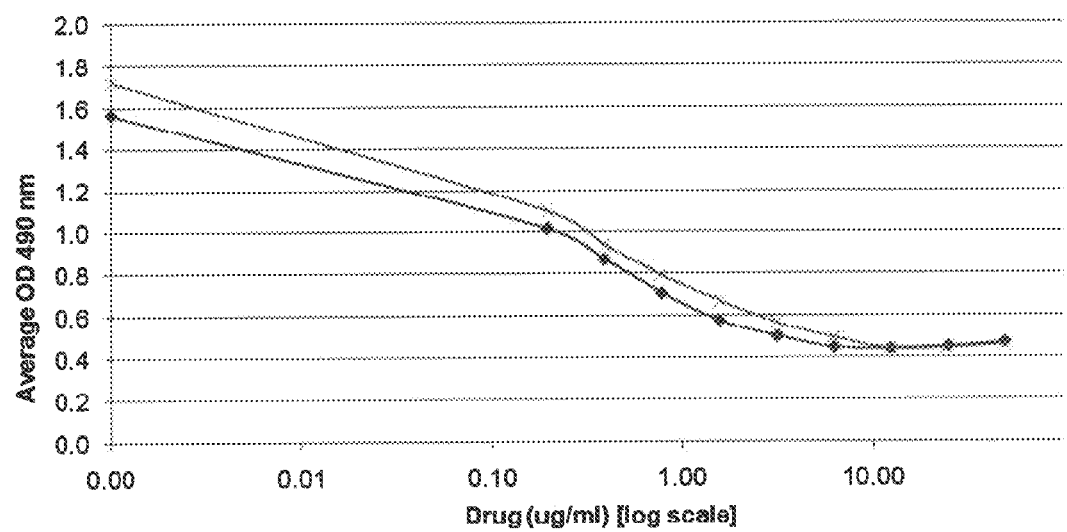
FIG. 15 shows dosing curves of gemcitabine in the absence (♦) or presence of 0.1 µg/mL calcitriol (x).

Gemcitabine is a nucleoside analog in which the hydrogen atoms on the 2' carbons of deoxycytidine are replaced by fluorine atoms. Similar to fluorouracil and other analogues of pyrimidines, gemcitabine replaces one of the building blocks of nucleic acids (which in this case is cytidine) during DNA replication. Gemcitabine is used in the treatment of various carcinomas: non-small cell lung cancer, pancreatic cancer, bladder cancer, and breast cancer. FIG. 15 shows that at least a mild protective effect against gemcitabine is seen when 0.1 µg/mL of calcitriol was present.

Figure 16:
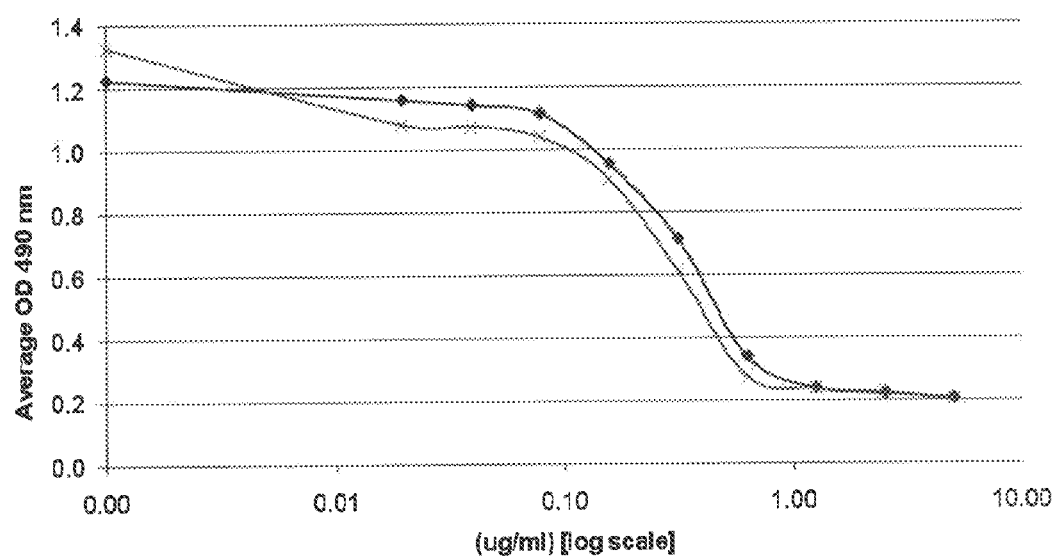
FIG. 16 shows dosing curves of doxorubicin in the absence (♦) or presence of 0.1 µg/mL calcitriol (x).
Figure 17:
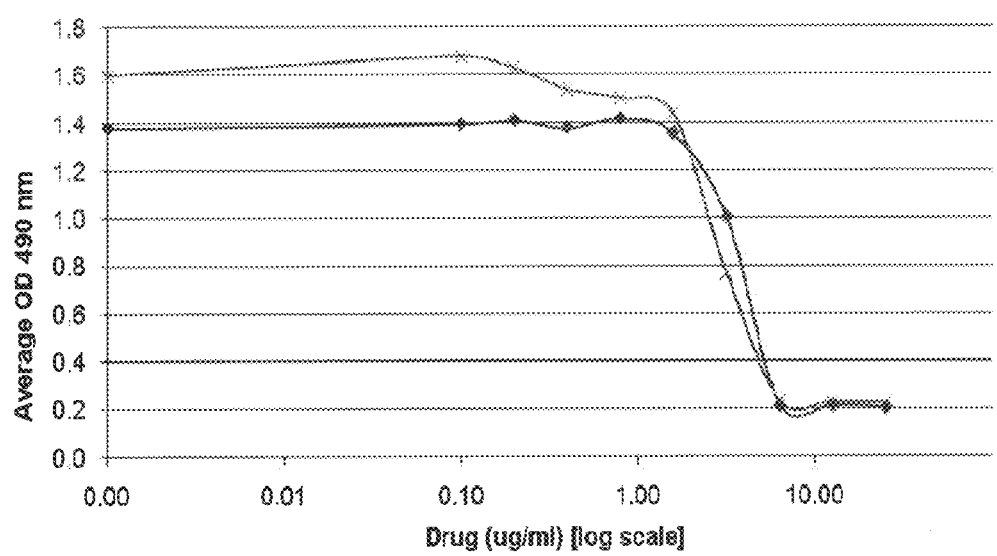
FIG. 17 shows dosing curves of tamoxifen in the absence (♦) or presence of 0.1 µg/mL calcitriol (x).

On the other hand, calcitriol did not appear to provide a significant protective effect against the cytotoxic effect of doxorubicin (FIG. 16). In addition, any protective effect against tamoxifen is weak (FIG. 17). Tamoxifen binds competitively to estrogen receptors on tumors and other tissue targets, producing a nuclear complex that decreases DNA synthesis and inhibits estrogen effects.

Consistent with the data above, data in FIG. 18 show that HEKa keratinocytes were growth stimulated by calcitriol, and some levels of protection against 5-FU was observed in the HEKa cells. Interestingly, in three tested cancer cell lines, Hep-G2, PaCa-2, and SKMEL-28, the $ED_{50}$ curves for 5-FU treatments were not significantly different from those also having 0.1 µg/mL calcitriol supplement. Note that the Hep-G2 cells were mildly stimulated by calcitriol treatment, yet its 5-FU $ED_{50}$ curve did not substantially change even in the presence of calcitriol.

Similarly, exposure of the following 4 tested cancer cell lines: Hep-G2, MCF-7, PC-3 and PaCa; 2-to 0.1 µg/mL of calcitriol for two passages did not alter the respond of these cells to other drugs (e.g., doxorubicin, cisplatin, and erlotinib).

These results above suggest that calcitriol may protect the normal keratinocytes (such as HEKa) during chemotherapy (using 5-FU, for example) without antagonizing the effectiveness of the chemotherapy against cancer cells.

Much like what was observed in HEKa cells, calcitriol did not appear to appreciably alter the cytotoxic effect of Doxorubicin against cancer/immortal cells such as SkBr-3, SKMEL-28, PaCa-2, MCF-7, NCI-ES-0808, Hep-G2, and NIH-3T3 (see FIG. 19).

In addition, possible synergistic effects of the commercial drugs with calcitriol were also explored. In these experiments, a selected commercial drug was serially diluted, starting at a concentration 4-times higher than the final desired concentration for cell incubation. Meanwhile, a stock of 0.4 µg/mL calcitriol was prepared, and then mixed with the serially diluted drug (at a ratio of 1:1). The drug/calcitriol mixture was then incubated for at least 15 minutes, and was added to the cell media (at a ratio of 100 µL to 100 µL). Thus, the final calcitriol concentration was 0.1 µg/mL.

The drug treatment period was usually three days. At the end of the three days, the background OD of the 96-well plate was read at 280 nm, before 20 µL of the "Substrate Cell Titer 96 Aqueous One Solution Reagent" (Promega) was added to each well. The plate was returned to the 37° C. incubator, and its OD at 490 nm was read each hour until an OD of approximately 1.5 was reached. The net OD increase was calculated by subtracting the pre-substrate OD reading.

The impact of the drug on the cells was calculated by comparing the OD at different concentrations in relation to the OD of the control wells (without the drug). The results of the Net OD as a function of drug concentration was plotted and used to determine $ED_{50}$ values.

Analysis of the HEKa cell results indicates that there is no interaction between calcitriol and most drugs tested, including 5-FU, doxorubicin, tamoxifen, irinotecan, paclitaxel, carboplatin, staurosporin, vincristine, cisplatin, erlotinib, gencitabine, imatinib, gefitinib, sorafinib and dasatinib. The same results also were obtained when drug combination was tested on other cells. Thus, while not wishing to be bound by any particular theory, it appears that the mechanisms of action of calcitriol and the above drugs are different.

Example 8. Pretreatment of Cells with Calcitriol: Cell-Based Assay Testing of Calcitriol in the Presence and Absence of Chemotherapy Drugs The above cell-based assays to evaluate cell viability were used in the example to assess the potential protective effect of calcitriol against the action of selected chemotherapy drugs. Each cell line was allowed to grow in the presence of 0.1 µg/mL calcitriol for two cell passages. Then these pretreated cells were utilized to set up the cell-based assay. In addition, untreated cells were used to establish a parallel experiment under duplicate drug/calcitriol concentrations. This allowed side-by-side comparison of the potential effects of prolonged calcitriol exposure prior to the administration of the chemotherapy drug.

After each of the five cell lines were grown for two cell passages in the presence of 0.1 µg/mL calcitriol, only the HEKa cells were significantly affected in their overall growth and morphology. The four cancer cell lines continued to grow and were not altered in their general morphological appearances. However, the HEKa cells stopped growing after prolonged calcitriol exposure, and their morphology changed into one that is elongated in one direction, as opposed to a more branched appearance prior to calcitriol treatment. For this cell line, a new batch of cells were started and were exposed to only a single passage in the presence of calcitriol, prior to testing in the presence of the chemotherapy drugs.

Three commonly used chemotherapy drugs (doxorubicin, cisplatin and erlotinib) were selected to evaluate calcitriol treated cells. The possible synergistic or protective effects of the commercial drugs with calcitriol were explored. In these experiments, the commercial drugs were serially diluted, starting at a concentration 4-times higher than the final desired concentration for cell incubation. A stock of 0.4 µg/mL of calcitriol was prepared and added to the serially diluted drug (at a 1:1 ratio). The mixture of drug and calcitriol was incubated for at least 15 minutes, and was added to the cells (at a ratio of 100 µL to 100 µL). Thus, the final calcitriol concentration was 0.1 µg/mL.

The assay was carried out according to the previously described method in order to provide consistency and allow direct comparison. The result was based upon measurement of the total number of viable cells. The results (not shown) indicate that calcitriol pretreatment was not necessary for the chemoprotective effect on the cell cultures. The results were nearly identical between the pre-treatment group and the simultaneous treatment group. Thus, a topical application of calcitriol could be applied at the same time as the systemic delivery of the chemotherapy. A staged application is not required.

Example 9. Protection from Chemotherapy-Induced Alopecia (CIA) by a Novel Calcitriol Formulation Alopecia is one of the most distressing side-effects of chemotherapy, for which there is no current therapeutic intervention. The neonatal rat has been demonstrated to be an excellent model in which to study Chemotherapy-Induced Alopecia (CIA), since the anagen hair follicle pattern is similar to that of humans.

In the present study, the secosteroid calcitriol (USP grade) was delivered in a topical formulation (40% (w/w) propylene glycol, USP; and 60% (w/w) dehydrated alcohol, 200 proof, undenatured USP) to treat/prevent CIA, in a dose and time-dependent manner.

Specifically, Long Evans and Sprague Dawley rats with pups were purchased from Harlan Laboratories, Inc. They were housed and fed according to applicable animal handling rules and regulations. Pups were allowed to acclimate for 48 hours prior to the start of experiments. The secosteroid calcitriol formulation (supra) or vehicle control (no calcitriol) was applied topically over the head and neck area daily, starting on day 5 for 6 consecutive days. Rats were isolated from their littermates and mother for 6-hour periods of time. Subsequently, the treated area was cleaned with soap and water and pups were returned to their litters. On day 13, rats either received etoposide (1.5 mg/kg daily for 3 days) or cyclophosphamide (CTX) (37.5 mg/kg once) or combination cyclophosphamide (35 mg/kg once) and doxorubicin (2.5 mg/kg daily for 3 days). All chemotherapies were purchased from Sigma and were given intraperitoneally (i.p.) in a total volume of 0.1 mL. Alopecia was recorded 10 days after the last dose of chemotherapy.

For experiments in which rats were transplanted with chloroleukemia, on Day 5 after birth, rats were randomly divided into three groups of 45 each. All rats received $1 \times 10^5$ chloroleukemic cell line MIAC51 (i.p.) in 0.1 mL of serum free (SF) RPMI. MIAC51 were cultured in RPMI 1640 supplemented with L-glutamine and 10% fetal bovine serum at 37° C. in a 5% $CO_2$, 100% humidity incubator. Cells were grown to 50% confluency ($1.5 \times 10^6$ mL) collected in 50 mL conical tubes, centrifuged at 600 g×10 min. at room temperature and resuspended in SF-RPMI at a concentration of $1 \times 10^6$/mL. Group 1 rats received no further treatment. Group 2 rats received topical vehicle and CTX on day 13. Group 3 rats received the topical calcitriol formulation (0.1 µg) and CTX on day 13. Topical applications were performed as described above.

On day 23 after birth, a sample of blood was taken from all rats and differentials performed. Rats with leukemia were sacrificed, rats without leukemia were kept and a second differential performed on day 31, at any point if leukemia was detected, animals were sacrificed by $CO_2$ asphyxiation.

Results demonstrated that full body alopecia was observed in the group that received etoposide. In contrast, in the rats treated with 0.1 µg of calcitriol for 6 hours, partial localized protection was observed in all the animals. In the group receiving 0.3 µg calcitriol, total body protection was achieved. See FIGS. 20A and 20B.

In the group that received cyclophosphamide, control rats became totally alopecic, while the rats that received 0.1 µg calcitriol achieved similar protection as observed with etoposide. Likewise, administration of 0.3 µg calcitriol resulted in full body protection in cyclophosphamide-treated rats. See FIG. 21. Similar results using other chemotherapy or combination chemotherapy regimens are shown in FIGS. 22A, 22B, 22C and 23.

In a separate experiment in which rats were transplanted with chloroleukemia, preliminary results have not shown protection of the cancer cells from cyclophophamide by the topical application of calcitriol. See FIG. 24.

In conclusion, pretreatment with calcitriol in the subject formulation offered protection against CIA without protecting cancer cells. Topical calcitriol prevented CIA, in a dose dependent manner, from CIA induced by single as well as combination chemotherapy. In addition, topical calcitriol prevented CIA while not protecting the cancer cells from the cytotoxic effects of chemotherapy.

Example 10. Protection of CIA by Topical Calcitriol in Chloroleukemic Rats Receiving Multi-Chemotherapy Regimens This study verifies the protective effect of the topical calcitriol solution in an animal model of multi-course chemotherapy-induced alopecia. The rats used in the study bear MIAC51, a rat chloroleukemia cell line developed by gastric instillation of 20-methylcolanthrene and subsequent injection of the chloroleukemic cells into rat neonates. The MIAC51 cell line causes malignant myelogenous leukemia with features of human chloroleukemia (leukemia, leukemic ascites and chloroma formation). See Jimenez et al., *Science* 238: 1278-1280 (1987).

To date, there is no effective in vitro or non-vertebrate model to test chemotherapy-induced alopecia (CIA). Amongst the most used models, the neonatal rat developed by Jimenez et al. has demonstrated a direct correlation with human (*Int J Cancer* 1996; 65: 97-103, incorporated by reference). Subsequently, a rat model was developed in which a second anagen stage can be induced by clipping hair and thereby allow for testing multiple courses of chemotherapy. This model can be used to test frequently used alopecic chemotherapies, including cyclophosphamide, doxorubicin, paclitaxel, etoposide, and cytarabine, and combinations thereof.

When testing protective agents for chemotherapy-induced alopecia, it is paramount to determine whether the test article will protect the hair follicles and also the cancer cells from the chemotherapy and/or interfere with therapy. The neonatal rat model of leukemia, developed by Jimenez et al., provides an opportunity to simultaneously test any effect of the vitamin D compound on the development of leukemia, the treatment of leukemia, potential interaction with chemotherapeutic agents, and the effect of the vitamin D compound on prevention of chemo-induced alopecia. This model also answers the question of whether multiple cycles of the test agent in the same animals will result in the protection of hair follicles multiple times. In addition, by using the pigmented Long Evans rat, the study also allows the determination of whether the test agent protects hair color.

The calcitriol formulation is a clear, anhydrous liquid containing USP-grade calcitriol in a vehicle containing USP-grade propylene glycol (40% w/w) and anhydrous absolute ethanol, 200 proof (60% w/w). The concentration of calcitriol in these studies is ~0.2 µg/100 µL (2 µg/mL). The test article is received on ice, and is immediately stored at 4-5° C. upon arrival. The lot will then be subdivided into 4.5 mL tubes while being maintained on ice. Since animal groups will be no smaller than 40 per variable, each 4.5 mL units of the test article will be packaged in a polypropylene tube at 4-5° C. with the lot number. The 4.5 mL tubes of test article will be kept in dark boxes and only the amount needed per experiment will be taken out of the refrigerator. A sample of test article packaged in 4.5 mL tube will be assayed at a regular interval to determine calcitriol levels. At the time of the experiments, tubes will be kept on ice while rats are treated.

The vehicle is comprised of USP-grade propylene glycol (40% w/w) and USP-grade anhydrous and undenatured absolute ethanol, 200 proof (60% w/w). At the time of the experiments, the control vehicle is handled exactly as the test article.

Both the test article as well as the vehicle itself are tested. Each test group consists of 40 animals, which is statistically significant for this study. This number includes model attrition, and accounts for any eventuality which reduces the number of animals. All animals are injected with MIAC51 when they are 5 days of age. Five (5) chemotherapy regimens are tested: cyclophosphamide, cyclophosphamide/doxorubicin, cyclophosphamide/doxorubicin/cytarabine, cyclophosphamide/paclitaxel/etoposide and doxorubicin/paclitaxel/etoposide. Test groups are: no chemotherapy, chemotherapy alone, chemotherapy+vehicle, chemotherapy+test article=160 animals per chemotherapy regimen. Therefore, the final estimated number of animals used are as follows: 5 combination chemotherapy regimens×160 animals=800 pups/rats. For experiments using the second anagen phase adult rat model, only animals that are cancer-free (e.g., those who have survived chemotherapy) are used, while animals evidencing early signs of leukemia are euthanized.

Culture of the Shay's Chloroleukemia MIAC51 Cell Line:

MIAC51 is cultured in a 5% $CO_2$ incubator with 100% humidity at 37° C. as previously described (*Science* 1987; 238:1278-80). Cells are grown in non-tissue culture-treated flasks (Falcon) in RPMI 1640 medium (Gibco Invitrogen, Carlsbad, Calif.) supplemented with L-glutamine and 10% fetal bovine serum (Gibco Invitrogen, Carlsbad, Calif.). Prior to the injection of cells into the animals, they are grown to 50% confluency and collected in conical tubes. Cells are then centrifuged at 600 g for 10 minutes at room temperature, and resuspended at a concentration 1×106 in RPMI 1640 without fetal bovine serum. The cell suspension is then transferred to 29 gauge (ga). ½ cc insulin syringes under sterile conditions.

Injection of MIAC51:

All pups are five days old upon injection of MIAC51 and are manually restrained. The right leg is gently pulled and the area is cleaned with an alcohol swab. MIAC51 is then injected intraperitoneally. The needle, path and cells in the syringe are sterile and a fresh syringe is used for each injection. Development of early signs of leukemia are usually observed during Days 21-33. Therefore, blood smears are performed on Days 23 and 31. Only animals that are cancer-free are shaven on day 31, while the rest are euthanized.

Test and control article administration in the first anagen stage in the neonatal rat: Each litter is administered either vehicle or test article topically on the head and the neck area of approximately 2 $cm^2$. For 5- and 6-day old rats, 100 µL is applied in 4 aliquots of 25 µL 4 times to account for their smaller size. Test article or vehicle is applied with a calibrated micropipette using 200 µL sterile tips. Once test article or vehicle is on the surface of the head, it is rubbed in with gloved finger until fully absorbed Immediately after, another aliquot is applied to the head and the process is repeated until 100 µL total test article or vehicle is applied. On 7-, 8-9- and 10-day-old animals, 50 µL aliquots are applied twice. In older animals, 100 µL can be applied in one dose. Application of the testing article is applied to the head and neck, and rubbed in with a solvent-resistant nitrile glove for 10 seconds with the right index finger. The rationale behind this application regime is that at different ages, the saturation rate may differ, and the delivery of the test article or vehicle may also differ. Once the solution has completely penetrated the skin, pups will be maintained isolated in cages with specially designed isolated compartments for 6 hours. Pups are then washed with mild laboratory hand soap (Soft-Cide EC, VWR international) and carefully dried with paper towels.

Administration of Chemotherapy in the First Anagen Stage in the Neonatal Rat:

Forty pups receive each chemotherapy regime, 40 receive each chemotherapy regime and test article, and 40 receive each chemotherapy regime and vehicle. As a control, 40 animals do not receive chemotherapy. An average of the weights of each litter is obtained and is used to prepare a suitable concentration of chemotherapy. Chemotherapies are injected intraperitoneally in a volume of approximately 100 µL according to the weight of the animals using 29 ga. ½cc insulin syringes. When injecting, the right leg of each pup is gently pulled and the area is cleaned with an alcohol swab.

Test and Control Article Administration in the Second Anagen Stage of the Adult Rat:

Survivors that have been demonstrated to be cancer-free on day 31 according to the hematological analysis of blood smears are manually restrained and shaven in the head and neck area (2-3 cm$^2$). Nine days later, when rats are 40 days old to 45 days old inclusive, either vehicle or test article is applied to the head and the neck area. An amount of 100 µL is applied in one dose to the head and neck, and rubbed in with a solvent-resistant nitrile glove for 10 seconds with the right index finger. Once the solution has completely penetrated the skin, single rats are maintained isolated in cages. Rats are then washed with mild laboratory hand soap (Soft-Cide EC, VWR international) and carefully dried with paper towels.

Administration of Chemotherapy in the Second Anagen Stage Adult Rat:

Each group receives 1 of 5 different chemotherapy regimens, starting on day 47 and ending on day 53 for those receiving combination cytarabine. An average of the weights is obtained and is used to prepare a suitable concentration of chemotherapy. Chemotherapies are injected intraperitoneally in a volume of approximately 100 µL according to the weight of the animals using 29 ga. ½cc insulin syringes. For administering chemotherapy, rats are manually restrained using no anesthesia. The injection area is cleaned with an alcohol swab.

Route of Administration:

Test article and vehicle are applied dermally. Chemotherapies are injected intraperitoneally.

Frequency and Duration of Administration and Dose Levels and Volumes:

The test article and vehicle are administered daily for 6 days for both the first and second anagen cycle. Test article contains a concentration of 2 µg/mL calcitriol in the propylene glycol/ethanol, and the vehicle contains only the propylene glycol/ethanol vehicle. Chemotherapies are given based on weight in a volume of approximately 100 µL intraperitoneally.

Visual Observation and Grading of Alopecia:

Total (head and neck) or complete body alopecia is graded using the following scale: 0=No Alopecia; 1+=0-25% Alopecia; 2+=25-50% Alopecia; 3+=50-75% Alopecia; 4+=75-100% Alopecia. The visual observation scale is used daily to grade alopecia while performing routine cage observations. In addition, this scale complements the photographic documentation once the entire litter or the adult rats have lost the hair.

Example 11. A Dermal Absorption Study: Topical Application of Calcitriol Solution in Gottingen Minipigs® and Quantification of Calcitriol in Ex Vivo Porcine Skin Pigs are frequently used in toxicity studies involving the dermal route of delivery because the skin of the pig is very similar to that of humans Therefore, pigs were used in this study to evaluate the dermal tolerability and dermal penetration of the calcitriol topical formulation in Gottingen Minipigs®, following 7 days of dermal administration.

One treatment group of three male and three female Gottingen Minipigs® was administered the test or placebo article dermally to five separate administration sites at dose concentrations of 0 (placebo), 1, 3, 10, and 30 µg/mL. An additional treatment group of one male minipig was administered the test or placebo article dermally to two separate administration sites, at dose concentrations of 0 (placebo) and 100 µg/mL, respectively. The placebo or test article was administered at an application rate of 4 mg/cm$^2$ (equivalent to 144 mg in a 6 cm×6 cm test area, or 166 µL of test solution, which contains the active ingredient at various concentrations and vehicle, per application site to both groups twice daily approximately 6 hours apart, for 7 days during the study.

Observations for morbidity, mortality, injury, and the availability of food and water were conducted twice daily for all animals. Clinical observations were conducted daily. Evaluation of skin reaction was conducted pretest and daily prior to dosing. Body weights were measured and recorded pretest and terminal (Day 7). Physical examinations were conducted at pretest. At study termination, necropsy examinations were performed and sections of treated and untreated skin were collected and preserved. Microscopic examination of each of the skin sites, as well as an untreated skin site near the treated sites, was conducted.

Results show that dermal administration of the calcitriol topical formulation at concentrations of 0, 1, 3, 10, 30, and 100 µg/mL to Gottingen Minipigs® was well tolerated. No effect of treatment was seen on survival, clinical findings, dermal irritation, body weights, macroscopic or microscopic examination of the skin at any of the treatment sites (data not shown). The data from the tissue distribution study indicate that calcitriol was measurable in most stratum corneum and other parts of the epidermal samples, but not in the dermal sample (with the single exception of the 100 µg/mL dose application to a single male minipig). In this set of experiments, males appeared to demonstrate greater calcitriol tissue levels than females. The clearest applied dose correlation to tissue level was observed in the epidermis, with a near linear increase with increasing calcitriol concentrations from 3 to 100 µg/mL.

Specifically, the placebo (a 40/60 mixture (w/w) of propylene glycol (USP) and ethanol (undenatured) anhydrous, 200 proof—U.S., USP), and the calcitriol topical formulation, were used at the pre-formulated concentrations of 1, 3, 10, 30, and 100 µg/g. The test article was administered neat (undiluted). Formulations of the placebo and test articles were dispensed for each required concentration once for daily use, and were stored at room temperature.

A total of three male and three female experimentally naïve Gottingen Minipigs® (approximately 4 to 5 months of age) were received from Marshall BioResources, North Rose, N.Y. An additional male (approximately 4.5 months of age at receipt), was later transferred in from the stock colony. Using a simple randomization procedure, four male and three female animals (weighing 11.75 to 15.55 kg and 14.50 to 16.65 kg, respectively, at randomization) were assigned to the placebo and treatment groups. The placebo and test articles were administered dermally twice daily approximately 6 hours apart for 7 days during the study. The dose concentrations were 0, 1, 3, 10, 30, and 100 µg/mL, and administered at an application rate of 4 mg/cm$^2$ (equivalent to 144 mg or 166 µL of test solution). Prior to initiation of administration (Days −4 and −5 for Groups 1 and 2, respectively), the hair was clipped from the application sites using an electric clipper. Care was taken to avoid abrading the skin. The dorsal surface of each animal was divided into five application sites for Group 1 and two application sites for Group 2. Each application site was approximately 6×6 cm with at least a 2 cm space between each site. The placebo and test article formulations were uniformly applied over the specified application site with a glass stirring rod or appropriate instrument. Prior to dosing, the residual test article from the previous dose was gently removed using a soft paper towel (i.e., WyPall®) moistened with tap water.

At the end of the study, the skin was reflected from a ventral midline incision, and sections of treated and untreated skin were collected and preserved. Sections of each 6×6 cm dosing site were first thoroughly surface washed with a mild soap and water mixture (e.g., 1% Ivory Soap in water or equivalent) to remove any residual topical test formulation. The washed skin sections were then wiped clean with ethanol, and were excised down to and including the adipose layer. If the area to be excised is larger than the dosed area, the dosed area was demarked with indelible ink to delineate the skin area that was dosed. The 1.5 cm×1.5 cm sections were laid flat, wrapped in two layers of Saran wrap (or equivalent) and flash frozen in liquid nitrogen. The samples were stored at −70° C. and shipped on dry ice via overnight courier for analysis. Each skin section was identified as appropriate (e.g., animal identification, study number, date, etc).

Upon arrival at the analysis site, skin sections were placed in water tight plastic bag and thawed by emersion in warm water (~30° C.-35° C.). Each skin section was gently rinsed with distilled de-ionized water to remove any residual test article and blood. All subcutaneous tissue (e.g., adipose) was removed by manual scalpel ablation. Within the central region of the dosed area, four individual 1 $cm^2$ circles (replicates) were demarked, and each site was subsequently identified and the actual area recorded. The replicate test sites were then excised from the skin sheet using a 1 $cm^2$ punch. The skin sections were weighed and the weight recorded. Each replicate demarcated area was tape stripped (Transpore™, 3M) sufficient times (~10-~20) until approximately 10%-25% of the area's surface demonstrated glistening. This process removed the stratum corneum and any residual surface dose.

Following tape stripping, the skin was separated into epidermis (sans stratum corneum, simply referred to herein after as "epidermis") and dermis by heat exposure to 60° C. for approximately 1-1.5 minutes. The skin layers were then teased apart using fine-tipped forceps or scalpel. The epidermis and dermis were weighed and the weight recorded.

For extraction, all skin samples were extracted in 1 mL of absolute ethanol (Sigma-Aldrich, USP/NF Grade). Tape strips were extracted in 5 mL acetonitrile (EMD, HPLC Grade). All extractions were conducted at room temperature for approximately 24 hours. An amount of 500 μL of the tape strip extract was dried by vacuum centrifugation and reconstituted in 100 μL absolute acetonitrile. The epidermal extract was also dried and reconstituted in 100 μL 80:20 ethanol:water.

Quantification of calcitriol was by reverse phase High Performance Liquid Chromatography (HPLC) with ultraviolet and mass spectroscopy detectors. Lower limit of detection is estimated at 0.4 ng/mL.

The results for the quantification of calcitriol, from stratum corneum (tape strips), epidermis and dermis are summarized in Tables 11-1 to 11-4. FIGS. 25A and 25B illustrate the levels in the stratum corneum and epidermis, respectively, and FIG. 26 illustrates the epidermal levels in the males only. Stratum corneum data are provided in two different units, ng/$cm^2$, to reflect the amount of calcitriol recovered in the tape stripped samples as a function of the sample area, and as estimated μg/mg tissue. However, the concentration reported, as μg/mg, is determined by the differential total sample weight before layer separation minus the weights of the epidermis and dermis for that sample (rather than by actual weight due to its adherence to the tape strips). Epidermal and dermal samples are reported as tissue concentration (ng/mg) using the amount measured from the sample divided by actual wet weight of the skin layer.

TABLE 11-1

Stratum Corneum (ng/$cm_2$) Mean ± SD of Calcitriol Recovered (n = Number of Animals [4 replicates/animal])

| Treatment | Male Minipigs | Female Minipigs |
|---|---|---|
| Untreated | 0 ± 0* (1) | na |
| Placebo | 30.2 ± 35.0 (4) | 0 ± 0 (3) |
| 1 μg/mL | 56.1 ± 17.4 (3) | 0.76 ± 1.3 (3) |
| 3 μg/mL | 62.4 ± 7.91 (3) | 1.12 ± 1.49 (3) |
| 10 μg/mL | 59.6 ± 14.1 (3) | 1.65 ± 1.80 (3) |
| 30 μg/mL | 54.6 ± 32.5 (3) | 20.2 ± 11.7 (3) |
| 100 μg/mL | 118.1 ± 11.4 (1) | na |

*Zeros indicate results to be below the Lower Limit of Detection.
*na = not applicable

TABLE 11-2

Estimated Stratum Corneum (ng/mg) Mean ± SD of Calcitriol Recovered (n = Number of Animals [4 replicates/animal])

| Treatment | Male Minipigs | Female Minipigs |
|---|---|---|
| Untreated | 0 ± 0* (1) | na |
| Placebo | 0.92 ± 1.07 (4) | 0 ± 0 (3) |
| 1 μg/mL | 1.54 ± 0.79 (3) | 0.03 ± 0.05 (3) |
| 3 μg/mL | 1.63 ± 0.25 (3) | 0.04 ± 0.06 (3) |
| 10 μg/mL | 2.02 ± 0.39 (3) | 0.05 ± 0.04 (3) |
| 30 μg/mL | 1.51 ± 0.89 (3) | 0.64 ± 0.37 (3) |
| 100 μg/mL | 4.52 ± 1.21 (1) | na |

*Zeros indicate results to be below the Lower Limit of Detection.
*na = not applicable

TABLE 11-3

Epidermis (ng/mg) Mean ± SD of Calcitriol Recovered (n = Number of Animals [4 replicates/animal])

| Treatment | Male Minipigs | Female Minipigs |
|---|---|---|
| Untreated | 0 ± 0* (1) | na |
| Placebo | 0.12 ± 0.23 (4) | 0 ± 0 (3) |
| 1 μg/mL | 0.16 ± 0.28 (3) | 0 ± 0 (3) |
| 3 μg/mL | 0.14 ± 0.23 (3) | 0 ± 0 (3) |
| 10 μg/mL | 0.23 ± 0.20 (3) | 0.02 ± 0.04 (3) |
| 30 μg/mL | 0.38 ± 0.33 (3) | 0.34 ± 0.24 (3) |
| 100 μg/mL | 2.09 ± 1.0 (1) | na |

*Zeros indicate results to be below the Lower Limit of Detection.
*na = not applicable

TABLE 11-4

Dermis (ng/mg) Mean ± SD of Calcitriol Recovered (n = Number of Animals [4 replicates/animal])

| Treatment | Male Minipigs | Female Minipigs |
|---|---|---|
| Untreated | 0.08 ± 0.01 (1) | na |
| Placebo | 0.02 ± 0.03 (4) | 0 ± 0* (3) |
| 1 μg/mL | 0 ± 0 (3) | 0 ± 0 (3) |

TABLE 11-4-continued

Dermis (ng/mg) Mean ± SD of Calcitriol Recovered
(n = Number of Animals [4 replicates/animal])

| Treatment | Male Minipigs | Female Minipigs |
|---|---|---|
| 3 µg/mL | 0 ± 0 (3) | 0 ± 0 (3) |
| 10 µg/mL | 0 ± 0 (3) | 0 ± 0 (3) |
| 30 µg/mL | 0 ± 0 (3) | 0 ± 0 (3) |
| 100 µg/mL | 0.13 ± 0.04 (1) | na |

*Zeros indicate results to be below the Lower Limit of Detection.
*na = not applicable The data indicate that calcitriol was measurable in most stratum corneum and epidermal samples, but not in the dermal samples (with the single exception of the 100 µg/mL dose application to a single male minipig). This is consistent with the results obtained in Franz human skin finite dose model described above in Example 1.

Across tissue samples evaluated, male minipigs appeared to demonstrate, in general, greater calcitriol tissue levels than female minipigs.

The highest concentrations of calcitriol were observed to be in the stratum corneum. Though the stratum corneum content is an estimated value, its higher concentration may reflect the presence of calcitriol deep in the pores of the skin, not removed by the surface wash process, or could be attributable to the solubility of calcitriol in the very lipophilic matrix of the stratum corneum.

The clearest applied dose correlation to tissue level, however, was observed in the epidermis with a near linear increase in calcitriol concentrations from 3 to 100 µg/mL applications.

Example 12. A Topical Solution Study in Chloroleukemic Rats Receiving Multi-Course Chemotherapy Long Evans Rats (Harlan Laboratories, Inc) were 3 days old upon arrival. The weight of the animals was obtained upon arrival and every day until the conclusion of the experiments using an electronic scale (American Scientific Products TL 410s). Rats were housed for two days prior to the beginning of experiments. Animals were then randomized in four groups. All rats received MIAC51 as described below.

Group 1 (n=27) received no further treatment.
Group 2 (n=40) received chemotherapy only.
Group 3 (n=40) received chemotherapy and topical vehicle as describe below.
Group 4, (n=40) received chemotherapy and topical calcitriol Treatments were started on day 6 after birth. A 0.1 mL amount of topical calcitriol was applied topically on the top of head and neck of the rats. For the first anagen cycle, on days 6 and 7, either vehicle or calcitriol was applied in a volume of 25 µl four times to avoid saturation. On days 8, 9, 10 and 11, a volume of 50 µl was applied twice. For the second anagen cycle, rats were treated with 0.1 mL of vehicle or calcitriol daily on days 40 to 45. Each application entailed rubbing an area of 2 cm$^2$ for 10 seconds with right index finger covered with a nitrile exam glove. After the completion of the treatments, each rat was individually separated for 6 hours. Subsequently each rat's head and back was washed with mild hand soap (Soft CIDE-EC from VWR International) and distilled water. Pups where then placed back with their mothers and taken back to the animal rooms. For the second anagen cycle, adult rats were placed back in their cages with their littermates and taken back to the animal rooms.

On day 5 after birth all rats received 1×105 MIAC51 intraperitoneally in 0.1 ml of serum free (SF) RPMI. MIAC51 were cultured in RPMI 1640 supplemented with L-glutamine and 10% fetal bovine serum at 370 in a 5% CO2, 100% humidity incubator. Cells were grown to 50% confluency (1.5×106 ml) collected in 50 ml conical tubes, centrifuged at 600 g for 10 minutes at room temperature and resuspended in SF-RPMI at a concentration of 1×106/ml prior to injection.

On day 23 after birth, a blood sample was taken from all rats and differentials were performed. Rats with leukemia were sacrificed while rats without leukemia were used for further experiments. A second differential was performed on day 31, and leukemic animals were sacrificed. Surviving animals were shaved an area of 2 cm$^2$ prior to the administration of the second set of vehicle or calcitriol treatment and a second course of chemotherapy was given 15 days later. In both the second and first anagen phase, alopecia was recorded ten days after chemotherapy treatment.

The extent of alopecia on each rat was determined by the following scale:

0=no alopecia
1+=0-25% alopecia
2+=25-50% alopecia
3+=50-75% alopecia
4+=75-100% alopecia Experimental Compounds The 2.3 µg/g calcitriol formulation was diluted with the vehicle (40% by weight propylene glycol and 60% by weight anhydrous 200 proof ethanol) to a final concentration of 2 µg/ml. Vials of 1 mL were subdivided and kept in the refrigerator at 4° C. For each experiment, one vial of 2.3 µg/g calcitriol and vehicle were taken out and placed on ice during the experimental procedure. Unused preparations were disposed of.

A. Cyclophosphamide Alone

Administration of Chemotherapy

Young Rats:

On day 13, all rats received cyclophosphamide (CTX) (Sigma Aldrich, Lot #068k1131) 37.5 mg/kg intraperitoneally using ½ cc insulin syringe 29G ½" (B-D) in a total volume of 0.1 mL of H$_2$O/mannitol mixture.

Adult Rats:

For the second course of chemotherapy, 150 mg/kg cyclophosphamide was administered to 47-day old rats to anesthetized (50 mg/kg ketamine/5 mg/kg xylazine) intraperitoneally using ½ cc insulin syringe 29G ½" (B-D) in a total volume of 0.1 mL of H$_2$O/mannitol mixture.

Results are seen in Tables 12-1 and 12-2. Specifically, after the first round of chemotherapy (Table 12-1 and FIG. 27), all rats receiving cyclophosphamide alone or cyclophosphamide in combination with the vehicle had severe alopecia (+4). In contrast, all rats that received cyclophosphamide in combination with calcitriol did not exhibit any signs of alopecia, similar to the control group. Similar results were obtained after the second round of chemotherapy, as shown in Table 12-2 (see also FIG. 28).

TABLE 12-1

Extent of Alopecia in Rats Treated with Cyclophosphamide (CTX) after First Round of Chemotherapy

| GROUP | ALOPECIA | | | | | Total | Group/Prob. | | Group/Prob. | |
|---|---|---|---|---|---|---|---|---|---|---|
| | 0 | 1+ | 2+ | 3+ | 4+ | | | | | |
| 1. Control (No chemotherapy) | 27 | | | | | 27 | 1 vs 2 | p < 0.01 | 2 vs 3 | p = 1.000 |
| 2. CTX | | | | | 40 | 40 | 1 vs 3 | p < 0.01 | 2 vs 4 | p < 0.01 |
| 3. CTX + Vehicle | | | | | 40 | 40 | 1 vs 4 | p = 1.000 | 3 vs 4 | p < 0.01 |
| 4. CTX + Calcitriol | 40 | | | | | 40 | | | | |

TABLE 12-2

Extent of Alopecia in Rats Treated with Cyclophosphamide (CTX) after Second Round of Chemotherapy

| GROUP | ALOPECIA | | | | | Total | Group/Prob. | |
|---|---|---|---|---|---|---|---|---|
| | 0 | 1+ | 2+ | 3+ | 4+ | | | |
| 2. CTX alone | | | | | 8 | 8 | 2 vs 3 | p = 1.000 |
| 3. CTX + Vehicle | | | | | 9 | 0 | 2 vs 4 | p < 0.01 |
| 4. CTX + Calcitriol | 10 | | | | | 10 | 3 vs 4 | p < 0.01 |

Further, this experiment indicated that the survival rate of the rats receiving the topical formulation of calcitriol was substantially similar to those rats receiving chemotherapy alone or in combination with the vehicle. As shown in Table 12-3, the survival rate of those animals treated with cyclophosphamide and the topical formulation of calcitriol (25%) was similar to those rats treated with cyclophosphamide alone (20%) and those rats treated with cyclophosphamide and vehicle (23%).

TABLE 12-3

Survival Rate of Rats Treated with Cyclophosphamide (CTX) after Two Rounds of Chemotherapy

| GROUP | Cured | % | Total | Group/Prob. | | Group/Prob. | |
|---|---|---|---|---|---|---|---|
| 1. Control (No chemotherapy) | 0 | 0 | 27 | | | | |
| 2. CTX | 8 | 20 | 40 | 1 vs. 2 | p < 0.01 | 2 vs. 3 | p = 0.7846 |
| 3. CTX + Vehicle | 9 | 23 | 40 | 1 vs. 3 | p < 0.01 | 2 vs. 4 | p = 0.5923 |
| 4. CTX + Calcitriol | 10 | 25 | 40 | 1 vs. 4 | p < 0.01 | 3 vs. 4 | p = 0.7927 |
| TOTAL | 27 | 18 | 147 | | | | |

In summary, in the cyclophosphamide group, calcitriol offered 100% protection from CIA in both cycles and did not interfere with the cure rate which was in the range of 20-25%.

B. Cyclophosphamide and Doxorubicin
Administration of Chemotherapy

Young Rats:

On day 13, all rats received Cyclophosphamide (CTX) (Sigma Aldrich, Lot #068k1131) 37.5 mg/kg intraperitoneally using ½ cc insulin syringe 29G ½" (B-D) in a total volume of 0.1 mL of $H_2O$/mannitol mixture. On days 13, 14, and 15 rats received doxorubicin hydrochloride (Sigma Aldrich, Lot #038k1349) (ADM) 2.5 mg/kg I.P. in 0.1 ml distilled water.

Adult Rats:

For the second course of chemotherapy, 150 mg/kg cyclophosphamide to anesthetized (50 mg/kg ketamine/5 mg/kg xylazine) intraperitoneally using ½ cc insulin syringe 29G½" (B-D) in a total volume of 0.1 mL of $H_2O$/mannitol mixture on day 47. For the second course of chemotherapy, rats received 20 mg/kg ADM on days 47 to 49 as described above.

Results are seen in Tables 12-4 and 12-5. Specifically, after the first round of chemotherapy (Table 12-4 and FIG. 29), all rats receiving cyclophosphamide and doxorubicin alone or in combination with the vehicle had severe alopecia (+4). In contrast, all rats that received cyclophosphamide and doxorubicin in combination with calcitriol did not exhibit any signs of alopecia, similar to the control group. Similar results were obtained after the second round of chemotherapy, as shown in Table 12-5 (see also FIG. 30).

TABLE 12-4

Extent of Alopecia in Rats Treated with Cyclophosphamide (CTX) and Doxorubicin (ADM) after First Round of Chemotherapy

| GROUP | ALOPECIA | | | | | Total | Group/Prob. | | Group/Prob. | |
|---|---|---|---|---|---|---|---|---|---|---|
| | 0 | 1+ | 2+ | 3+ | 4+ | | | | | |
| 1. Control (No chemotherapy) | 40 | | | | | 40 | 1 vs 2 | p < 0.01 | 2 vs 3 | p = 1.000 |
| 2. CTX + ADM | | | | | 40 | 40 | 1 vs 3 | p < 0.01 | 2 vs 4 | p < 0.01 |

TABLE 12-4-continued

Extent of Alopecia in Rats Treated with Cyclophosphamide (CTX) and Doxorubicin (ADM) after First Round of Chemotherapy

| GROUP | ALOPECIA | | | | | | Group/Prob. | | Group/Prob. | |
|---|---|---|---|---|---|---|---|---|---|---|
| | 0 | 1+ | 2+ | 3+ | 4+ | Total | | | | |
| 3. CTX + ADM + Vehicle | | | | | 40 | 40 | 1 vs 4 | p = 1.000 | 3 vs 4 | p < 0.01 |
| 4. CTX + ADM + Calcitriol | 40 | | | | | 40 | | | | |

TABLE 12-5

Extent of Alopecia in Rats Treated with Cyclophosphamide (CTX) and Doxorubicin (ADM) after Second Round of Chemotherapy

| GROUP | ALOPECIA | | | | | | Group/Prob. | |
|---|---|---|---|---|---|---|---|---|
| | 0 | 1+ | 2+ | 3+ | 4+ | Total | | |
| 2. CTX + ADM | | | | | 21 | 21 | 2 vs 3 | p = 1.000 |
| 3. CTX + ADM + Vehicle | | | | | 22 | 22 | 2 vs 4 | p < 0.01 |
| 4. CTX + ADM + Calcitriol | 20 | | | | | 20 | 3 vs 4 | p < 0.01 |

Further, this experiment indicated that the survival rate of the rats receiving the topical formulation of calcitriol was substantially similar to those rats receiving chemotherapy alone or in combination with the vehicle. As shown in Table 12-6, the survival rate of those animals treated with cyclophosphamide and doxorubicin in combination with the topical formulation of calcitriol (50%) was similar to those rats treated with chemotherapy alone (53%) and those rats treated with chemotherapy and vehicle (55%).

TABLE 12-6

Survival Rate of Rats Treated with Cyclophosphamide (CTX) and Doxorubicin (ADM) after Two Rounds of Chemotherapy

| GROUP | Cured | % | Total | Group/Prob. | | Group/Prob. | |
|---|---|---|---|---|---|---|---|
| 1. Control (No chemotherapy) | 0 | 0 | 40 | | | | |
| 2. CTX + ADM | 21 | 53 | 40 | 1 vs. 2 | p < 0.01 | 2 vs. 3 | p = 0.8225 |
| 3. CTX + ADM + Vehicle | 22 | 55 | 40 | 1 vs. 3 | p < 0.01 | 2 vs. 4 | p = 0.8230 |
| 4. CTX + ADM + Calcitriol | 20 | 50 | 40 | 1 vs. 4 | p < 0.01 | 3 vs. 4 | p = 0.9336 |
| TOTAL | 63 | 39 | 160 | | | | |

In summary, in the cyclophosphamide and doxorubicin group, calcitriol offered 100% protection from CIA in both cycles and did not interfere with the cure rate, which was in the range of 50-55%.

C. Cyclophosphamide, Doxorubicin and Cytarabine
Administration of Chemotherapy
Young Rats:
On day 13, all rats received Cyclophosphamide (CTX) (Sigma Aldrich, Lot #068k1131) 30 mg/kg intraperitoneally using ½ cc insulin syringe 29G ½" (B-D) in a total volume of 0.1 mL of $H_2O$/mannitol mixture. On days 13, 14, and 15 rats received 2.0 mg/kg doxorubicin hydrochloride (Sigma Aldrich, Lot #038k1349) (ADM) intraperitoneally in 0.1 ml distilled water and on days 13-19, the ras received 50 mg/kg cytarabine.

Adult Rats:
For the second course of chemotherapy, 100 mg/kg cyclophosphamide was administered to anesthetized rats (50 mg/kg ketamine/5 mg/kg xylazine) for one day, 20 mg/kg doxorubicin for three days and 100 mg/kg cytarabine for seven days.

Results are seen in Tables 12-7 and 12-8. Specifically, after the first round of chemotherapy (Table 12-7 and FIG. 31), all rats receiving cyclophosphamide, doxorubicin and cytarabine alone or cyclophosphamide, doxorubicin and cytarabine in combination with the vehicle had severe alopecia (+4). In contrast, all rats that received cyclophosphamide, doxorubicin and cytarabine in combination with calcitriol did not exhibit any signs of alopecia, similar to the control group. Similar results were obtained after the second round of chemotherapy, as shown in Table 12-8 (see FIG. 32).

TABLE 12-7

Extent of Alopecia in Rats Treated with Cyclophosphamide (CTX), Doxorubicin (ADM) and Cytarabine (ARA-C) after First Round of Chemotherapy

| GROUP | ALOPECIA | | | | | | Group/Prob. | | Group/Prob. | |
|---|---|---|---|---|---|---|---|---|---|---|
| | 0 | 1+ | 2+ | 3+ | 4+ | Total | | | | |
| 1. Control (No chemotherapy) | 40 | | | | | 40 | 1 vs 2 | p < 0.01 | 2 vs 3 | p = 1.000 |
| 2. CTX + ADM + ARA-C | | | | | 40 | 40 | 1 vs 3 | p < 0.01 | 2 vs 4 | p < 0.01 |
| 3. CTX + ADM + ARA-C + Vehicle | | | | | 40 | 40 | 1 vs 4 | p = 1.000 | 3 vs 4 | p < 0.01 |
| 4. CTX + ADM + ARA-C + Calcitriol | 40 | | | | | 40 | | | | |

TABLE 12-8

Extent of Alopecia in Rats Treated with Cyclophosphamide (CTX), Doxorubicin (ADM) and Cytarabine (ARA-C) after Second Round of Chemotherapy

| GROUP | ALOPECIA | | | | | | Group/Prob. | |
|---|---|---|---|---|---|---|---|---|
| | 0 | 1+ | 2+ | 3+ | 4+ | Total | | |
| 2. CTX + ADM + ARA-C | | | | | 32 | 32 | 2 vs 3 | p = 1.000 |
| 3. CTX + ADM + ARA-C + Vehicle | | | | | 30 | 30 | 2 vs 4 | p < 0.01 |
| 4. CTX + ADM + ARA-C + Calcitriol | 31 | | | | | 31 | 3 vs 4 | p < 0.01 |

Further, this experiment indicated that the survival rate of the rats receiving the topical formulation of calcitriol was substantially similar to those rats receiving chemotherapy alone or in combination with the vehicle. As shown in Table 12-9, the survival rate of those animals treated with cyclophosphamide, doxorubicin and cytarabine in combination with the topical formulation of calcitriol (78%) was similar to those rats treated with chemotherapy alone (80%) and those rats treated with chemotherapy and vehicle (75%).

TABLE 12-9

Survival Rate of Rats Treated with Cyclophosphamide (CTX), Doxorubicin (ADM) and Cytarabine (ARA-C) after Two Rounds of Chemotherapy

| GROUP | Cured | % | Total | Group/Prob. | | Group/Prob. | |
|---|---|---|---|---|---|---|---|
| 1. Control (No chemotherapy) | 0 | 0 | 40 | | | | |
| 2. CTX + ADM + ARA-C | 32 | 80 | 40 | 1 vs. 2 | p < 0.01 | 2 vs. 3 | p = 0.5923 |
| 3. CTX + ADM + ARA-C + Vehicle | 30 | 75 | 40 | 1 vs. 3 | p < 0.01 | 2 vs. 4 | p = 0.5501 |
| 4. CTX + ADM + ARA-C + Calcitriol | 31 | 78 | 40 | 1 vs. 4 | p < 0.01 | 3 vs. 4 | p = 0.7927 |
| TOTAL | 93 | 58 | 160 | | | | |

In summary, in the cyclophosphamide, doxorubicin and cytarabine group, calcitriol offered 100% protection from CIA in both cycles and did not interfere with the cure rate, which was in the range of 75-80%.

D. Cyclophosphamide, Paclitaxel and Etoposide

Administration of Chemotherapy

Young Rats:

On day 13, all rats received Cyclophosphamide (CTX) (Sigma Aldrich, Lot #068k1131) 37.5 mg/kg intraperitoneally using ½ cc insulin syringe 29G ½" (B-D) in a total volume of 0.1 mL of H$_2$O/mannitol mixture. On days 11 to 13, rats concomitantly received 2.5 mg/kg paclitaxel (Taxol) in 0.1 mL dimethyl sulfoxide (Sigma Aldrich, Lot #078K1428) and 1.5 mg/kg etoposide (VP-16) (Sigma Aldrich, Lot #047K1162) diluted in special solvent (see Standard Operating Procedures) and HBSS.

Adult Rats:

For the second course of chemotherapy, 150 mg/kg cyclophosphamide to anesthetized (50 mg/kg ketamine/5 mg/kg xylazine) intraperitoneally using ½ cc insulin syringe 29G½" (B-D) in a total volume of 0.1 mL of H$_2$O/mannitol mixture on day 47. For the second course of chemotherapy, rats received 10 mg/kg Taxol and 15 mg/kg VP-16 on days 45 to 48 as described above.

Results are seen in Tables 12-10 and 12-11. Specifically, after the first round of chemotherapy (Table 12-10 and FIG. 33), all rats receiving cyclophosphamide, paclitaxel and etoposide alone or cyclophosphamide, paclitaxel and etoposide in combination with the vehicle had severe alopecia (+4). In contrast, all rats that received cyclophosphamide, paclitaxel and etoposide in combination with calcitriol did not exhibit any signs of alopecia, similar to the control group. Similar results were obtained after the second round of chemotherapy, as shown in Table 12-11 (see also FIG. 34).

TABLE 12-10

Extent of Alopecia in Rats Treated with Cyclophosphamide (CTX), Paclitaxel and Etoposide after First Round of Chemotherapy

| GROUP | ALOPECIA | | | | | | Group/Prob. | | Group/Prob. | |
|---|---|---|---|---|---|---|---|---|---|---|
| | 0 | 1+ | 2+ | 3+ | 4+ | Total | | | | |
| 1. Control (No chemotherapy) | 40 | | | | | 40 | 1 vs 2 | p < 0.01 | 2 vs 3 | p = 1.000 |
| 2. CTX + PACLITAXEL + ETOPOSIDE | | | | | 40 | 40 | 1 vs 3 | p < 0.01 | 2 vs 4 | p < 0.01 |
| 3. CTX + PACLITAXEL + ETOPOSIDE + Vehicle | | | | | 40 | 40 | 1 vs 4 | p = 1.000 | 3 vs 4 | p < 0.01 |
| 4. CTX + PACLITAXEL + ETOPOSIDE + CALCITRIOL | 40 | | | | | 40 | | | | |

TABLE 12-11

Extent of Alopecia in Rats Treated with Cyclophosphamide (CTX),
Paclitaxel and Etoposide after Second Round of Chemotherapy

| GROUP | ALOPECIA | | | | | | | |
|---|---|---|---|---|---|---|---|---|
| | 0 | 1+ | 2+ | 3+ | 4+ | Total | Group/Prob. | |
| 2. CTX + PACLITAXEL + ETOPOSIDE | | | | | 33 | 33 | 2 vs 3 | p = 1.000 |
| 3. CTX + PACLITAXEL + ETOPOSIDE + Vehicle | | | | | 31 | 31 | 2 vs 4 | p < 0.01 |
| 4. CTX + PACLITAXEL + ETOPOSIDE + CALCITRIOL | 33 | | | | | 33 | 3 vs 4 | p < 0.01 |

Further, this experiment indicated that the survival rate of the rats receiving the topical formulation of calcitriol was substantially similar to those rats receiving chemotherapy alone or in combination with the vehicle. As shown in Table 12-12, the survival rate of those animals treated with cyclophosphamide, paclitaxel and etoposide in combination with the topical formulation of calcitriol (83%) was similar to those rats treated with chemotherapy alone (83%) and those rats treated with chemotherapy and vehicle (78%).

TABLE 12-12

Survival Rate of Rats Treated with Cyclophosphamide (CTX),
Paclitaxel and Etoposide after Two Rounds of Chemotherapy

| GROUP | Cured | % | Total | Group/Prob. | | Group/Prob. | |
|---|---|---|---|---|---|---|---|
| 1. Control (No chemotherapy) | 0 | 0 | 40 | | | | |
| 2. CTX + PACLITAXEL + ETOPOSIDE | 33 | 83 | 40 | 1 vs. 2 | p < 0.01 | 2 vs. 3 | p = 0.5762 |
| 3. CTX + PACLITAXEL + ETOPOSIDE + Vehicle | 31 | 78 | 40 | 1 vs. 3 | p < 0.01 | 2 vs. 4 | p = 1.000 |
| 4. CTX + PACLITAXEL + ETOPOSIDE + CALCITRIOL | 33 | 83 | 40 | 1 vs. 4 | p < 0.01 | 3 vs. 4 | p = 0.5762 |

In summary, in the cyclophosphamide, paclitaxel and etoposide group, calcitriol offered 100% protection from CIA in both cycles and did not interfere with the cure rate which was in the range of 78-83%.

E. Doxorubicin, Paclitaxel and Etoposide

Administration of Chemotherapy

Young Rats:

On day 13 through 15, all rats received doxorubicin hydrochloride (Sigma Aldrich, Lot #038k1349) (ADM) 2.5 mg/kg in 0.1 ml distilled water intraperitoneally using ½ cc_insulin syringe 29G½" (B-D). Concomitantly, rats received 2.5 mg/kg paclitaxel (Taxol)_(Sigma Aldrich, Lot #078k1428) and 1.5 mg/kg etoposide (VP-16) (Sigma Aldrich, Lot #047k1162).

Adult Rats:

For the second course of chemotherapy, the above chemotherapies were started on day 47 through 49 on anesthetized rats (50 mg/kg ketamine/5 mg/kg xylazine) intraperitoneally using ½ cc insulin syringe 29G½" (B-D) in a total volume of 0.1 mL. Dosages for the second course were as follows: 20 mg/kg ADM, 10 mg/kg Taxol and 15 mg/kg VP-16.

Results are seen in Tables 12-12 and 12-14. Specifically, after the first round of chemotherapy (Table 12-13 and FIG. 35), all rats receiving doxorubicin, paclitaxel and etoposide alone or doxorubicin, paclitaxel and etoposide in combination with the vehicle had severe alopecia (+4). In contrast, all rats that received doxorubicin, paclitaxel and etoposide in combination with calcitriol did not exhibit any signs of alopecia, similar to the control group. Similar results were obtained after the second round of chemotherapy, as shown in Table 12-14 (see also FIG. 36).

TABLE 12-13

Extent of Alopecia in Rats Treated with Doxorubicin (ADM), Paclitaxel and Etoposide after First Round of Chemotherapy

| GROUP | ALOPECIA | | | | | | | | | |
|---|---|---|---|---|---|---|---|---|---|---|
| | 0 | 1+ | 2+ | 3+ | 4+ | Total | Group/Prob. | | Group/Prob. | |
| 1. Control (No chemotherapy) | 40 | | | | | 40 | 1 vs 2 | p < 0.01 | 2 vs 3 | p = 1.000 |
| 2. ADM + PACLITAXEL + ETOPOSIDE | | | | | 40 | 40 | 1 vs 3 | p < 0.01 | 2 vs 4 | p < 0.01 |
| 3. ADM + PACLITAXEL + ETOPOSIDE + Vehicle | | | | | 40 | 40 | 1 vs 4 | p = 1.000 | 3 vs 4 | p < 0.01 |
| 4. ADM + PACLITAXEL + ETOPOSIDE + Calcitriol | 40 | | | | | 40 | | | | |

TABLE 12-14

Extent of Alopecia in Rats Treated with Doxorubicin (ADM),
Paclitaxel and Etoposide after Second Round of Chemotherapy

| GROUP | ALOPECIA | | | | | Total | Group/Prob. | |
|---|---|---|---|---|---|---|---|---|
| | 0 | 1+ | 2+ | 3+ | 4+ | | | |
| 2. ADM + PACLITAXEL + ETOPOSIDE | | | | | 32 | 32 | 2 vs 3 | p = 1.000 |
| 3. ADM + PACLITAXEL + ETOPOSIDE + Vehicle | | | | | 33 | 33 | 2 vs 4 | p < 0.01 |
| 4. ADM + PACLITAXEL + ETOPOSIDE + Calcitriol | 32 | | | | | 32 | 3 vs 4 | p < 0.01 |

Further, this experiment indicated that the survival rate of the rats receiving the topical formulation of calcitriol was substantially similar to those rats receiving chemotherapy alone or in combination with the vehicle. As shown in Table 12-15, the survival rate of those animals treated with doxorubicin, paclitaxel and etoposide in combination with the topical formulation of calcitriol (80%) was similar to those rats treated with chemotherapy alone (80%) and those rats treated with chemotherapy and vehicle (83%).

TABLE 12-15

Survival Rate of Rats Treated with Doxorubicin (ADM), Paclitaxel
and Etoposide after Two Rounds of Chemotherapy

| GROUP | Cured | % | Total | Group/Prob. | | Group/Prob. | |
|---|---|---|---|---|---|---|---|
| 1. Control (No chemotherapy) | 0 | 0 | 40 | | | | |
| 2. ADM + PACLITAXEL + ETOPOSIDE | 32 | 80 | 40 | 1 vs. 2 | p < 0.01 | 2 vs. 3 | p = 0.5762 |
| 3. ADM + PACLITAXEL + ETOPOSIDE + Vehicle | 33 | 83 | 40 | 1 vs. 3 | p < 0.01 | 2 vs. 4 | p = 1.000 |
| 4. ADM + PACLITAXEL + ETOPOSIDE + Calcitriol | 32 | 80 | 40 | 1 vs. 4 | p < 0.01 | 3 vs. 4 | p = 0.5762 |

In summary, in the doxorubicin, paclitaxel and etoposide group, calcitriol offered 100% protection from CIA in both cycles and did not interfere with the cure rate which was in the range of 80-83%.

Example 13. A 4-Week Dermal Toxicity Study of Topical Calcitriol in Gottingen Minipigs®

Control, Vehicle, and Test Article Preparation:

Fresh control article, 0.9% Sodium Chloride for Injection, USP, was dispensed for use on study weekly and was stored refrigerated. The vehicle, a 40/60 mixture by weight (w/w) of Propylene Glycol, USP and Ethanol (undenatured, anhydrous) 200 Proof USP, and the test article, containing Calcitriol, USP, with a specific gravity of 0.875, was used as received from and no adjustment was made for purity. The test article was received at concentrations of 5.07, 10.31, and 55.34 µg/mL. The test article was administered neat (undiluted). The vehicle and test article were dispensed for use on study weekly and stored refrigerated. On occasion, additional test material was dispensed as necessary during the course of the study.

Administration:

Prior to administration, the hair was clipped from the back of the animal. The control animals had two test sites; site 1 was treated with the vehicle and site 2 with saline. Each site was 450 cm$^2$, bilaterally divided by the spine, and marked at the corners with indelible marker. The two test sites for the control group were evenly divided. Repeated clipping of the hair was done as necessary. Care was taken to avoid abrading the skin. The control article, vehicle, and test article were administered twice per day approximately 6 hours apart for 4 weeks (29 consecutive days) during the study dermally. The formulation was uniformly applied over the application site with a glass stirring rod or appropriate instrument. Any residual test material was gently removed prior to the next dose with a Wypall, wet with tap water. If necessary, sites were dried with a clean, dry Wypall. The dose administered to all animals was 1800 mg of the appropriate formulation. The dose concentrations were 5.07, 10.31, and 55.34 µg/mL and administered at a dose volume of 2.1 mL. The control article and vehicle were administered to the control group in the same manner as the treated groups. The dosing volume for the control animals was 1.0 mL of the vehicle and 0.9 mL of saline. Due to the severity of clinical signs observed, all animals at 55.34 µg/mL were not dosed on Day 23. Dosing resumed for all animals on Day 24.

Results:

This study was conducted for to evaluate the potential subchronic toxicity of a calcitriol topical solution, when administered twice daily via dermal application for 4 weeks. Three treatment groups of four animals/sex/group of Gottingen Minipig® were administered the calcitriol topical solution at respective dose concentrations of 5.07, 10.31, and 55.34 µg/mL. One additional group of four animals/sex served as the control and received the vehicle, a 40/60 mixture by weight (w/w) of Propylene Glycol, USP and Ethanol (undenatured, anhydrous) 200 Proof USP, and the control article, 0.9% Sodium Chloride for Injection, USP. The calcitriol topical solution or vehicle was administered to all groups via dermal application, twice a day for 29 consecutive days, at a dose volume of 4 mg/cm$^2$ over a 450 cm$^2$ test site.

Observations for morbidity, mortality, injury, and the availability of food and water were conducted twice daily for all animals. Clinical observations were conducted weekly. Body weights were measured and recorded weekly. Dermal irritation scoring was done after each dose during Week 1 and then twice per week (after the second dose) during Weeks 2 through 4 for changes in the application site. Ophthalmoscopic examinations were conducted pretest and all survivors prior to terminal necropsy. Physical examinations were conducted pretest. Electrocardiographic examinations were conducted pretest, predose, and 1 to 2 hours post the first dose on Day 1 and during the last week of dosing. Blood and urine samples for clinical pathology evaluations were collected from all animals pretest and prior to the terminal necropsy. Blood samples for determination of the plasma concentrations of the test article were collected from all surviving animals at designated time points on Days 1 and 27. The toxicokinetic (TK) parameters were determined for the test article from concentration-time data in the test species. At study termination, necropsy examinations were performed, organ weights were recorded, and selected tissues were microscopically examined.

One male at the 55.34 µg/mL concentration was euthanized in extremis on Day 28 of the study. This animal was observed with decreased activity, inappetence, and tremors prior to euthanasia. The cause of the morbidity of this animal was considered to be the high calcium blood levels that were close to the lethal level. All remaining minipigs survived to their scheduled termination on Day 30 of the study. Decreased activity, inappetence, emesis, and tremors were observed in most minipigs at the 55.34 µg/mL concentration during Weeks 3 and 4 of the study. Mild irritation was observed in males and females at the 55.34 µg/mL concentration during the last week or two of the study. Mean body weights and body weight gains for the treated males and females at 5.07 and 10.31 µg/mL were comparable to controls. All males and females at the 55.34 µg/mL concentration lost a significant amount of body weight during the last 2 weeks of the study and the mean body weights were significantly lower in males and females during this time period.

No ophthalmoscopic abnormalities were observed in any of the animals at the pretest and terminal ophthalmoscopic examinations. The calcitriol topical solution did not cause qualitative electrocardiogram abnormalities, but there was a mild increase in the group mean heart rates at the terminal predose and postdose intervals. This increase in heart rate is undoubtedly related to the marked increase in calcium levels in these minipigs during the study. There were no other dose-related effects of the calcitriol topical solution on quantitative electrocardiogram parameters. No calcitriol topical solution-related hematology, coagulation or urinalysis alterations were observed in males or females at the terminal evaluation. Some clinical chemistry alterations were seen at the 55.34 µg/mL concentration, the most notable was the high calcium levels observed that were near the lethal level. The other changes seen were lower chloride values, and higher cholesterol, glucose, urea nitrogen, and triglyceride values.

Calcitriol topical solution-related macroscopic pathology findings were limited to the stomach mucosa of one female at the 55.34 µg/mL concentration consisting of a mild, irregular surface. Absolute and relative increased weight of the kidney and decreased weight of the thymus were seen in both sexes at the 55.34 µg/mL concentration compared to controls. Direct calcitriol topical solution-related microscopic findings were present in the bones, kidneys, heart, treated skin, thymus, and thyroid gland. In addition, direct calcitriol topical solution-related findings included multicentric vascular changes and multicentric mucosal mineralization. Indirect test article related microscopic findings were noted in the pancreas. These microscopic changes were present in both genders and were limited to animals dosed at the 55.34 µg/mL concentration.

The microscopic changes of the femoral, sternal, and costal bones were limited to the diaphyseal cortical bone and to the bone cavity. They were characterized by osteodystrophy and by the deposition of basophilic matrix. The renal microscopic observations were characterized by mineralization, tubular degeneration/regeneration and by a subacute inflammation. The microscopic observations of the myocardium were myofiber mineralization, subacute inflammation and vascular changes. In addition, one male and one female had endocardial mineralization. Multicentric mucosal/epithelial mineralization was observed in decreasing order within the stomach mucosa, lungs, larynx, trachea, prostate gland, salivary mandibular gland, and within the urinary bladder. Calcitriol topical solution-related vascular changes were widespread and affected primarily small to medium-sized blood vessels. They were primarily observed within the heart and the bone cavity and sporadically in different organs/systems. The microscopic changes of the treated skin were characterized by epidermal hyperplasia and hyperkeratosis and perivascular mixed cell inflammation with the superficial dermis. The microscopic changes of the thymus, thyroid gland and pancreas were characterized by lymphoid depletion, follicular cell hypertrophy and hyperplasia and single cell necrosis respectively.

On the basis of the results of this study, the no-observed-adverse-effect-level (NOAEL) was considered to be 10.31 µg/mL based upon the clinical chemistry and microscopic changes seen at the 55.34 µg/mL concentration.

REFERENCES

Diker-Cohen T, Koren R, Liberman U A, Ravid A Vitamin D protects keratinocytes from apoptosis induced by osmotic shock, oxidative stress, and tumor necrosis factor." *Ann NY Acad Sci.* 2003 December; 1010:350-3.

(ClinicalTrials.gov, Mosby's Drug Consult, 13th Edition).

Genever P G, Maxfield, S J, Kennovin G D, Maltman J, Bowgen C H, Raxworthy M J, Skerry T M. Evidence for a novel glutamate-mediated signaling pathway in keratinocytes. *J Invest Dermatol.* 1999 March; 112 (3): 337-42.

Kiryu-Seo S, Gamo K, Tachibana T, Tanaka K, Kiyama H. Unique anti apoptotic activity of EAAC1 in injured motor neurons. *The EMBO Journal* (2006) 25, 3411-3421.

Nollen E A, Bruntsing J F, Roelofsen H, Weber La, Kampinga H H. In vivo chaperon activity of heat shock protein 70 and thermotolerance. *Mol Cell Biol* 1999; 19: 2069-79.

Rocchi P, Jugpal P, SoA, Sinneman S, Ettinger S, Fazli L, Nelson C, Gleave M. Small interence RNA targeting heat shock protein 27 inhibits the growth of prostatic cell lines and induces apoptosis via caspase 3 activation in vitro *BJU Int* 2006.

Marenholz I, Heizmann C W, Fritz G (2004). S100 proteins in mouse and man: from evolution to function and pathology (including an update of the nomenclature). Biochem. Biophys. Res. Commun. 322 (4): 1111-22.

All referenced cited herein are incorporated by reference.

The invention claimed is:

1. A pharmaceutical composition comprising a vitamin D compound and a carrier; wherein the carrier consists of propylene glycol and ethanol at a % (w/w) ratio of propylene glycol to ethanol selected from the group consisting of 35:65; 36:64; 37:63; 38:62; 39:61; 40:60; 41:59; 42:58; 43:57; 44:56; and 45:55; and wherein the vitamin D compound is represented by Formula (I):

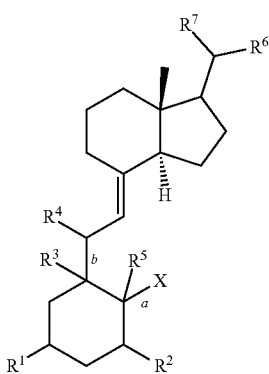

(I)

wherein
a and b are each independently a single or double bond;
X is —CH₂ when a is a double bond, or X is hydrogen or a hydroxyl substituted alkyl when a is a single bond;
$R^1$ is hydrogen, hydroxyl, alkoxyl, tri-alkyl silyl or alkyl, optionally substituted with one to three halogen, hydroxyl, cyano or —NR'R" moieties;
$R^2$ is hydrogen, hydroxyl, —O-trialkyl silyl, or alkyl, alkoxyl or alkenyl, optionally substituted with one to three halogen, hydroxyl, cyano or —NR'R" moieties;
$R^3$ is absent when b is a double bond or $R^3$ is hydrogen, hydroxyl or alkyl, or $R^3$ and $R^1$ together with the carbon atoms to which they are attached may be linked to form 5-7 membered carbocyclic ring when b is a single bond;
$R^4$ is absent when b is a double bond or hydrogen, halogen or hydroxyl when b is a single bond;
$R^5$ is absent when a is a double bond or $R^5$ is hydrogen, halogen or hydroxyl when a is a single bond;
$R^6$ is alkyl, alkenyl, alkynyl, cycloalkyl, heterocyclicyl, alkyl-O-alkyl, alkyl-CO₂-alkyl optionally substituted with one to five, hydroxyl, oxo, halogen, alkoxyl, aryl, heteroaryl, cyano, nitro or —NR'R" moieties;
$R^7$ is alkyl optionally substituted with one to three hydroxyl, halogen, alkoxyl, aryl, heteroaryl, cyano, nitro or —NR'R" moieties;
R' and R" are each, independently, hydrogen, hydroxyl, halogen, alkyl or alkoxyl;
the alkyl group is a fully saturated branched or unbranched having 1 to 20 carbon atoms;
the alkoxy group has 1-7 carbon atoms;
the alkenyl group is selected from the group consisting of vinyl, prop-1-enyl, allyl, butenyl, isopropenyl and isobutenyl;
the alkynyl group is selected from the group consisting of ethynyl, prop-1-ynyl (propargyl), butynyl, isopropynyl and isobutynyl;
the cycloalkyl group is a saturated or an unsaturated monocyclic, bicyclic, or tricyclic hydrocarbon group of 3-12 carbon atoms;
the aryl group is a monocyclic or bicyclic aromatic hydrocarbon group having 6-20 carbon atoms in the ring portion;
the heteroaryl group is a monocyclic or bicyclic aryl group, containing from 5-10 ring members selected from carbon atoms and 1 to 5 heteroatoms selected from O, N or S; and the heterocyclyl is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system, in which contains at least one heteroatom selected from O, S and N, where the N and S can also optionally be oxidized to various oxidation states, and pharmaceutically acceptable salts thereof, wherein the pharmaceutical composition comprises 3-100 µg/mL of the vitamin D compound.

2. The pharmaceutical composition of claim 1, wherein the vitamin D compound is represented by Formula (II):

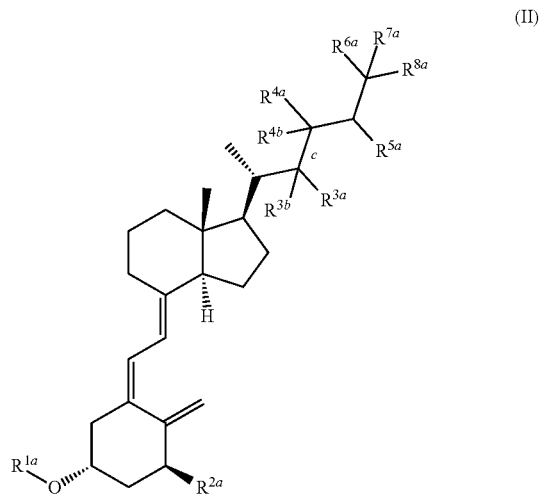

(II)

wherein
c is a single or double bond;
$R^{1a}$ is hydrogen or alkyl, optionally substituted with one to three halogen, hydroxyl, cyano or —NR'R" moieties;
$R^{2a}$ is hydrogen, hydroxyl, —O-trialkyl silyl, or alkyl, alkoxyl or alkenyl, optionally substituted with one to three halogen, hydroxyl, cyano or —NR'R" moieties;
$R^{3a}$ and $R^{4a}$ are absent when c is a double bond, or are each independently hydrogen, hydroxyl, halogen, alkoxyl or alkyl optionally substituted with one to three hydroxyl or halogen moieties when c is a single bond; and
$R^{3b}$, $R^{4b}$, $R^{5a}$, $R^{6a}$, $R^{7a}$ and $R^{8a}$ are each, independently, hydrogen, hydroxyl, halogen, alkoxyl or alkyl optionally substituted with one to three hydroxyl or halogen moieties, or any two of $R^{6a}$, $R^{7a}$ and $R^{8a}$ may be linked to form a 3-7 membered carbocyclic ring, and pharmaceutically acceptable salts thereof.

3. The pharmaceutical composition of claim 1, wherein the vitamin D compound is 1,25-dihydroxyvitamin D3; 1,25-dihydroxy-16-ene-23-yne-cholecalciferol; 1α-hydroxyvitamin D3; 1α,24-dihydroxyvitamin D3; or MC 903.

4. The pharmaceutical composition of claim 1, wherein the vitamin D compound is 1,25-dihydroxyvitamin D3.

5. The pharmaceutical composition of claim 1, wherein the vitamin D compound modulates the expression of HSPA2, HSF4, HSPB1 or DNAJC6 in normal keratinocytes.

6. The pharmaceutical composition of claim 1, wherein the vitamin D compound modulates the expression of SLC1A1, KCNB2, KCNN4 or SLC1A3 in normal keratinocytes.

7. The pharmaceutical composition of claim 1, wherein the vitamin D compound decreases the expression of one or more proteins selected from the group consisting of Crk II, Growth Factor Independence 1, Serine Threonine Protein Phosphatase 1b, Cathepsin D, Transforming Growth Factor b pan, WAVE, Protein Tyrosine Phosphatase PEST, and CD40 by at least about 2-fold.

8. The pharmaceutical composition of claim 1, wherein the vitamin D compound induces overexpression of one or more proteins selected from the group consisting of BACH1, CENPE, cMyc, C-src tryosine kinase (Csk), CtBP1, Dimethyl Histone H3 diMeLys4, Dimethyl Histone H3 diMeLys9, Estrogen Receptor, FKHRL1 (FOXO3a), FOXP2, HDAC2, HDAC6, MAP Kinase Activated Protein Kinase 2 (MAPKAPK2), MAP Kinase ERK1, Melanocortin 3 Receptor, Proliferating Cell Protein Ki67, S100, SHPTP2, Sin3A, ARTS, ASAP1 Centaurin b4, Cofilin, Connexin 32, Dystrophin, Focal Adhesion Kinase pp125FAK, gTubulin, Myosin IX Myr5, Neurofilament 200, p120ctn, PAD14, Par4 Prostate Apoptosis Response 4, ROCK1, Uvomorulin ECadherin, Vitronectin, Bclx, BclxL, BID, Bmf, DcR2, ERK5, Integrin-linked kinase (ILK), Protein Kinase Ba, PUMA bbc3, Amyloid Precursor Protein, Presenilin1, Glutamic Acid Decarboxylase 65, Glutamic Acid Decarboxylase 67, Nitric Oxide Synthase (bNOS), Substance P Receptor, Synaptopodin, Tumor Necrosis Factor a, and Ubiquitin C-terminal Hydrolase L1 by at least about 2-fold.

9. The pharmaceutical composition of claim 1, wherein the vitamin D compound induces overexpression in normal keratinocytes of one or more of: Glutathione S-transferase (GST), Keratin 1, Keratin 17, Galectin 1, S100 A9 (Calprotectin), and S100 A13.

10. The pharmaceutical composition of claim 1, wherein the % (w/w) ratio of propylene glycol to ethanol is 40:60.

11. A pharmaceutical composition comprising a vitamin D compound and a carrier, wherein the carrier consists of propylene glycol, ethanol and ethoxydiglycol or 2-(2-ethoxyethoxy)ethanol; wherein propylene glycol is present at about 30% (w/w), ethanol is present at about 60% (w/w), and ethoxydiglycol or 2-(2-ethoxyethoxy)ethanol is present at about 10% (w/w); and wherein the vitamin D compound is represented by Formula (I):

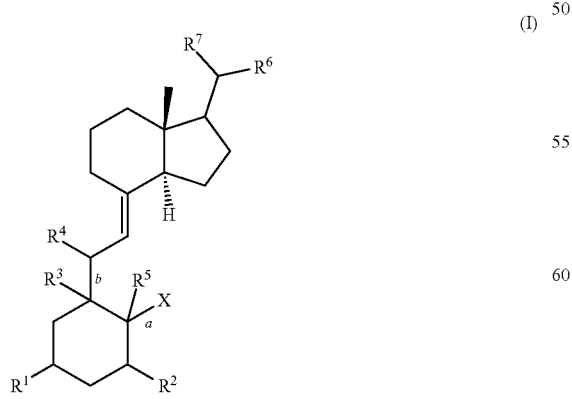

(I)

wherein a and b are each independently a single or double bond;

X is —$CH_2$ when a is a double bond, or X is hydrogen or a hydroxyl substituted alkyl when a is a single bond;

$R^1$ is hydrogen, hydroxyl, alkoxyl, tri-alkyl silyl or alkyl, optionally substituted with one to three halogen, hydroxyl, cyano or —NR'R" moieties;

$R^2$ is hydrogen, hydroxyl, —O-trialkyl silyl, or alkyl, alkoxyl or alkenyl, optionally substituted with one to three halogen, hydroxyl, cyano or —NR'R" moieties;

$R^3$ is absent when b is a double bond or $R^3$ is hydrogen, hydroxyl or alkyl, or $R^3$ and $R^1$ together with the carbon atoms to which they are attached may be linked to form 5-7 membered carbocyclic ring when b is a single bond;

$R^4$ is absent when b is a double bond or hydrogen, halogen or hydroxyl when b is a single bond;

$R^5$ is absent when a is a double bond or $R^5$ is hydrogen, halogen or hydroxyl when a is a single bond;

$R^6$ is alkyl, alkenyl, alkynyl, cycloalkyl, heterocyclicyl, alkyl-O-alkyl, alkyl-$CO_2$-alkyl optionally substituted with one to five, hydroxyl, oxo, halogen, alkoxyl, aryl, heteroaryl, cyano, nitro or —NR'R" moieties;

$R^7$ is alkyl optionally substituted with one to three hydroxyl, halogen, alkoxyl, aryl, heteroaryl, cyano, nitro or —NR'R" moieties;

R' and R" are each, independently, hydrogen, hydroxyl, halogen, alkyl or alkoxyl;

the alkyl group is a fully saturated branched or unbranched having 1 to 20 carbon atoms;

the alkoxy group has 1-7 carbon atoms;

the alkenyl group is selected from the group consisting of vinyl, prop-1-enyl, allyl, butenyl, isopropenyl and isobutenyl;

the alkynyl group is selected from the group consisting of ethynyl, prop-1-ynyl (propargyl), butynyl, isopropynyl and isobutynyl;

the cycloalkyl group is a saturated or an unsaturated monocyclic, bicyclic, or tricyclic hydrocarbon group of 3-12 carbon atoms;

the aryl group is a monocyclic or bicyclic aromatic hydrocarbon group having 6-20 carbon atoms in the ring portion;

the heteroaryl group is a monocyclic or bicyclic aryl group, containing from 5-10 ring members selected from carbon atoms and 1 to 5 heteroatoms selected from O, N or S; and the heterocyclyl is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system, in which contains at least one heteroatom selected from O, S and N, where the N and S can also optionally be oxidized to various oxidation states, and pharmaceutically acceptable salts thereof.

12. The pharmaceutical composition of claim 11, wherein the vitamin D compound is represented by Formula (II):

(II)

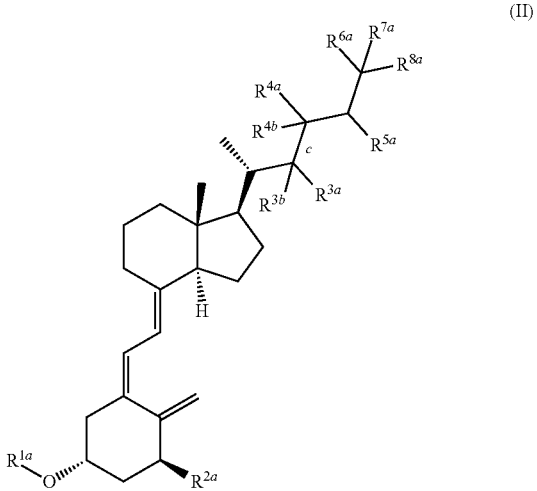

wherein
c is a single or double bond;
$R^{1a}$ is hydrogen or alkyl, optionally substituted with one to three halogen, hydroxyl, cyano or —NR'R" moieties;
$R^{2a}$ is hydrogen, hydroxyl, —O-trialkyl silyl, or alkyl, alkoxyl or alkenyl, optionally substituted with one to three halogen, hydroxyl, cyano or —NR'R" moieties;
$R^{3a}$ and $R^{4a}$ are absent when c is a double bond, or are each independently hydrogen, hydroxyl, halogen, alkoxyl or alkyl optionally substituted with one to three hydroxyl or halogen moieties when c is a single bond; and
$R^{3b}$, $R^{4b}$, $R^{5a}$, $R^{6a}$, $R^{7a}$ and $R^{8a}$ are each, independently, hydrogen, hydroxyl, halogen, alkoxyl or alkyl optionally substituted with one to three hydroxyl or halogen moieties, or any two of $R^{6a}$, $R^{7a}$ and $R^{8a}$ may be linked to form a 3-7 membered carbocyclic ring, and pharmaceutically acceptable salts thereof.

13. The pharmaceutical composition of claim 11, wherein the vitamin D compound is 1,25-dihydroxyvitamin D3; 1,25-dihydroxy-16-ene-23-yne-cholecalciferol; 1α-hydroxyvitamin D3; 1α,24-dihydroxyvitamin D3; or MC 903.

14. The pharmaceutical composition of claim 11, wherein the vitamin D compound is 1,25-dihydroxyvitamin D3.

15. A pharmaceutical composition comprising 1,25-dihydroxyvitamin D3 and a carrier, wherein the carrier consists of propylene glycol and ethanol at a % (w/w) ratio of propylene glycol to ethanol selected from the group consisting of 35:65; 36:64; 37:63; 38:62; 39:61; 40:60; 41:59; 42:58; 43:57; 44:56; and 45:55, wherein the pharmaceutical composition comprises 3-100 µg/mL of 1,25-dihydroxyvitamin D3.

16. The pharmaceutical composition of claim 15, wherein the % (w/w) ratio of propylene glycol to ethanol is 40:60.

17. The pharmaceutical composition of claim 15, wherein the pharmaceutical composition comprises about 5, 10 or 20 µg/mL of 1,25-dihydroxyvitamin D3.

18. A pharmaceutical composition comprising 1,25-dihydroxyvitamin D3 and a carrier, wherein the carrier consists of propylene glycol, ethanol and ethoxydiglycol or 2-(2-ethoxyethoxy)ethanol; and wherein propylene glycol is present at about 30% (w/w), ethanol is present at about 60% (w/w), and ethoxydiglycol or 2-(2-ethoxyethoxy)ethanol is present at about 10% (w/w).

19. The pharmaceutical composition of claim 18, wherein the pharmaceutical composition comprises 3-100 µg/mL of 1,25-dihydroxyvitamin D3.

20. The pharmaceutical composition of claim 18, wherein the pharmaceutical composition comprises about 5, 10 or 20 µg/mL of 1,25-dihydroxyvitamin D3.

* * * * *